United States Patent
Glezer et al.

(10) Patent No.: US 12,139,754 B2
(45) Date of Patent: *Nov. 12, 2024

(54) POLYNUCLEOTIDE BARCODES FOR LONG READ SEQUENCING

(71) Applicant: Singular Genomics Systems, Inc., La Jolla, CA (US)

(72) Inventors: Eli N. Glezer, Del Mar, CA (US); Martin Maria Fabani, Encinitas, CA (US); Ryan Shultzaberger, San Diego, CA (US); Bharat Sridhar, La Jolla, CA (US); Gudrun Stengel, San Diego, CA (US); Christopher Jen-Yue Wei, La Palma, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 399 days.

This patent is subject to a terminal disclaimer.

(21) Appl. No.: 17/486,656

(22) Filed: Sep. 27, 2021

(65) Prior Publication Data

US 2022/0106636 A1   Apr. 7, 2022

Related U.S. Application Data

(63) Continuation of application No. 17/127,514, filed on Dec. 18, 2020, now Pat. No. 11,155,858.

(60) Provisional application No. 62/956,041, filed on Dec. 31, 2019.

(51) Int. Cl.
*C12Q 1/6853* (2018.01)
*C12Q 1/6869* (2018.01)

(52) U.S. Cl.
CPC ......... *C12Q 1/6853* (2013.01); *C12Q 1/6869* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 5,235,033 A | 8/1993 | Summerton et al. |
| 5,302,509 A | 4/1994 | Cheeseman |
| 5,641,658 A | 6/1997 | Adams et al. |
| 5,763,594 A | 6/1998 | Hiatt et al. |
| 5,808,045 A | 9/1998 | Hiatt et al. |
| 5,872,244 A | 2/1999 | Hiatt et al. |

(Continued)

FOREIGN PATENT DOCUMENTS

| | | |
|---|---|---|
| EP | 2 570 487 A1 | 3/2013 |
| WO | WO-96/07669 A1 | 3/1996 |

(Continued)

OTHER PUBLICATIONS

Alkan, C. et al. (May 2011, e-published Mar. 1, 2011). "Genome structural variation discovery and genotyping," *Nat Rev Genet.* 12(5):363-376.

(Continued)

*Primary Examiner* — Young J Kim
(74) *Attorney, Agent, or Firm* — Mintz, Levin, Cohn, Ferris, Glovsky and Popeo, P.C.; Zachary L. Terranova

(57) ABSTRACT

Provided herein are methods of making, amplifying, and sequencing tagged nucleic acid complements, compositions including interposing oligonucleotide barcodes, and kits useful in obtaining long-range sequence data.

18 Claims, 35 Drawing Sheets

Specification includes a Sequence Listing.

(56) References Cited

U.S. PATENT DOCUMENTS

| | | | |
|---|---|---|---|
| 5,925,517 | A | 7/1999 | Tyagi et al. |
| 6,013,445 | A | 1/2000 | Albrecht et al. |
| 6,143,527 | A | 11/2000 | Pachuk et al. |
| 6,232,465 | B1 | 5/2001 | Hiatt et al. |
| 6,255,475 | B1 | 7/2001 | Kwiatkowski |
| 6,335,439 | B1 | 1/2002 | Eleuteri et al. |
| 6,664,079 | B2 | 12/2003 | Ju et al. |
| 7,057,026 | B2 | 6/2006 | Barnes et al. |
| 7,084,125 | B2 | 8/2006 | Wengel |
| 7,115,400 | B1 | 10/2006 | Adessi et al. |
| 7,211,390 | B2 | 5/2007 | Rothberg et al. |
| 7,244,559 | B2 | 7/2007 | Rothberg et al. |
| 7,264,929 | B2 | 9/2007 | Rothberg et al. |
| 7,435,572 | B2 | 10/2008 | Bitinaite |
| 7,541,444 | B2 | 6/2009 | Milton et al. |
| 7,790,418 | B2 | 9/2010 | Mayer |
| 8,003,354 | B2 | 8/2011 | Shen et al. |
| 8,703,461 | B2 | 4/2014 | Peris et al. |
| 8,882,980 | B2 | 11/2014 | Ling et al. |
| 9,328,382 | B2 | 5/2016 | Drmanac et al. |
| 9,416,409 | B2 | 8/2016 | Hayden |
| 9,708,654 | B2 | 7/2017 | Hunicke-Smith et al. |
| 10,392,614 | B2 | 8/2019 | Vigneault et al. |
| 10,392,726 | B2 | 8/2019 | Church et al. |
| 10,428,373 | B2 | 10/2019 | Huang |
| 10,577,603 | B2 | 3/2020 | Steemers et al. |
| 10,738,072 | B1 | 8/2020 | Graham et al. |
| 10,982,278 | B2 | 4/2021 | Xin et al. |
| 11,155,858 | B2 * | 10/2021 | Glezer ............... C12Q 1/6853 |
| 2003/0092905 | A1 | 5/2003 | Kochkine et al. |
| 2008/0009420 | A1 | 1/2008 | Schroth et al. |
| 2013/0012399 | A1 | 1/2013 | Myers et al. |
| 2013/0079231 | A1 | 3/2013 | Pushkarev et al. |
| 2014/0357528 | A1 | 12/2014 | Robb et al. |
| 2015/0152409 | A1 | 6/2015 | Seitz et al. |
| 2016/0046985 | A1 | 2/2016 | Drmanac et al. |
| 2016/0289760 | A1 | 10/2016 | Suzuki et al. |
| 2018/0051277 | A1 | 2/2018 | Godfrey et al. |
| 2018/0258472 | A1 | 9/2018 | Glezer |
| 2018/0274024 | A1 | 9/2018 | Ju et al. |
| 2020/0102609 | A1 | 4/2020 | Glezer et al. |
| 2020/0131484 | A1 | 4/2020 | Golynskiy et al. |
| 2020/0181587 | A1 | 6/2020 | Klausing et al. |
| 2021/0017596 | A1 | 1/2021 | Tong et al. |
| 2021/0164128 | A1 | 6/2021 | Brown et al. |
| 2021/0277461 | A1 | 9/2021 | Glezer et al. |

FOREIGN PATENT DOCUMENTS

| | | | | |
|---|---|---|---|---|
| WO | WO-2004/018497 | A2 | 3/2004 | |
| WO | WO-2004/018497 | A3 | 3/2004 | |
| WO | WO-2014145820 | A2 * | 9/2014 | ........... C12Q 1/6806 |
| WO | WO-2014/145820 | A3 | 11/2014 | |
| WO | WO-2015/073693 | A1 | 5/2015 | |
| WO | WO-2017/156126 | A1 | 9/2017 | |
| WO | WO-2017/205336 | A1 | 11/2017 | |
| WO | WO-2018/148723 | A1 | 8/2018 | |
| WO | WO-2020/056044 | A1 | 3/2020 | |
| WO | WO-2021/138094 | A1 | 7/2021 | |

OTHER PUBLICATIONS

Alneberg, J. et al. (Nov. 2014, e-published Sep. 14, 2014). "Binning metagenomic contigs by coverage and composition," *Nat Methods* 11(11):1144-1146.

Bains, I. et al. (May 28, 2009) "Quantifying the development of the peripheral naive CD4+ T-cell pool in humans," *Blood* 113(22):5480-5487.

Baker G.C. et al. (2003). "Review and re-analysis of domain-specific 16S primers," J Microbiological Methods 55:541-555.

Barkoff, A. et al. (Jun. 1, 1998). "Meiotic maturation in Xenopus requires polyadenylation of multiple mRNAs," *EMBO J.* 17(11): 3168-3175.

Bentley, D.R. et al. (Nov. 6, 2008). "Accurate whole human genome sequencing using reversible terminator chemistry," *Nature* 456(7218):53-59.

Chakravorty, S., et al. (May 2007, e-published Feb. 22, 2007). "A detailed analysis of 16S ribosomal RNA gene segments for the diagnosis of pathogenic bacteria," *J Microbiological Methods* 69(2):330-339.

Dirks, R.M. et al. (Oct. 26, 2004, e-published Oct. 18, 2004). "Triggered amplification by hybridization chain reaction," PNAS USA 101(43):15275-15278.

El-Sagheer, A. H. et al. (Aug. 21, 2012, e-published Mar. 22, 2012). "Click nucleic acid ligation: applications in biology and nanotechnology," *Accounts of Chemical Research* 45(8), 1258-1267.

Fan, T. et al. (Sep. 2018, e-published Aug. 20, 2018). "Branched rolling circle amplification method for measuring serum circulating microRNA levels for early breast cancer detection," *Cancer Sci* 109(9):2897-2906.

Fu, Y. et al. (Jul. 13, 2018). "Elimination of PCR duplicates in RNA-seq and small RNA-seq using unique molecular identifiers," *BMC Genomics* 19(1):531.

Ganusov, V.V. et al. (Dec. 2007, e-published Oct. 26, 2007). "Do most lymphocytes in humans really reside in the gut?" *Trends Immunol.* 28(12):514-518.

Hieronymus, H. et al. (Sep. 4, 2018). "Tumor copy number alteration burden is a pan-cancer prognostic factor associated with recurrence and death," *Elife* 7:e37294.

Hong, J. et al. (Nov. 1, 2017). "Incorporation of unique molecular identifiers in TruSeq adapters improves the accuracy of quantitative sequencing," *Biotechniques* 63(5):221-226.

Howe, A.C. et al. (Apr. 1, 2014, e-published Mar. 14, 2014). "Tackling soil diversity with the assembly of large, complex metagenomes," *PNAS USA* 111(13):4904-4909.

International Search Report mailed on Apr. 26, 2021, for PCT Application No. PCT/US2020/66170, filed Dec. 18, 2020, 7 pages.

Ju, J. et al. (Dec. 26, 2006, e-published Dec. 14, 2006). "Four-color DNA sequencing by synthesis using cleavable fluorescent nucleotide reversible terminators," *PNAS USA* 103(52):19635-19640.

Kivioja, T. et al. (Nov. 20, 2011). "Counting absolute numbers of molecules using unique molecular identifiers," *Nat Methods* 9(1):72-74.

Kou, R et al. (Jan. 11, 2016). "Benefits and Challenges with Applying Unique Molecular Identifiers in Next Generation Sequencing to Detect Low Frequency Mutations," *PLoS One* 11(1):e0146638.

Lage, J.M. et al. (Feb. 2003). "Whole genome analysis of genetic alterations in small DNA samples using hyperbranched strand displacement amplification and array-CGH," *Genome Res* 13(2):294-307.

Lauer, S. et al. (Dec. 2019, e-published May 10, 2019). "An evolving view of copy number variants," *Curr Genet* 65(6):1287-1295.

Lizardi, P.M. et al. (Jul. 1998). "Mutation detection and single-molecule counting using isothermal rolling-circle amplification," *Nat. Genet.* 19(3):225-232.

Manuguerra I. et al. (May 1, 2018). "Gene assembly via one-pot chemical ligation of DNA promoted by DNA nanostructures," *Chem Commun (Camb).* 54(36):4529-4532.

McFarland, K.N. et al. (Aug. 21, 2015). "SMRT Sequencing of Long Tandem Nucleotide Repeats in SCA10 Reveals Unique Insight of Repeat Expansion Structure," *PLos One* 10(8):e0135906.

Moncunili, V. et al. (Nov. 2014, e-published Oct. 26, 2014). "Comprehensive characterization of complex structural variations in cancer by directly comparing genome sequence reads," *Nat. Biotechnol.* 32(11):1106-1112.

Myllykangas, S. et al. (Dec. 14, 2011). "Targeted sequencing library preparation by genomic DNA circularization," *BMC Biotechnology* 11:122.

Nilsson, M. et al. (Sep. 30, 1994). "Padlock probes: circularizing oligonucleotides for localized DNA detection," *Science* 265(5181):2085-2088.

Odeh, F., et al. (Dec. 18, 2019). "Aptamers Chemistry: Chemical Modifications and Conjugation Strategies," *Molecules* 25(1):3.

Pei, B et al. (Sep. 26, 2012). "The GENCODE pseudogene resource," *Genome Biology* 13(9):R51.

(56) References Cited

OTHER PUBLICATIONS

Pflug, F.G. et al. (Sep. 15, 2018). "TRUmiCount: correctly counting absolute numbers of molecules using unique molecular identifiers," *Bioinformatics* 34(18):3137-3144.

Scorilas, A. (Jun. 2002). "Polyadenylate polymerase (PAP) and 3' end pre-mRNA processing: function, assays, and association with disease," Crit Rev Clin Lab Sci 39(3):193-224.

Shlien, A. et al. (Jun. 16, 2009). "Copy number variations and cancer," *Genome Med.* 16:1(6):62.

Smith, T. et al. (Mar. 2017, e-published Jan. 18, 2017). "UMI-tools: modeling sequencing errors in Unique Molecular Identifiers to improve quantification accuracy," *Genome Res* 27(3):491-499.

Snyder, M.W. et al. (Jun. 2015, e-published May 7, 2015). "Haplotype-resolved genome sequencing: experimental methods and applications," *Nat. Rev. Genet.* 16(6):344-358.

Southworth, M.W. et al. (May 28, 1996). "Cloning of thermostable DNA polymerases from hyperthermophilic marine Archaea with emphasis on *Thermococcus* sp. 9°N-7 and mutations affecting 3'-5' exonuclease activity," *PNAS USA* 93(11):5281-5285.

Subtelny, A.O. et al. (Apr. 3, 2014, e-published Jan. 29, 2014). "Poly(A)-tail profiling reveals an embryonic switch in translational control," *Nature* 508(7494)::66-71.

Tang, H et al. (Nov. 2, 2017). "Profiling of Short-Tandem-Repeat Disease Alleles in 12,632 Human Whole Genomes," *Am. J. Hum. Genet.* 101(5):700-715.

Trowsdale, J. et al. (2013, e-published Jul. 15, 2013). "Major histocompatibility complex genomics and human disease," *Annu Rev Genomics Hum Genet.* 14:301-323.

Valsesia, A. et al. (May 30, 2013). "The Growing Importance of CNVs: New Insights for Detection and Clinical Interpretation," *Front Genet.* 4:92.

Voskoboynik, A. et al. (Jul. 2, 2013). "The genome sequence of the colonial chordate, Botryllus schlosseri," *eLife* 2:e00569.

Wang, Y. et al. (Mar. 3, 2014). "Optimal eukaryotic 18S and universal 16S/18S ribosomal RNA primers and their application in a study of symbiosis," *PloS One* 9(3):e90053.

White, R.A. et al. (Jun. 28, 2016). "Moleculo Long-Read Sequencing Facilitates Assembly and Genomic Binning from Complex Soil Metagenomes," *mSystems* 1(3):e00045-16.

Written Opinion mailed on Apr. 26, 2021, for PCT Application No. PCT/US2020/66170, filed Dec. 18, 2020, 15 pages.

Yaari, G. et al. (Nov. 20, 2015). "Practical guidelines for B-cell receptor repertoire sequencing analysis," *Genome Med.* 7:121.

Yamamoto, T. et al. (Aug. 18, 2016). "Challenges in detecting genomic copy number aberrations using next-generation sequencing data and the eXome Hidden Markov Model: a clinical exome-first diagnostic approach," *Hum Genome Var* 3:16025.

Extended European Examination Report mailed on Jul. 3, 2023, for EP Application No. 20909284.0, PCT/US/2020/066170, 7 pages.

International Search Report and Written Opinion mailed on Jun. 8, 2023, for PCT Application No. PCT/US/2023/062437, filed Feb. 10, 2023, 18 pages.

Dekosky, B. J. et al. (Feb. 2013, e-published Jan. 20, 2013). "High-throughput sequencing of the paired human immunoglobulin heavy and light chain repertoire," *Nature biotechnology* 31(2): 166-169.

Devulapally, P. R et al. (Apr. 27, 2018). "Simple paired heavy- and light-chain antibody repertoire sequencing using endoplasmic reticulum microsomes," *Genome Medicine* 10: Article 34, pp. 1-12.

International Search Report and Written Opinion mailed on Nov. 30, 2022, for PCT Application No. PCT/US2022/035022, filed Jun. 24, 2022, 25 pages.

Tanno, H. et al. (Apr. 22, 2020). "A facile technology for the high-throughput sequencing of the paired VH: VL and TCRβ: TCRα repertoires," *Science Advances* 6(17): eaay9093.

Thelwell, N. et al. (Oct. 1, 2000). "Mode of action and application of Scorpion primers to mutation detection," *Nucleic acids research* 28(19): 3752-3761.

Zhelkovsky, A. M. et al. (Nov. 2014). "Polynucleotide 3'-terminal phosphate modifications by RNA and DNA ligases," *Journal of Biological Chemistry* 289(48): 33608-33616.

\* cited by examiner

1. Tag genomic DNA (e.g., biotinylate) & denature

2. Denature, hybridize oligonucleotide barcodes, & immobilize

3. Extend and ligate

4. Elute interpolator strand → To amplification

1. Denature, hybridize biotin-oligonucleotide barcodes, immobilize

2. Extend and ligate, last immobilize

3. Wash away template

To amplification

1. Denature, extend and ligate

2. End-repair and A-tailing

3. Universal adapter ligation

4. PCR amplify

To random fragmentation and traditional library prep

Strand displacement amplification

Hairpin stem priming

Random priming

First strand

Strand Displacement Amplification
(up to 5 – 10kb fragments)

Random Fragmentation &
PCR-free primer library prep

Starting material = unfragmented ss-DNA

Option A: Use RNA as a template for extension/ligation

1. Capture mRNA via polyA tail

2. Hybridize oligonucleotide barcodes, extend/ligate

Option B: Reverse transcribe RNA prior to extension/ligation 1. mRNA capture and reverse transcription Optional: C-tailing 2. Remove RNA, hybridize oligonucleotide barcodes, extend/ligate Ideal: DNA pol stops as it hits 5'P of upstream hairpin Common: DNA pol stops overshoots by 1 base creating non-ligatable 5'flap Optimization by:
Extension & ligation in one pot
Excess ligase
Control reaction times
Lower temp
Non strand displacing pol Alternative: Design hairpin with a 5'flap (no 5'P necessary) and use FEN-1 to generate ligatable nick Cleave here to seal

POLYNUCLEOTIDE BARCODES FOR LONG READ SEQUENCING

CROSS-REFERENCES TO RELATED APPLICATIONS

This application is a continuation of U.S. application Ser. No. 17/127,514, filed Dec. 18, 2020, which claims the benefit of U.S. Provisional Application No. 62/956,041, filed Dec. 31, 2019, each of which is incorporated herein by reference in its entirety and for all purposes.

SEQUENCE LISTING

The instant application contains a Sequence Listing which has been submitted electronically in ASCII format and is hereby incorporated by reference in its entirety. Said ASCII copy, created on Dec. 22, 2021, is named 051385-520C01US_SL_ST25.txt and is 2,893 bytes in size.

BACKGROUND

A number of next-generation sequencing (NGS) platforms are available for the high-throughput, massively parallel sequencing of nucleic acids. Certain NGS sequencing methodologies make use of simultaneously sequencing millions of fragments of nucleic acids, resulting in a 50,000-fold drop in the costs associated with sequencing since its inception. Due to the read lengths of current NGS platforms, ranging in length from 35 to 300 base pairs, nucleic acid sequencing technologies may struggle with accurately mapping sequences having large structural variations, e.g., inversions and translocations, tandem repeat regions, distinguishing clinically relevant genes from pseudogenes, and haplotype reconstructions.

SUMMARY

In view of the foregoing, innovative approaches to address issues with existing sequencing technologies are needed. Disclosed herein are solutions to these and other problems in the art.

In an aspect is provided a method of amplifying tagged complements of a plurality of sample polynucleotides, the method including: (a) hybridizing to each of the plurality of sample polynucleotides a plurality of interposing oligonucleotide barcodes, each of the interposing oligonucleotide barcodes including from 5' to 3': (i) a first hybridization pad complementary to a first sequence of a sample polynucleotide; (ii) a first stem region comprising a sequence common to the plurality of interposing oligonucleotide barcodes; (iii) a loop region comprising a barcode sequence, wherein the barcode sequence, alone or in combination with a sequence of one or both of (a) the sample polynucleotide, or (b) one or more additional barcode sequences, uniquely distinguishes the sample polynucleotide from other sample polynucleotides in the plurality; (iii) a second stem region comprising a sequence complementary to the first stem region, wherein the second stem region is capable of hybridizing to the first stem region under hybridization conditions; and (iv) a second hybridization pad complementary to a second sequence of the sample polynucleotide; extending the 3' ends of the second hybridization pads with one or more polymerases to create extension products; and ligating adjacent ends of extension products hybridized to the same sample polynucleotide thereby making integrated strands comprising complements of the plurality of sample polynucleotides tagged with a plurality of interposing oligonucleotide barcodes; and amplifying the integrated strands by an amplification reaction thereby amplifying the tagged complements of the plurality of sample polynucleotides. In embodiments, the method further includes sequencing the amplified products.

In an aspect, provided herein are methods of making tagged complements of a plurality of sample polynucleotides. The methods include (a) hybridizing to each of the plurality of sample polynucleotides a plurality of interposing oligonucleotide barcodes (also simply, "interposing barcodes" or IBCs); (b) extending the 3' ends of the interposing oligonucleotide barcodes with one or more polymerases to create extension products; and (c) ligating adjacent ends of extension products hybridized to the same sample polynucleotide thereby making complements of the plurality of sample polynucleotides tagged with a plurality of interposing oligonucleotide barcodes. In embodiments, each of the interposing oligonucleotide barcodes include from 5' to 3': (i) a first hybridization pad complementary to a first sequence of a sample polynucleotide; (ii) a first stem region including a sequence common to the plurality of interposing oligonucleotide barcodes; (iii) a loop region including a barcode sequence, where the barcode sequence, alone or in combination with a sequence of one or both of (a) the sample polynucleotide, or (b) one or more additional barcode sequences, uniquely distinguishes the sample polynucleotide from other sample polynucleotides in the plurality; (iv) a second stem region including a sequence complementary to the first stem region, where the second stem region is capable of hybridizing to the first stem region under hybridization conditions; and (v) a second hybridization pad complementary to a second sequence of the sample polynucleotide.

In an aspect, provided herein are interposing oligonucleotide barcodes that include from 5' to 3': (i) a first hybridization pad complementary to a first sequence of a sample polynucleotide; (ii) a first stem region including a sequence common to the plurality of interposing oligonucleotide barcodes; (iii) a loop region including a barcode sequence, where the barcode sequence, alone or in combination with a sequence of one or both of (a) the sample polynucleotide, or (b) one or more additional barcode sequences, uniquely distinguishes the sample polynucleotide from other sample polynucleotides in the plurality; (iv) a second stem region including a sequence complementary to the first stem region, where the second stem region is capable of hybridizing to the first stem region under hybridization conditions; and (v) a second hybridization pad complementary to a second sequence of the sample polynucleotide.

In an aspect, provided herein are polynucleotides including a plurality of units, where each unit includes a portion of a genomic sequence and a sequence of an interposing oligonucleotide barcode. In embodiments, each interposing oligonucleotide barcode includes from 5' to 3': (a) a first stem region including a sequence common to the plurality of units; (b) a loop region including a barcode sequence, wherein each barcode sequence in the polynucleotide is different; and (c) a second stem region including a sequence complementary to the first stem region, where the second stem region hybridizes to the first stem region during the hybridizing.

In an aspect, provided herein are kits including a plurality of interposing oligonucleotide barcodes that include from 5' to 3': (a) a first stem region including a sequence common to the plurality of interposing oligonucleotide barcodes; (b) a loop region including a barcode sequence, wherein each barcode sequence in the polynucleotide is different; and (c) a second stem region including a sequence complementary to the first stem region, where the second stem region hybridizes to the first stem region during said hybridizing.

BRIEF DESCRIPTION OF THE DRAWINGS

FIG. 1A is an overview of a non-limiting example of an interposing barcode showing Type 1 and Type 2 IBCs, wherein Type 2 includes an additional identifying region (e.g., sample barcode, such as a 4 to 5 nucleotide section used to identify the sample, also referred to as a "sample index sequence"). Depending on the experiment, both Type 1 and Type 2 may be used. FIG. 1B shows an interposing barcode subjected to denaturing conditions (i.e. the stem regions are no longer hybridized together).

FIG. 2A depicts a single strand genomic DNA, to which a plurality of interposing barcodes are hybridized. A polymerase extends (depicted as the gray, cloud-like, structure) from the 3' end of an interposing barcode and halts extension at or around the next interposing barcode. Dashed lines represent yet-to-be extension sites. A ligase (not shown) then ligates the extension strands and interposing barcodes together to produce a long, continuous DNA strand which contains integrated barcodes, as shown in FIG. 2B. When the hairpins stems are not hybridized together, the resultant single strand is shown in FIG. 2C. Note, the shading used in the figures is not indicative of an identical sequence. For example, although the loops depicted in FIG. 2A are rendered in the same color/shading, this does not imply the sequences of the loops are identical. In embodiments, the only sequences that are common are the stems of the interposing barcodes.

DETAILED DESCRIPTION

Figure 1A:
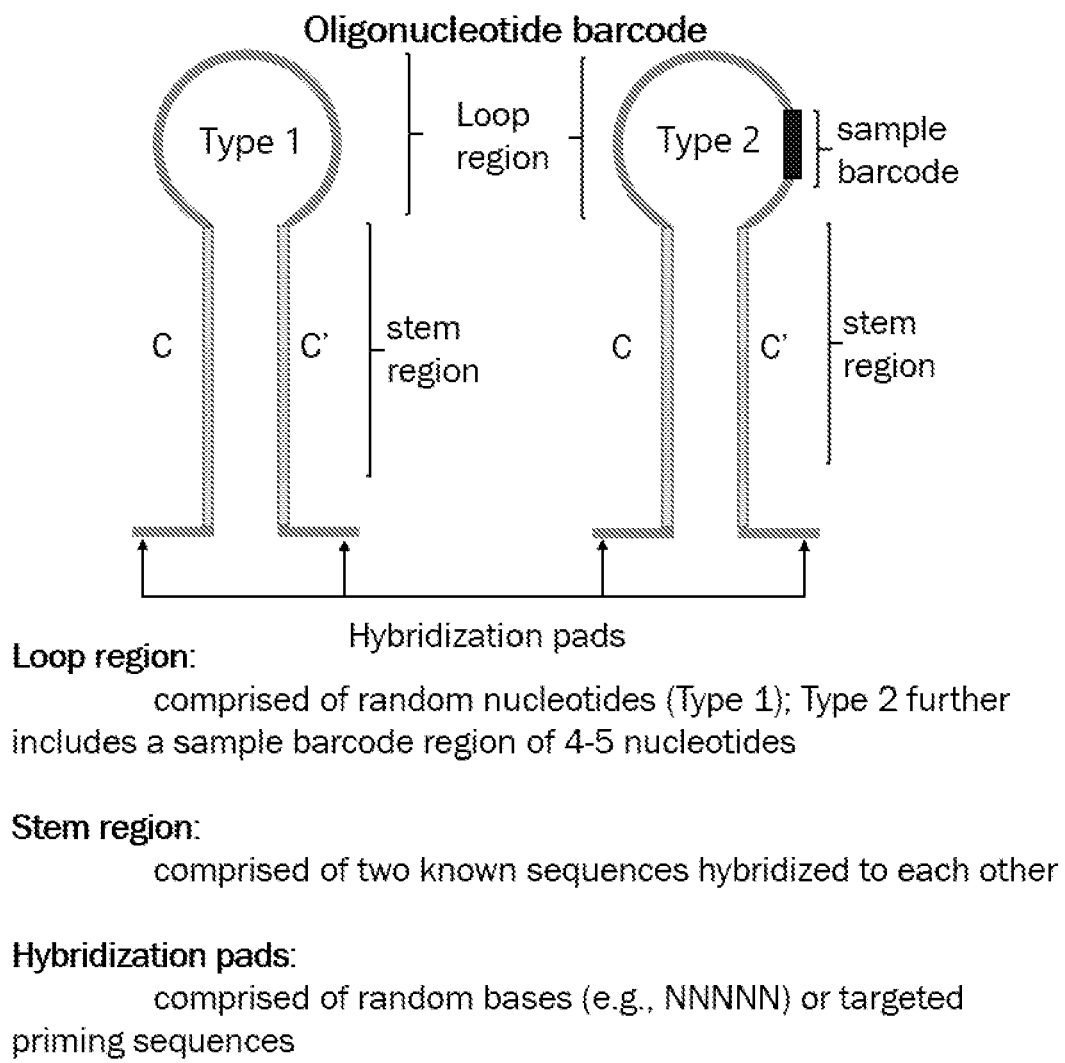
FIGS. 1A-1B illustrate interposing barcodes (IBC) as described herein.

Described herein are compositions and methods for mapping sequences, which are especially useful for sequences having large structural variations, e.g., inversions and translocations, tandem repeat regions, distinguishing clinically relevant genes from pseudogenes, and haplotype reconstructions.

The practice of the technology described herein will employ, unless indicated specifically to the contrary, conventional methods of chemistry, biochemistry, organic chemistry, molecular biology, recombinant DNA techniques, genetics, immunology, and cell biology that are within the skill of the art, many of which are described below for the purpose of illustration. Examples of such techniques are available in the literature. Methods, devices, and materials similar or equivalent to those described herein can be used in the practice of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise.

Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term "contacting" is used in accordance with its plain ordinary meaning and refers to the process of allowing at least two distinct species (e.g. chemical compounds including biomolecules or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, nucleic acid, a protein, or enzyme (e.g., a DNA polymerase).

As used herein, the term "nucleic acid" is used in accordance with its plain and ordinary meaning and refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. A "nucleoside" is structurally similar to a nucleotide, but is missing the phosphate moieties. An example of a nucleoside analogue would be one in which the label is linked to the base and there is no phosphate group attached to the sugar molecule. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the term "template nucleic acid" refers to any polynucleotide molecule that may be bound by a polymerase and utilized as a template for nucleic acid synthesis. A template nucleic acid may be a target nucleic acid. In general, the term "target nucleic acid" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target nucleic acid is not necessarily any single molecule or sequence. For example, a target nucleic acid may be any one of a plurality of target nucleic acids in a reaction, or all nucleic acids in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target nucleic acid in a reaction with the corresponding primer polynucleotide(s). In the context of selective sequencing, "target nucleic acid(s)" refers to the subset of nucleic acid(s) to be sequenced from within a starting population of nucleic acids.

In embodiments, a target nucleic acid is a cell-free nucleic acid. In general, the terms "cell-free," "circulating," and "extracellular" as applied to nucleic acids (e.g. "cell-free DNA" (cfDNA) and "cell-free RNA" (cfRNA)) are used interchangeably to refer to nucleic acids present in a sample from a subject or portion thereof that can be isolated or otherwise manipulated without applying a lysis step to the sample as originally collected (e.g., as in extraction from cells or viruses). Cell-free nucleic acids are thus unencapsulated or "free" from the cells or viruses from which they originate, even before a sample of the subject is collected. Cell-free nucleic acids may be produced as a byproduct of cell death (e.g. apoptosis or necrosis) or cell shedding, releasing nucleic acids into surrounding body fluids or into circulation. Accordingly, cell-free nucleic acids may be isolated from a non-cellular fraction of blood (e.g. serum or plasma), from other bodily fluids (e.g. urine), or from non-cellular fractions of other types of samples.

The term "messenger RNA" or "mRNA" refers to an RNA that is without introns and is capable of being translated into a polypeptide. The term "RNA" refers to any ribonucleic acid, including but not limited to mRNA, tRNA (transfer RNA), rRNA (ribosomal RNA), and/or noncoding RNA (such as lncRNA (long noncoding RNA)). The term "cDNA" refers to a DNA that is complementary or identical to an RNA, in either single stranded or double stranded form.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds.) Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety (alternatively referred to herein as a reversible terminator moiety) and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —NH$_2$, —CN, —CH$_3$, C$_2$-C$_6$ allyl (e.g., —CH$_2$—CH═CH$_2$), methoxyalkyl (e.g., —CH$_2$—O—CH$_3$), or —CH$_2$N$_3$. In embodiments, the blocking moiety is attached to the 3' oxygen of the nucleotide and is independently

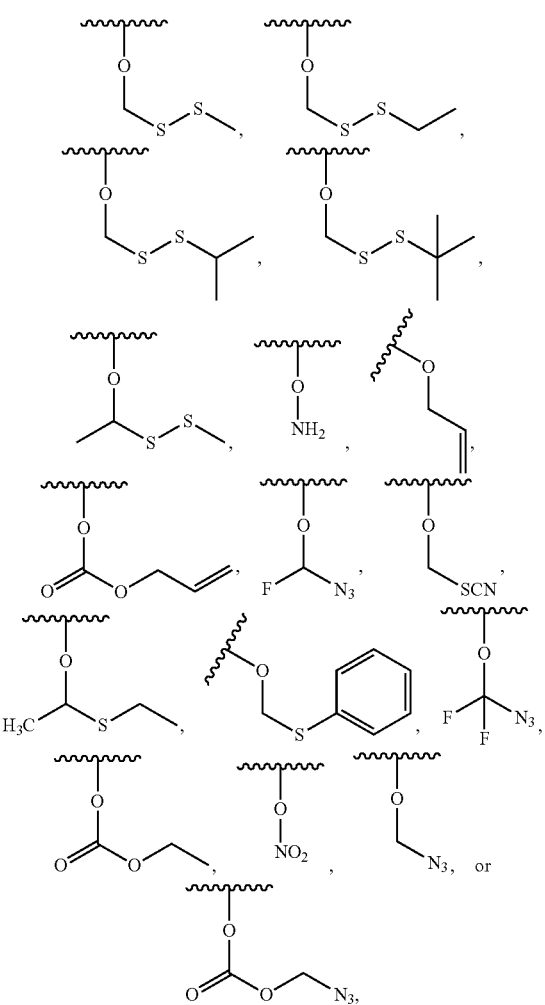

wherein the 3' oxygen is explicitly depicted. A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the —OH group at the 3'-position of deoxyribose. Nucleotide analogues and DNA polymerase-based DNA sequencing are also described in U.S. Pat. No. 6,664,079, which is incorporated herein by reference in its entirety for all purposes.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite (Na$_2$S$_2$O$_4$), or hydrazine (N$_2$H$_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite (Na$_2$S$_2$O$_4$), weak acid, hydrazine (N$_2$H$_4$), Pd(0), or light-irradiation (e.g., ultraviolet radiation).

As used herein, the term "complement" is used in accordance with its plain and ordinary meaning and refers to a nucleotide (e.g., RNA nucleotide or DNA nucleotide) or a sequence of nucleotides capable of base pairing with a complementary nucleotide or sequence of nucleotides. As described herein and commonly known in the art the complementary (matching) nucleotide of adenosine is thymidine in DNA, or alternatively in RNA the complementary (matching) nucleotide of adenosine is uracil, and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. The pairing of purine containing nucleotide (e.g., A or G) with a pyrimidine containing nucleotide (e.g., T or C) are considered complements. The A-T and C-G pairings function to form double or triple hydrogen bonds between the amine and carbonyl groups on the complementary bases.

As described herein, the complementarity of sequences may be partial, in which only some of the nucleic acids match according to base pairing, or complete, where all nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin structure, with or without an overhang) or portions of separate polynucleotides. In embodiments, one or both sequences in a pair of complementary sequences form portions of longer polynucleotides, which may or may not include additional regions of complementarity.

As used herein, the terms "hybridization" and "hybridizing" refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi-stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is perfectly complementary to a first sequence, or is polymerized by a polymerase using the first sequence as template, is referred to as "the complement" of the first sequence. The term "hybridizable" as applied to a polynucleotide refers to the ability of the polynucleotide to form a complex that is stabilized via hydrogen bonding between the bases of the nucleotide residues in a hybridization reaction. In some embodiments, a hybridizable sequence of nucleotides is at least about 50%, 60%, 70%, 75%, 80%, 85%, 90%, 95%, or 100% complementary to the sequence to which it hybridizes. In some embodiments, a hybridizable sequence is one that hybridizes to one or more target sequences as part of, and under the conditions of, a step in a multi-step process (e.g., a ligation reaction, or an amplification reaction). The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can further altered by the addition or removal of components of the buffered solution. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which comprises a double-stranded portion of nucleic acid. The terms "hybridize" and "anneal", and grammatical variations thereof, are used interchangeably herein. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence.

As used herein, the term "label" or "labels" is used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiments, a nucleotide comprises a label (such as a dye). In embodiments, the label is not associated with any particular nucleotide, but detection of the label identifies whether one or more nucleotides having a known identity were added during an extension step (such as in the case of pyrosequencing).

In embodiments, the detectable label is a fluorescent dye. In embodiments, the detectable label is a fluorescent dye capable of exchanging energy with another fluorescent dye (e.g., fluorescence resonance energy transfer (FRET) chromophores).

As used herein, the term "polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, *E. Coli* DNA polymerase I, Bacteriophage T4 DNA polymerase, Sequenase, Taq DNA polymerase, DNA polymerase from *Bacillus stearothermophilus*, Bst 2.0 DNA polymerase, 9° N polymerase (exo-)A485L/Y409V, Phi29 DNA Polymerase ((φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol τ DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g. Therminator γ, 9° N polymerase (exo-), Therminator™ II, Therminator™ III, or Therminator™ IX). In embodiments, the DNA polymerase is a modified archaeal DNA polymerase. In embodiments, the polymerase is a reverse transcriptase. In embodiments, the polymerase is a mutant P. abyssi polymerase (e.g., such as a mutant P. abyssi polymerase described in WO 2018/148723 or WO 2020/056044). In embodiments, the polymerase is a reverse transcriptase such as HIV type M or O reverse transcriptase, avian myeloblastosis virus reverse transcriptase, or Moloney Murine Leukemia Virus (MMLV) reverse transcriptase, or telomerase.

The terms "DNA ligase" and "ligase" are used in accordance with their ordinary meaning in the art and refer to an enzyme capable catalyzing the formation of a phosphodiester bond between two nucleic acids. In embodiments, the DNA ligase covalently joins the phosphate backbone of a nucleic acid with a compatible nucleotide residue (e.g., a second blunt ended strand). In embodiments, the ligase is a ligation enzyme (e.g., CircLigase™ enzyme, Taq DNA Ligase, HiFi Taq DNA Ligase, T4 ligase, PBCV-1 DNA Ligase (also known as SplintR ligase) or Ampligase DNA Ligase). Non-limiting examples of ligases include DNA ligases such as DNA Ligase I, DNA Ligase II, DNA Ligase III, DNA Ligase IV, T4 DNA ligase, T7 DNA ligase, T3 DNA Ligase, E. coli DNA Ligase, PBCV-1 DNA Ligase (also known as SplintR ligase) or a Taq DNA Ligase. In embodiments, a ligase is provided in a buffer containing ATP and a divalent ion (e.g., $Mn^{2+}$ or $Mg^{2+}$). In embodiments, the ligase is provided in a buffer containing PEG, which is known to increase the ligation efficiency of nucleic acid molecules. As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of a primer or extension strand. Occasionally, a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer or extension product as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at either the 3' end of a polynucleotide chain to excise the nucleotide. In embodiments, 3 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, for example Southworth et al. PNAS Vol 93, 8281-8285 (1996).

As used herein, the term "selective" or "selectivity" is used in accordance with its ordinary meaning in the art, and in the context of a compound refers to a compound's ability to discriminate between molecular targets.

As used herein, the terms "specific", "specifically", and "specificity", are used in accordance with their ordinary meaning in the art, and in the context of a compound refer to the compound's ability to cause a particular action, such as binding, to a particular molecular target with minimal or no action to other proteins in the cell.

As used herein, the terms "bind" and "bound" are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) DNA strand.

As used herein, the term "hybridization pad" refers to one or both of two regions on either end of an interposing oligonucleotide barcode that are capable of hybridizing to single-stranded template nucleic acids. In embodiments, hybridization pads are a complement to the original target nucleic acid. In embodiments, each hybridization pad is composed of about 3 to about 40 random nucleotides (e.g. NNNNN, wherein N represents A, T, C, G nucleotides). In embodiments, each hybridization pad is composed of about 3 to about 5 random nucleotides. In embodiments, the first hybridization pad includes about 3 to about 5 nucleotides (e.g., random nucleotides) and the second hybridization pad includes about 3 to 25 nucleotides (e.g., random nucleotides). In embodiments, the first hybridization pad includes about 5 to about 15 nucleotides (e.g., random nucleotides) and the second hybridization pad includes about 5 to 15 nucleotides (e.g., random nucleotides). In embodiments, the first hybridization pad includes about 10 to about 15 nucleotides (e.g., random nucleotides) and the second hybridization pad includes about 10 to 15 nucleotides (e.g., random nucleotides). In embodiments, the hybridization pad includes a targeted primer sequence, or a portion thereof. A "targeted primer sequence" refers to a nucleic acid sequence that is complementary to a known nucleic acid region (e.g., complementary to a universally conserved region, or complementary sequences to target specific genes or mutations that have relevancy to a particular cancer phenotype). The hybridization pads may include sequences designed through computational software, e.g., Primer BLAST, LaserGene (DNAStar), Oligo (National Biosciences, Inc.), MacVector (Kodak/IBI) or the GCG suite of programs to optimize desired properties. In embodiments, the hybridization pad includes a limited-diversity sequence. A "limited-diversity sequence" refers to a nucleic acid sequence that includes random nucleotide regions and fixed nucleotide regions (e.g., NNANN, ANNTN, TNCNA, etc., wherein N represents random nucleotides and A, T, C, G represent fixed nucleotides). In embodiments, each hybridization pad is composed of 3 random nucleotides and 1 to 2 non-random nucleotides. In embodiments, each hybridization pad is composed of 4 random nucleotides and 1 to 2 non-random nucleotides.

As used herein, the term "stem region" or "stem" refers to a region of an interposing oligonucleotide barcode that includes two known sequences capable of hybridizing to each other. In embodiments, the stem includes about 5 to about 10 nucleotides, and is stable (i.e., capable to remaining hybridized together) at approximately 37° C., and unhybridizes (i.e., denatures) at temperatures greater than 50° C. As the stem is of known or pre-determined sequence (i.e., non-random sequence), the stem sequences allow for location identification of interposing oligonucleotide barcodes. In embodiments, the stem region includes two regions of the same strand that are complementary separated by a loop region; see for example FIG. 1A.

As used herein, the term "loop region" or "loop" refers to a region of an interposing oligonucleotide barcode that is between sequences of the stem region, and remains single-stranded when sequences of the stem region are hybridized to one another. In embodiments, the loop includes about 10 to about 20 random nucleotides. In embodiments, the loop includes a modified nucleotide (e.g., a nucleotide linked to an affinity tag). In embodiments, the loop includes a biotinylated nucleotide (e.g., biotin-11-cytidine-5'-triphosphate). In embodiments, the loop region includes a barcode sequence. See, for example, FIG. 1A. In embodiments, the loop includes a limited-diversity sequence. For example, in embodiments, the loop includes a TT-[UMI]-TT sequence, such as TT-[NNNNNNNNNNNN]-TT (SEQ ID NO:11) sequence, wherein N represents random nucleotides and A, T, C, G represent fixed nucleotides).

As used herein, the term "barcode sequence" (which may be referred to as a "tag," a "molecular barcode," a "molecular identifier," an "identifier sequence," or a "unique molecular identifier") refers to any material (e.g., a nucleotide sequence, a nucleic acid molecule feature) that is capable of distinguishing an individual molecule in a large heterogeneous population of molecules. Generally, a barcode sequence is unique in a pool of barcode sequences that differ from one another in sequence, or is uniquely associated with a particular sample polynucleotide in a pool of sample polynucleotides. In embodiments, the barcode sequence is a nucleotide sequence that forms a portion of a larger polynucleotide, such as an "interposing oligonucleotide barcode" (also referred to herein as an "interposing barcode" or an "oligonucleotide barcode"). In embodiments, every barcode sequence in a pool of interposing oligonucleotide barcodes is unique, such that sequencing reads comprising the barcode sequence can be identified as originating from a single sample polynucleotide molecule on the basis of the barcode sequence alone. In other embodiments, individual barcode sequences may be used more than once, but interposing oligonucleotide barcodes comprising the duplicate barcode sequences hybridize to different sample polynucleotides and/or in different arrangements of neighboring interposing oligonucleotide barcodes, such that sequence reads may still be uniquely distinguished as originating from a single sample polynucleotide molecule on the basis of a barcode sequence and adjacent sequence information (e.g., sample polynucleotide sequence, and/or one or more adjacent barcode sequences). In embodiments, barcode sequences are about or at least about 5, 6, 7, 8, 9, 10, 15, 20, 25, 30, 40, 50, 75 or more nucleotides in length. In embodiments, barcode sequences are shorter than 20, 15, 10, 9, 8, 7, 6, or 5 nucleotides in length. In embodiments, barcode sequences are about 10 to about 50 nucleotides in length, such as about 15 to about 40 or about 20 to about 30 nucleotides in length. In a pool of different barcode sequences, barcode sequences may have the same or different lengths. In general, barcode sequences are of sufficient length and include sequences that are sufficiently different to allow the identification of sequencing reads that originate from the same sample polynucleotide molecule. In embodiments, each barcode sequence in a plurality of barcode sequences differs from every other barcode sequence in the plurality by at least three nucleotide positions, such as at least 3, 4, 5, 6, 7, 8, 9, 10, or more nucleotide positions. In some embodiments, substantially degenerate barcode sequences may be known as random. In some embodiments, a barcode sequence may include a nucleic acid sequence from within a pool of known sequences. In some embodiments, the barcode sequences may be pre-defined.

As used herein, the term "random" in the context of a nucleic acid sequence or barcode sequence refers to a sequence where one or more nucleotides has an equal probability of being present. In embodiments, one or more nucleotides is selected at random from a set of two or more different nucleotides at one or more positions, with each of the different nucleotides selected at one or more positions represented in a pool of oligonucleotides including the random sequence. For example, a random sequence may be represented by a sequence composed of N's, where N can be any nucleotide (e.g., A, T, C, or G). For example, a four base random sequence may have the sequence NNNN, where the Ns can independently be any nucleotide (e.g., AATC). IBCs that contain a random sequence, collectively, have sequences composed of Ns within the hybridization pads, stem region, or loop region. Further, the IBCs have barcode sequences that may contain random sequence. In embodiments, a pool of IBCs may be represented by a fully random sequence, with the caveat that certain sequences have been excluded (e.g., runs of three or more nucleotides of the same type, such as "AAA" or "GGG"). In embodiments, nucleotide positions that are allowed to vary (e.g., by two, three, or four nucleotides) may be separated by one or more fixed positions (e.g., as in "NGN").

As used herein, the terms "solid support" and "substrate" and "solid surface" refer to discrete solid or semi-solid surfaces to which a plurality of primers may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. Solid supports in the form of discrete particles may be referred to herein as "beads," which alone does not imply or require any particular shape. A bead can be non-spherical in shape. A solid support may further comprise a polymer or hydrogel on the surface to which the primers are attached (e.g., the splint primers are covalently attached to the polymer, wherein the polymer is in direct contact with the solid support). Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid supports for some embodiments have at least one surface located within a flow cell. The solid support, or regions thereof, can be substantially flat. The solid support can have surface features such as wells, pits, channels, ridges, raised regions, pegs, posts or the like. The term solid support is encompassing of a substrate (e.g., a flow cell) having a surface comprising a polymer coating covalently attached thereto. In embodiments, the solid support is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008).

As used herein, the terms "sequencing", "sequence determination", and "determining a nucleotide sequence", are used in accordance with their ordinary meaning in the art, and refer to determination of partial as well as full sequence information of the polynucleotide being sequenced, and particular physical processes for generating such sequence information. That is, the term includes sequence comparisons, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. Sequencing methods, such as those outlined in U.S. Pat. No. 5,302,509 can be carried out using the nucleotides described herein. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

As used herein, the terms "blocking moiety" and "reversible blocking group" and "reversible terminator" and "reversible terminator moiety" are used in accordance with their plain and ordinary meanings and refers to a cleavable moiety which does not interfere with the function of a polymerase (e.g., DNA polymerase, modified DNA polymerase). For example, a reversible terminator may refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Suitable nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabelled. The nucleotides may be modified with reversible terminators useful in methods provided herein and may be 3'-O-blocked reversible or 3'-unblocked reversible terminators. In nucleotides with 3'-O-blocked reversible terminators, the blocking group may be represented as —OR [reversible terminating (capping) group], wherein O is the oxygen atom of the 3'-OH of the pentose and R is the blocking group, while the label is linked to the base, which acts as a reporter and can be cleaved. The 3'-O-blocked reversible terminators are known in the art, and may be, for instance, a 3'-ONH$_2$ reversible terminator, a 3'-O-allyl reversible terminator, or a 3'-O-azidomethyl reversible terminator. In embodiments, the reversible terminator moiety is

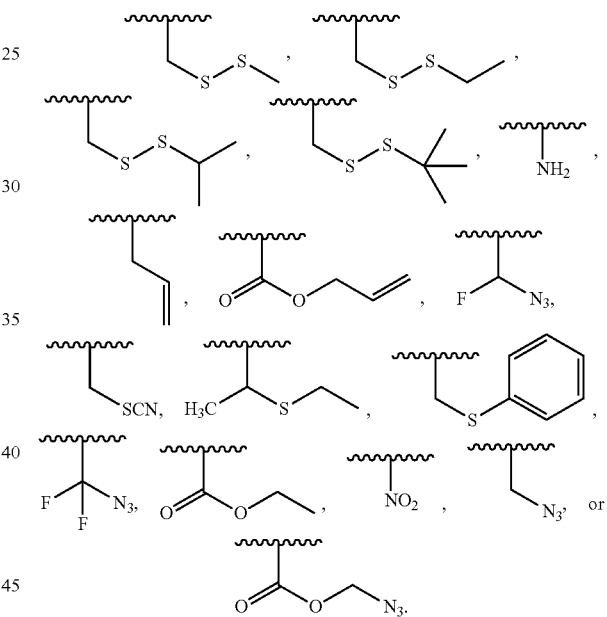

The term "allyl" as described herein refers to an unsubstituted methylene attached to a vinyl group (i.e., —CH=CH$_2$), having the formula

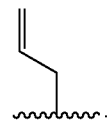

In embodiments, the reversible terminator moiety is,

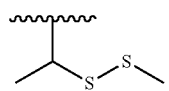

as described in U.S. Pat. No. 10,738,072, which is incorporated herein by reference for all purposes. For example, a nucleotide including a reversible terminator moiety may be represented by the formula:

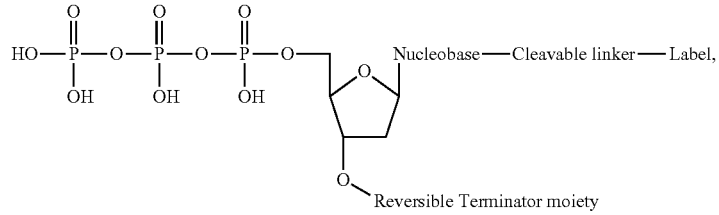

where the nucleobase is adenine or adenine analogue, thymine or thymine analogue, guanine or guanine analogue, or cytosine or cytosine analogue.

Provided herein are methods and compositions for analyzing a sample (e.g., sequencing nucleic acids within a sample). A sample (e.g., a sample comprising nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid).

In some embodiments, a sample comprises nucleic acid, or fragments thereof. A sample can comprise nucleic acids obtained from one or more subjects. In some embodiments a sample comprises nucleic acid obtained from a single subject. In some embodiments, a sample comprises a mixture of nucleic acids. A mixture of nucleic acids can comprise two or more nucleic acid species having different nucleotide sequences, different fragment lengths, different origins (e.g., genomic origins, cell or tissue origins, subject origins, the like or combinations thereof), or combinations thereof. A sample may comprise synthetic nucleic acid.

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits. In embodiments, the kit includes vessels containing one or more enzymes, primers, adaptors, or other reagents as described herein. Vessels may include any structure capable of supporting or containing a liquid or solid material and may include, tubes, vials, jars, containers, tips, etc. In embodiments, a wall of a vessel may permit the transmission of light through the wall. In embodiments, the vessel may be optically clear. The kit may include the enzyme and/or nucleotides in a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer.

The term "primer," as used herein, is defined to be one or more nucleic acid fragments that specifically hybridize to a nucleic acid template. A primer can be of any length depending on the particular technique it will be used for. For example, PCR primers are generally between 10 and 40 nucleotides in length. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. The length and complexity of the nucleic acid fixed onto the nucleic acid template is not critical to the invention. One of skill can adjust these factors to provide optimum hybridization and signal production for a given hybridization procedure, and to provide the required resolution among different genes or genomic locations. The primer permits the addition of a nucleotide residue thereto, or oligonucleotide or polynucleotide synthesis therefrom, under suitable conditions well-known in the art. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. A primer (a primer sequence) is a short, usually chemically synthesized oligonucleotide, of appropriate length, for example about 18-24 bases, sufficient to hybridize to a target nucleic acid (e.g. a single stranded nucleic acid) and permit the addition of a nucleotide residue thereto, or oligonucleotide or polynucleotide synthesis therefrom, under suitable conditions well-known in the art. In an embodiment the primer is a DNA primer, i.e. a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In embodiments the primer is an RNA primer. In embodiments, the primer is an amplification primer (e.g., a primer optimized for PCR amplification which can anneal with the ssDNA and serve as a binding site for a DNA polymerase). The melting temperature (Tm) of a primer can be modified (e.g., increased) to a desired Tm using a suitable method, for example by changing (e.g., increasing) GC content, changing (e.g., increasing) length and/or by the inclusion of modified nucleotides, nucleotide analogues and/or modified nucleotides bonds, non-limiting examples of which include locked nucleic acids (LNAs, e.g., bicyclic nucleic acids), bridged nucleic acids (BNAs, e.g., constrained nucleic acids), C5-modified pyrimidine bases (for example, 5-methyl-dC, propynyl pyrimidines, among others) and alternate backbone chemistries, for example peptide nucleic acids (PNAs), morpholinos, the like or combinations thereof. In embodiments, the primers include nucleotide analogues to increase binding stability (e.g., Locked Nucleic Acid bases (LNAs), 2' fluoronucleotides, or PNAs). For example, a primer that includes synthetic analogue bases such as LNAs (e.g., LNAs as described in US 2003/0092905; U.S. Pat. No. 7,084,125, which are incorporated herein by reference for all purposes) may increase the Tm.

The Tm can be increased by using intercalators or additives such as Ethidium bromide or SYBR Green I. In embodiments, the primer includes a plurality of LNAs (e.g., 2, 3, 4, 5, 6, 7, 8, 9, or 10 LNAs). In embodiments, the primer includes 2-6 LNAs. The ribose moiety of an LNA nucleotide is modified from a typical ribose ring structure by a methylene bridge that connects the 2' oxygen atom and the 4' carbon atom, and which locks the ribose in the 3'endo conformation. Such LNAs can comprise any natural purine or pyrimidine base or non-natural bases (e.g., inosine, chemically modified bases, etc.).

As used herein, the term "sequencing read" is used in accordance with its plain and ordinary meaning and refers to an inferred sequence of base pairs (or base pair probabilities) corresponding to all or part of a single DNA fragment. Sequencing technologies vary in the length of reads produced. Reads of length 20-40 base pairs (bp) are referred to as ultra-short. Typical sequencers produce read lengths in the range of 100-500 bp. A sequencing read may include 10, 20, 30, 40, 50, 60, 70, 80, 90, 100, 150, 200, 250, or more nucleotide bases. Read length is a factor which can affect the results of biological studies. For example, longer read lengths improve the resolution of de novo genome assembly and detection of structural variants.

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

As used herein the term "determine" can be used to refer to the act of ascertaining, establishing or estimating. A determination can be probabilistic. For example, a determination can have an apparent likelihood of at least 50%, 75%, 90%, 95%, 98%, 99%, 99.9% or higher. In some cases, a determination can have an apparent likelihood of 100%. An exemplary determination is a maximum likelihood analysis or report. As used herein, the term "identify," when used in reference to a thing, can be used to refer to recognition of the thing, distinction of the thing from at least one other thing or categorization of the thing with at least one other thing. The recognition, distinction or categorization can be probabilistic. For example, a thing can be identified with an apparent likelihood of at least 50%, 75%, 90%, 95%, 98%, 99%, 99.9% or higher. A thing can be identified based on a result of a maximum likelihood analysis. In some cases, a thing can be identified with an apparent likelihood of 100%.

A "gene" refers to a polynucleotide that is capable of conferring biological function after being transcribed and/or translated.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Interposing Oligonucleotide Barcodes

In an aspect, provided herein are interposing oligonucleotide barcodes that include from 5' to 3': (i) a first hybridization pad complementary to a first sequence of a sample polynucleotide; (ii) a first stem region including a sequence common to the plurality of interposing oligonucleotide barcodes; (iii) a loop region; (iv) a second stem region including a sequence complementary to the first stem region, where the second stem region is capable of hybridizing to the first stem region under hybridization conditions; and (v) a second hybridization pad complementary to a second sequence of the sample polynucleotide. In embodiments, the interposing oligonucleotide barcodes include from 5' to 3': (i) a first hybridization pad complementary to a first sequence of a sample polynucleotide; (ii) a first stem region including a sequence common to the plurality of interposing oligonucleotide barcodes; (iii) a loop region including a barcode sequence, where the barcode sequence, alone or in combination with a sequence of one or both of (a) the sample polynucleotide, or (b) one or more additional barcode sequences, uniquely distinguishes the sample polynucleotide from other sample polynucleotides in the plurality; (iv) a second stem region including a sequence complementary to the first stem region, where the second stem region is capable of hybridizing to the first stem region under hybridization conditions; and (v) a second hybridization pad complementary to a second sequence of the sample polynucleotide.

Figure 4:
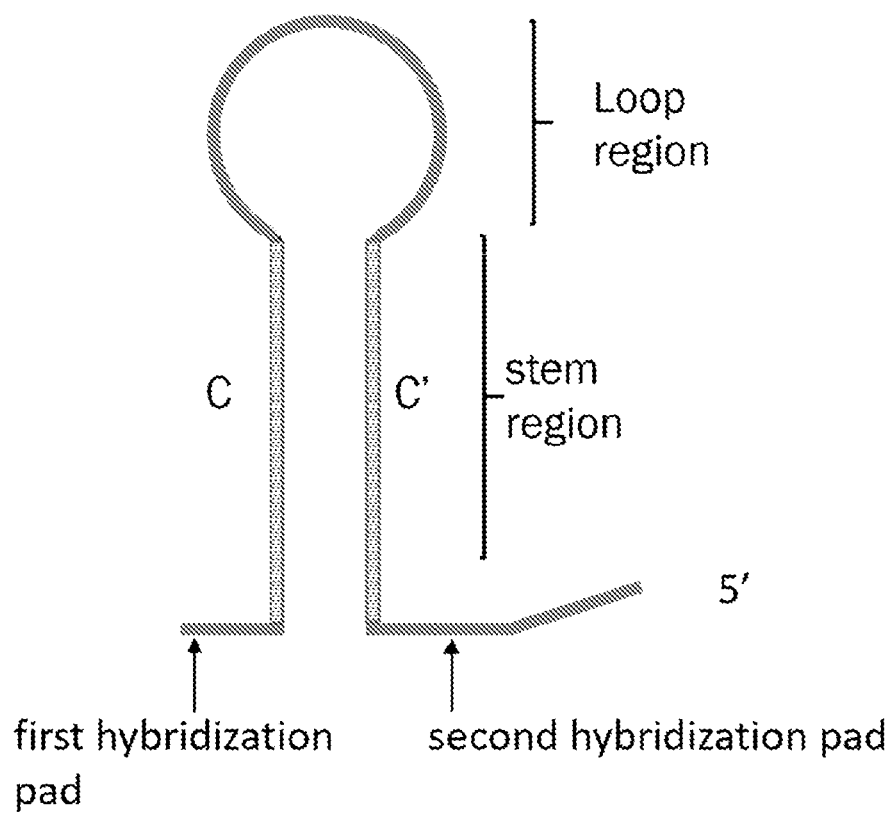
FIG. 4 illustrates an alternative IBC wherein the hybridization pads are asymmetric. As described further within the application, the 5' hybridization pad is elongated relative to the 3' hybridization pad possessing a 5' flap (the raised portion of the hybridization pad) for use with FEN1 (see FIG. 9 for additional details). This IBC may be Type 1 or Type 2, though the additional barcode is not shown in this depiction.

In embodiments, the interposing oligonucleotide barcodes (alternatively referred to herein as interposing barcodes (IBCs)) provided herein include a first and second hybridization pad that are complementary to a first and second sequence of a sample polynucleotide, respectively. In embodiments, each hybridization pad includes about 10 to about 25 nucleotides (e.g., random nucleotides). In embodiments, each hybridization pad includes about 3 to about 5 nucleotides (e.g., random nucleotides). In embodiments, each hybridization pad has 3 to 5 nucleotides (e.g., random nucleotides). In embodiments, the first hybridization pad includes more nucleotides than the second hybridization pad. See for example FIG. 4 illustrating an interposing oligonucleotide barcode with asymmetric hybridization pads. In embodiments, the first hybridization pad includes about 3 to about 5 nucleotides (e.g., random nucleotides) and the second hybridization pad includes about 3 to 25 nucleotides (e.g., random nucleotides). In embodiments, the first hybridization pad includes about 3 to about 25 nucleotides and the second hybridization pad includes about 3 to 5 nucleotides. In embodiments, the first hybridization pad includes about 3 to about 25 nucleotides and the second hybridization pad includes about 3 to 25 nucleotides. In embodiments, the first hybridization pad includes about 10 to about 25 nucleotides and the second hybridization pad includes about 10 to 5 nucleotides. In embodiments, the first hybridization pad includes about 10 to about 15 nucleotides and the second hybridization pad includes about 10 to 15 nucleotides. In embodiments, the interposing oligonucleotide barcodes provided herein include a hybridization pad that includes about 1 to about 20 nucleotides, about 5 to about 15 nucleotides, or about 8 to about 12 nucleotides. In embodiments, the interposing oligonucleotide barcodes include a hybridization pad that includes about 9 to about 18 nucleotides. In embodiments, the interposing oligonucleotide barcodes include a hybridization pad that includes a targeted primer sequence, i.e. a nucleic acid sequence that is complementary to a known nucleic acid region. For example, the targeted primer sequence may be complementary to a universally conserved region, or complementary sequences to target specific genes or mutations that have relevancy to a particular cancer phenotype. In embodiments, the total combined length of the first hybridization pad and the second hybridization pad includes about 18 to about 25 nucleotides.

In embodiments, the interposing oligonucleotide barcodes provided herein include a hybridization pad that includes about 1 to about 10 nucleotides, about 2 to about 9 nucleotides, about 3 to about 8 nucleotides, about 4 to about 7 nucleotides, or about 5 to about 6 nucleotides. In embodiments, the interposing oligonucleotide barcodes provided herein include a hybridization pad that includes 1, 2, 3, 4, 5, 6, 7, 8, 9, or 10 nucleotides. In embodiments, the interposing oligonucleotide barcodes provided herein include a hybridization pad that includes 3 nucleotides. In embodiments, the interposing oligonucleotide barcodes provided herein include a hybridization pad that includes 4 nucleotides. In embodiments, the interposing oligonucleotide barcodes provided herein include a hybridization pad that includes 5 nucleotides. In embodiments, the interposing oligonucleotide barcodes provided herein include a hybridization pad that includes 6 nucleotides. In embodiments, the interposing oligonucleotide barcodes provided herein include a hybridization pad that includes 7 nucleotides. In embodiments, the interposing oligonucleotide barcodes provided herein include a hybridization pad that includes 8 nucleotides. In embodiments, the interposing oligonucleotide barcodes provided herein include two hybridization pads, and each hybridization pad consists of 4 nucleotides. In embodiments, the interposing oligonucleotide barcodes provided herein include two hybridization pads, and each hybridization pad consists of 5 nucleotides. In embodiments, the interposing oligonucleotide barcodes provided herein include two hybridization pads, and each hybridization pad consists of 6 nucleotides. In embodiments, the interposing oligonucleotide barcodes provided herein include two hybridization pads, and each hybridization pad consists of 7 nucleotides. In embodiments, the interposing oligonucleotide barcodes provided herein include two hybridization pads, and each hybridization pad consists of 8 nucleotides. In embodiments, the interposing oligonucleotide barcodes provided herein include two hybridization pads, and each hybridization pad consists of 9 nucleotides. In embodiments, the interposing oligonucleotide barcodes provided herein include two hybridization pads, and each hybridization pad consists of 10 nucleotides. In embodiments, the interposing oligonucleotide barcodes provided herein include two hybridization pads, and each hybridization pad consists of 11 nucleotides. In embodiments, the interposing oligonucleotide barcodes provided herein include two hybridization pads, and each hybridization pad consists of 12 nucleotides. In embodiments, the interposing oligonucleotide barcodes include a hybridization pad having a first sequence (e.g., ATTG) and a second sequence (e.g., CCTA) that are independently different from each other. In embodiments, the interposing oligonucleotide barcodes include a hybridization pad having a first sequence (e.g., TACG) and a second sequence (e.g., TACG) that are identical. In embodiments, the interposing oligonucleotide barcodes include a hybridization pad having a first sequence (e.g., ATTG) and a second sequence (e.g., CCTATTACGATAACA (SEQ ID NO:1)) that are independently different from each other. In embodiments, the first hybridization pad includes a targeted primer sequence, or a portion thereof. In embodiments, the second hybridization pad includes a targeted priming sequence, or a portion thereof.

In embodiments, the hybridization pad includes at least one target-specific region (also referred to herein as a target priming sequence). A target-specific region is a single stranded polynucleotide that is at least 50% complementary, at least 75% complementary, at least 85% complementary, at least 90% complementary, at least 95% complementary, at least 98%, at least 99% complementary, or 100% complementary to a portion of a nucleic acid molecule that includes a known target sequence (e.g., a gene or gene fragment of interest). In embodiments, the target-specific region is capable of hybridizing to at least a portion of the target sequence. In embodiments, the target-specific region is substantially non-complementary to other target sequences present in the sample.

The melting temperature (Tm) of an interposing barcode can be changed (e.g., increased) to a desired Tm using a suitable method, for example by changing (e.g., increasing) GC content, changing (e.g., increasing) length and/or by the inclusion of modified nucleotides, nucleotide analogues and/or modified nucleotides bonds, non-limiting examples of which include locked nucleic acids (LNAs, e.g., bicyclic nucleic acids), bridged nucleic acids (BNAs, e.g., constrained nucleic acids), C5-modified pyrimidine bases (for example, 5-methyl-dC, propynyl pyrimidines, among others) and alternate backbone chemistries, for example peptide nucleic acids (PNAs), morpholinos, the like or combinations thereof. In embodiments, the interposing barcodes include nucleotide analogues to increase binding stability (e.g., Locked Nucleic Acid bases (LNAs)). For example, an interposing barcode that includes synthetic analogue bases such as LNAs (e.g., LNAs as described in US 2003/0092905; U.S. Pat. No. 7,084,125, which are incorporated herein by reference for all purposes) may increase the Tm. In embodiments, the interposing barcode includes a plurality of LNAs (e.g., 2, 3, 4, 5, 6, 7, 8, 9, or 10 LNAs). In embodiments, the interposing barcode includes 2-6 LNAs. In embodiments, the hybridization pad includes one or more modified nucleotides, such as LNAs. In embodiments, each hybridization pad includes one or more LNAs. In embodiments, the interposing barcode has the general formula 5'-[hybridization pad 1 domain]-[stem 1 domain]-[loop domain]-[stem 2 domain]-[hybridization pad 2 domain]-3'. In embodiments, the interposing barcode has the formula: 5'Phos-[hybridization pad 1 domain]-[stem 1 domain]-[loop domain]-[stem 2 domain]-[hybridization pad 2 domain]-3', wherein the hybridization pad 1 domain has the sequence: ACCACG+GTCAC (SEQ ID NO:2); stem 1 domain has the sequence: CTCCAC (SEQ ID NO:3); loop domain has the sequence TTNNNNNNNNNNNTT (SEQ ID NO: 4), wherein 'N' is a random nucleotide; stem 2 domain has the sequence: GTGGAG (SEQ ID NO: 5); and the hybridization pad 2 domain has the sequence CGT+CTCCTCAG (SEQ ID NO:6), wherein +G and +C represent the LNA bases. In embodiments, the Tm of hybridization pad is greater than 40° C. In embodiments, the Tm of hybridization pad is greater than 45° C.

In embodiments, the interposing oligonucleotide barcodes provided herein include a first and second hybridization pad that include randomly generated sequences. In embodiments, the interposing oligonucleotide barcodes provided herein include a first and second hybridization pad that include targeting priming sequences, or a portion thereof. In embodiments, the interposing oligonucleotide barcodes provided herein do not include a first and second hybridization pad that include randomly generated sequences.

In embodiments, the interposing oligonucleotide barcodes provided herein include a first and second stem region. The first and second stem regions are composed of complementary nucleotide sequences. In embodiments, the first stem region includes a sequence common to a plurality of the interposing oligonucleotide barcodes. In embodiments, the second stem region includes a sequence complementary to the first stem region, where the second stem region is capable of hybridizing to the first stem region under hybridization conditions.

In embodiments, the interposing oligonucleotide barcodes include a loop region that is comprised of random nucleotides, which may function as a molecular identifier. In embodiments, the loop region alone (e.g., Type 1 as observed in FIG. 1A) may be considered a molecular identifier. In embodiments, the loop region further includes a sample index sequence (e.g., Type 2 as observed in FIG. 1A).

In embodiments, the first and second stem regions of the interposing oligonucleotide barcodes provided herein include a known sequence of about 5 to about 10 nucleotides. In embodiments, the first and second stem regions of the interposing oligonucleotide barcodes provided herein include a known sequence of about 1 to about 20 nucleotides, about 2 to about 19, about 3 to about 18 nucleotides, about 4 to about 17 nucleotides, about 5 to about 16 nucleotides, about 6 to about 15 nucleotides, about 7 to about 14 nucleotides, about 8 to about 13 nucleotides, about 9 to about 12 nucleotides, or about 10 to about 11 nucleotides. In embodiments, the first and second stem regions of the interposing oligonucleotide barcodes provided herein include a known sequence of about 1, 2, 3, 4, 5, 6, 7, 8, 9, 10, 11, 12, 13, 14, 15, 16, 17, 18, 19, or about 20 nucleotides. In embodiments of the interposing oligonucleotide barcodes provided herein, the first stem region includes about 5 nucleotides. In embodiments of the interposing oligonucleotide barcodes provided herein, the first stem region includes about 6 nucleotides. In embodiments of the interposing oligonucleotide barcodes provided herein, the first stem region includes about 7 nucleotides. In embodiments of the interposing oligonucleotide barcodes provided herein, the first stem region includes about 8 nucleotides. In embodiments of the interposing oligonucleotide barcodes provided herein, the first stem region includes about 9 nucleotides. In embodiments of the interposing oligonucleotide barcodes provided herein, the first stem region includes about 10 nucleotides. In embodiments of the interposing oligonucleotide barcodes provided herein, the second stem region includes about 5 nucleotides. In embodiments of the interposing oligonucleotide barcodes provided herein, the second stem region includes about 6 nucleotides. In embodiments of the interposing oligonucleotide barcodes provided herein, the second stem region includes about 7 nucleotides. In embodiments of the interposing oligonucleotide barcodes provided herein, the second stem region includes about 8 nucleotides. In embodiments of the interposing oligonucleotide barcodes provided herein, the second stem region includes about 9 nucleotides. In embodiments of the interposing oligonucleotide barcodes provided herein, the second stem region includes about 10 nucleotides. In embodiments, the first and second stem regions are substantially complementary to each other.

In embodiments, the interposing oligonucleotide barcodes provided herein include a loop region that further includes a sample index sequence. In general, a sample index sequence is the same for all polynucleotides from the same sample source (e.g., the same subject, the same aliquot, or the same container), and differs from the sample index sequence of polynucleotides from a different sample source. Polynucleotides from different samples can therefore be mixed, and the sequences subsequently grouped by sample source by virtue of the sample index sequence. In embodiments, the sample index sequence is a randomly generated sequence that is sufficiently different from other sample index sequences to allow the identification of the sample source based on index sequence(s) with which they are associated. In embodiments, each sample index sequence in a plurality of index sequences differs from every other index sequence in the plurality by at least three nucleotide positions, such as at least 3, 4, 5, 6, 7, 8, 9, 10, or more nucleotide positions. In some embodiments, substantially degenerate index sequences may be known as random. In some embodiments a sample index sequence may include a nucleic acid sequence from within a pool of known sequences. In some embodiments, the sample index sequences may be predefined. In embodiments, the sample index sequence includes about 1 to about 10 nucleotides. In embodiments, the sample index sequence includes about 3, 4, 5, 6, 7, 8, 9, or about 10 nucleotides. In embodiments, the sample index sequence includes about 3 nucleotides. In embodiments, the sample index sequence includes about 5 nucleotides. In embodiments, the sample index sequence includes about 7 nucleotides. In embodiments, the sample index sequence includes about 10 nucleotides. In embodiments, the sample index sequence includes about 11 nucleotides. In embodiments, the sample index sequence includes about 12 nucleotides. In embodiments, the sample index sequence includes about 8 to 15 nucleotides. In embodiments, the sample index sequence includes 12 nucleotides.

In embodiments, the interposing oligonucleotide barcodes provided herein include a loop region. In embodiments, the loop region, alone or in combination with a sequence of one or both of (a) the sample polynucleotide, or (b) one or more barcode sequences, uniquely distinguishes the sample polynucleotide from other sample polynucleotides in a plurality of sample polynucleotides. In embodiments of the interposing oligonucleotide barcodes provided herein, the loop region includes about 5 to about 20 nucleotides or about 10 to about 20 nucleotides. In embodiments of the interposing oligonucleotide barcodes provided herein, the loop region includes about 1 to about 25, about 2 to about 24, about 3 to about 23, about 4 to about 22, about 5 to about 21, about 6 to about 20, about 7 to about 19, about 8 to about 18, about 9 to about 17, about 10 to about 16, about 11 to about 15, or about 12 to about 14 nucleotides. In embodiments of the interposing oligonucleotide barcodes provided herein, the loop region includes about 1, 2, 3, 4, 5, 6, 7, 8, 9, 10, 11, 12, 13, 14, 15, 16, 17, 18, 19, 20, 21, 22, 23, 24, or about 25 nucleotides. In embodiments of the interposing oligonucleotide barcodes provided herein, the loop region includes about 5 nucleotides. In embodiments of the interposing oligonucleotide barcodes provided herein, the loop region includes about 10 nucleotides. In embodiments of the interposing oligonucleotide barcodes provided herein, the loop region includes about 15 nucleotides. In embodiments of the interposing oligonucleotide barcodes provided herein, the loop region includes about 20 nucleotides. In embodiments, the loop region does not include a sample index sequence. In embodiments, the loop includes a TT-[UMI sequence]-TT sequence, such as TT-[NNNNNNNNNNNN]-TT (SEQ ID NO:11) sequence, wherein N represents random nucleotides and A, T, C, G represent fixed nucleotides).

In embodiments, the interposing oligonucleotide barcodes provided herein include a loop region that includes a barcode sequence. In embodiments, the loop includes only one barcode (e.g., one UMI sequence). In embodiments, the barcode sequence, alone or in combination with a sequence of one or both of (a) the sample polynucleotide, or (b) one or more additional barcode sequences, uniquely distinguishes the sample polynucleotide from other sample polynucleotides in a plurality of sample polynucleotides. In embodiments of the interposing oligonucleotide barcodes provided herein, the barcode sequence includes about 5 to about 20 nucleotides or about 10 to about 20 nucleotides. In embodiments of the interposing oligonucleotide barcodes provided herein, the barcode sequence includes about 1 to about 25, about 2 to about 24, about 3 to about 23, about 4 to about 22, about 5 to about 21, about 6 to about 20, about 7 to about 19, about 8 to about 18, about 9 to about 17, about 10 to about 16, about 11 to about 15, or about 12 to about 14 nucleotides. In embodiments of the interposing oligonucleotide barcodes provided herein, the barcode sequence includes about 1, 2, 3, 4, 5, 6, 7, 8, 9, 10, 11, 12, 13, 14, 15, 16, 17, 18, 19, 20, 21, 22, 23, 24, or about 25 nucleotides. In embodiments of the interposing oligonucleotide barcodes provided herein, the barcode sequence includes about 5 nucleotides. In embodiments of the interposing oligonucleotide barcodes provided herein, the barcode sequence includes about 10 nucleotides. In embodiments of the interposing oligonucleotide barcodes provided herein, the barcode sequence includes about 15 nucleotides. In embodiments of the interposing oligonucleotide barcodes provided herein, the barcode sequence includes about 20 nucleotides. In embodiments, the loop region does not include a barcode sequence.

In embodiments, the interposing oligonucleotide barcodes provided herein include a loop region that includes a barcode sequence, wherein the barcode sequence is selected from a set of barcode sequences represented by a random or partially random sequence. In embodiments, the interposing oligonucleotide barcodes provided herein include a loop region that includes a barcode sequence, where the barcode sequence is selected from a set of barcode sequences represented by a random sequence. In embodiments, the interposing oligonucleotide barcodes provided herein include a loop region that includes a barcode sequence, where each barcode sequence is selected from a set of barcode sequences represented by a partially random sequence.

In embodiments, the interposing oligonucleotide barcodes provided herein includes a random sequence. In embodiments, the interposing oligonucleotide barcodes provided herein include a barcode sequence that includes a random sequence. In embodiments, the random sequence excludes a subset of sequences, where the excluded subset includes sequences with three or more identical consecutive nucleotides. In embodiments, the excluded subset includes sequences with three identical consecutive nucleotides. In embodiments, the excluded subset includes sequences with four identical consecutive nucleotides. In embodiments, the excluded subset includes sequences with five identical consecutive nucleotides.

In embodiments, the interposing oligonucleotide barcodes provided herein include a barcode sequence, where each barcode sequence differs from every other barcode sequence by at least two nucleotide positions. In embodiments, the interposing oligonucleotide barcodes provided herein include barcode sequences, where each barcode sequence differs from every other barcode sequence by at least three nucleotide positions. In embodiments, the interposing oligonucleotide barcodes provided herein include barcode sequences, where each barcode sequence differs from every other barcode sequence by at least four nucleotide positions. In embodiments, the interposing oligonucleotide barcodes provided herein include barcode sequences, where each barcode sequence differs from every other barcode sequence by at least five nucleotide positions.

In embodiments, the interposing oligonucleotide barcodes provided herein include a loop region that includes a barcode sequence that alone or in combination with a sequence of one or both of (a) the sample polynucleotide, or (b) one or more additional barcode sequences, uniquely distinguishes the sample polynucleotide from other sample polynucleotides in a plurality of sample polynucleotides. In embodiments, the interposing oligonucleotide barcodes provided herein include a loop region that includes a barcode sequence that alone uniquely distinguishes the sample polynucleotide from other sample polynucleotides in a plurality of sample polynucleotides. In embodiments, the interposing oligonucleotide barcodes provided herein include a loop region that includes a barcode sequence that in combination with a sequence of the sample polynucleotide uniquely distinguishes the sample polynucleotide from other sample polynucleotides in a plurality of sample polynucleotides. In embodiments, the interposing oligonucleotide barcodes provided herein include a loop region that includes a barcode sequence that in combination with a sequence of one or more additional barcode sequences, uniquely distinguishes the sample polynucleotide from other sample polynucleotides in a plurality of sample polynucleotides. In embodiments, the interposing oligonucleotide barcodes provided herein include a loop region that includes a barcode sequence that in combination with a sequence of the sample polynucleotide, and one or more additional barcode sequences, uniquely distinguishes the sample polynucleotide from other sample polynucleotides in a plurality of sample polynucleotides.

In embodiments, the interposing oligonucleotide barcodes provided herein include a 5' phosphate moiety. A phosphate moiety attached to the 5'-end permits ligation of two nucleotides, i.e., the covalent binding of a 5'-phosphate to the 3'-hydroxyl group of another nucleotide, to form a phosphodiester bond. Removal of the 5'-phosphate prevents ligation.

In embodiments, provided herein is a composition including a sample polynucleotide hybridized to a plurality of oligonucleotides barcodes (e.g., interposing barcodes) according to any of the aspects of interposing barcodes described herein. In embodiments the sample polynucleotide is an RNA transcript. In embodiments, the polynucleotide is mRNA.

In embodiments, provided herein is a composition including a sample polynucleotide hybridized to a plurality of oligonucleotides barcodes (e.g., interposing barcodes) according to any of the aspects of interposing barcodes described herein, where the second hybridization pad is at least twice as long as the first hybridization pad (e.g., the first hybridization pad is 5 nucleotides in length and the second is at least 10 nucleotides in length). In embodiments, the second hybridization pad is at least three times as long as the first hybridization pad. In embodiments, the second hybridization pad is at least four times as long as the first hybridization pad. In embodiments, the second hybridization pad is more than four times as long as the first hybridization pad. In embodiments, the second hybridization pad is the same length as the first hybridization pad. In embodiments, the sample polynucleotide can include any nucleic acid of interest. The nucleic acid can include DNA, RNA, peptide nucleic acid (PNA), morpholino nucleic acid, locked nucleic acid (LNA), glycol nucleic acid, threose nucleic acid, mixtures thereof, and hybrids thereof. In embodiments, the nucleic acid is obtained from one or more source organisms. In some embodiments, the nucleic acid can include a selected sequence or a portion of a larger sequence. In embodiments, sequencing a portion of a nucleic acid or a fragment thereof can be used to identify the source of the nucleic acid. With reference to nucleic acids, polynucleotides and/or nucleotide sequences a "portion," "fragment" or "region" can be at least 5 consecutive nucleotides, at least 10 consecutive nucleotides, at least 15 consecutive nucleotides, at least 20 consecutive nucleotides, at least 25 consecutive nucleotides, at least 50 consecutive nucleotides, at least 100 consecutive nucleotides, or at least 150 consecutive nucleotides.

In embodiments, the sample polynucleotide is at least 1000 bases (1 kb), at least 2 kb, at least 4 kb, at least 6 kb, at least 10 kb, at least 20 kb, at least 30 kb, at least 40 kb, or at least 50 kb in length. In embodiments, the entire sequence of the sample polynucleotide is about 1 to 3 kb, and only a portion of that the sample polynucleotide (e.g., 50 to 100 nucleotides) is sequenced at a time. In embodiments, the sample polynucleotide is about 2 to 3 kb. In embodiments, the sample polynucleotide is about 1 to 10 kb. In embodiments, the sample polynucleotide is about 3 to 10 kb. In embodiments, the sample polynucleotide is about 5 to 10 kb. In embodiments, the sample polynucleotide is about 1 to 3 kb. In embodiments, the sample polynucleotide is about 1 to 2 kb. In embodiments, the sample polynucleotide is greater than 1 kb. In embodiments, the sample polynucleotide is greater than 500 bases. In embodiments, the sample polynucleotide is about 1 kb. In embodiments, the sample polynucleotide is about 2 kb. In embodiments, the sample polynucleotide is less than 1 kb. In embodiments, the sample polynucleotide is about 500 nucleotides. In embodiments, the sample polynucleotide is about 510 nucleotides. In embodiments, the sample polynucleotide is about 520 nucleotides. In embodiments, the sample polynucleotide is about 530 nucleotides. In embodiments, the sample polynucleotide is about 540 nucleotides. In embodiments, the sample polynucleotide is about 550 nucleotides. In embodiments, the sample polynucleotide is about 560 nucleotides. In embodiments, the sample polynucleotide is about 570 nucleotides. In embodiments, the sample polynucleotide is about 580 nucleotides. In embodiments, the sample polynucleotide is about 590 nucleotides. In embodiments, the sample polynucleotide is about 600 nucleotides. In embodiments, the sample polynucleotide is about 610 nucleotides. In embodiments, the sample polynucleotide is about 620 nucleotides. In embodiments, the sample polynucleotide is about 630 nucleotides. In embodiments, the sample polynucleotide is about 640 nucleotides. In embodiments, the sample polynucleotide is about 650 nucleotides. In embodiments, the sample polynucleotide is about 660 nucleotides. In embodiments, the sample polynucleotide is about 670 nucleotides. In embodiments, the sample polynucleotide is about 680 nucleotides. In embodiments, the sample polynucleotide is about 690 nucleotides. In embodiments, the sample polynucleotide is about 700 nucleotides. In embodiments, the sample polynucleotide is about 1,600 nucleotides. In embodiments, the sample polynucleotide is about 1,610 nucleotides. In embodiments, the sample polynucleotide is about 1,620 nucleotides. In embodiments, the sample polynucleotide is about 1,630 nucleotides. In embodiments, the sample polynucleotide is about 1,640 nucleotides. In embodiments, the sample polynucleotide is about 1,650 nucleotides. In embodiments, the sample polynucleotide is about 1,660 nucleotides. In embodiments, the sample polynucleotide is about 1,670 nucleotides. In embodiments, the sample polynucleotide is about 1,680 nucleotides. In embodiments, the sample polynucleotide is about 1,690 nucleotides. In embodiments, the sample polynucleotide is about 1,700 nucleotides. In embodiments, the sample polynucleotide is about 1,710 nucleotides. In embodiments, the sample polynucleotide is about 1,720 nucleotides. In embodiments, the sample polynucleotide is about 1,730 nucleotides. In embodiments, the sample polynucleotide is about 1,740 nucleotides. In embodiments, the sample polynucleotide is about 1,750 nucleotides. In embodiments, the sample polynucleotide is about 1,760 nucleotides. In embodiments, the sample polynucleotide is about 1,770 nucleotides. In embodiments, the sample polynucleotide is about 1,780 nucleotides. In embodiments, the sample polynucleotide is about 1,790 nucleotides. In embodiments, the sample polynucleotide is about 1,800 nucleotides.

In embodiments, the sample polynucleotide is a nucleic acid sequence. In embodiments the sample polynucleotide is an RNA transcript. RNA transcripts are responsible for the process of converting DNA into an organism's phenotype, thus by determining the types and quantity of RNA present in a sample (e.g., a cell), it is possible to assign a phenotype to the cell. RNA transcripts include coding RNA and non-coding RNA molecules, such as messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the target is pre-mRNA. In embodiments, the target is heterogeneous nuclear RNA (hnRNA). In embodiments the sample polynucleotide is a single stranded RNA nucleic acid sequence. In embodiments, the sample polynucleotide is an RNA nucleic acid sequence or a DNA nucleic acid sequence (e.g., cDNA). In embodiments, the sample polynucleotide is a cDNA target nucleic acid sequence. In embodiments, the sample polynucleotide is genomic DNA (gDNA), mitochondrial DNA, chloroplast DNA, episomal DNA, viral DNA, or complementary DNA (cDNA). In embodiments, the sample polynucleotide is coding RNA such as messenger RNA (mRNA), and non-coding RNA (ncRNA) such as transfer RNA (tRNA), microRNA (miRNA), small nuclear RNA (snRNA), or ribosomal RNA (rRNA).

In embodiments, the sample polynucleotide is a cancer-associated gene or fragment thereof. In general, "cancer associated genes" are genes for which change in expression, change in activity of an encoded protein, mutation, or a combination of these is correlated with the occurrence of cancer. A variety of cancer-associated genes are known. In embodiments, the cancer-associated gene is a MDC, NME-2, KGF, P1GF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, or EPO gene or fragment thereof. In embodiments, the cancer-associated gene is a AKT1, AKT2, AKT3, ALK, AR, ARAF, ARID1A, ATM, ATR, ATRX, AXL, BAP1, BRAF, BRCA1, BRCA2, BTK, CBL, CCND1, CCND2, CCND3, CCNE1, CDK12, CDK2, CDK4, CDK6, CDKN1B, CDKN2A, CDKN2B, CHEK1, CHEK2, CREBBP, CSF1R, CTNNB1, DDR2, EGFR, ERBB2, ERBB3, ERBB4, ERCC2, ERG, ESR1, ETV1, ETV4, ETV5, EZH2, FANCA, FANCD2, FANCI, FBXW7, FGF19, FGF3, FGFR1, FGFR2, FGFR3, FGFR4, FGR, FLT3, FOXL2, GATA2, GNA11, GNAQ, GNAS, H3F3A, HIST1H3B, HNF1A, HRAS, IDH1, IDH2, IGF1R, JAK1, JAK2, JAK3, KDR, KIT, KNSTRN, KRAS, MAGOH, MAP2K1, MAP2K2, MAP2K4, MAPK1, MAX, MDM2, MDM4, MED12, MET, MLH1, MRE11A, MSH2, MSH6, MTOR, MYB, MYBL1, MYC, MYCL, MYCN, MYD88, NBN, NF1, NF2, NFE2L2, NOTCH1, NOTCH2, NOTCH3, NOTCH4, NRAS, NRG1, NTRK1, NTRK2, NTRK3, NUTM1, PALB2, PDGFRA, PDGFRB, PIK3CA, PIK3CB, PIK3R1, PMS2, POLE, PPARG, PPP2R1A, PRKACA, PRKACB, PTCH1, PTEN, PTPN11, RAC1, RAD50, RAD51, RAD51B, RAD51C, RAD51D, RAF1, RB1, RELA, RET, RHEB, RHOA, RICTOR, RNF43, ROS1, RSPO2, RSPO3, SETD2, SF3B1, SLX4, SMAD4, SMARCA4, SMARCB1, SMO, SPOP, SRC, STAT3, STK11, TERT, TOP1, TP53, TSC1, TSC2, U2AF1, or XPO1 gene, or fragment thereof. In embodiments, the cancer-associated gene is a ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNF1A, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, or VHL gene, or fragment thereof.

In embodiments, the sample polynucleotides are RNA nucleic acid sequences or DNA nucleic acid sequences. In embodiments, the sample polynucleotides are RNA nucleic acid sequences or DNA nucleic acid sequences from the same cell. In embodiments, the sample polynucleotides are RNA nucleic acid sequences. In embodiments, the RNA nucleic acid sequence is stabilized using known techniques in the art. For example, RNA degradation by RNase should be minimized using commercially available solutions (e.g., RNA Later®, RNA Protect®, or DNA/RNA Shield®). In embodiments, the sample polynucleotides are messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the sample polynucleotide is pre-mRNA. In embodiments, the sample polynucleotide is heterogeneous nuclear RNA (hnRNA). In embodiments, the sample polynucleotide is mRNA, tRNA (transfer RNA), rRNA (ribosomal RNA), or noncoding RNA (such as lncRNA (long noncoding RNA)). In embodiments, the sample polynucleotides are on different regions of the same RNA nucleic acid sequence. In embodiments, the sample polynucleotides are cDNA target nucleic acid sequences and before step i), the RNA nucleic acid sequences are reverse transcribed to generate the cDNA target nucleic acid sequences. In embodiments, the sample polynucleotides are not reverse transcribed to cDNA. When mRNA is reverse transcribed an oligo(dT) primer can be added to better hybridize to the poly A tail of the mRNA. The oligo(dT) primer may include between about 12 and about 25 dT residues. The oligo(dT) primer may be an oligo(dT) primer of between about 18 to about 25 nt in length.

In embodiments, the polynucleotide includes a gene or a gene fragment. In embodiments, the gene or gene fragment is a cancer-associated gene or fragment thereof, T cell receptor (TCRs) gene or fragment thereof, or a B cell receptor (BCRs) gene, or fragment thereof. In embodiments, the gene or gene fragment is a CDR3 gene or fragment thereof. In embodiments, the gene or gene fragment is a T cell receptor alpha variable (TRAV) gene or fragment thereof, T cell receptor alpha joining (TRAJ) gene or fragment thereof, T cell receptor alpha constant (TRAC) gene or fragment thereof, T cell receptor beta variable (TRBV) gene or fragment thereof, T cell receptor beta diversity (TRBD) gene or fragment thereof, T cell receptor beta joining (TRBJ) gene or fragment thereof, T cell receptor beta constant (TRBC) gene or fragment thereof, T cell receptor gamma variable (TRGV) gene or fragment thereof, T cell receptor gamma joining (TRGJ) gene or fragment thereof, T cell receptor gamma constant (TRGC) gene or fragment thereof, T cell receptor delta variable (TRDV) gene or fragment thereof, T cell receptor delta diversity (TRDD) gene or fragment thereof, T cell receptor delta joining (TRDJ) gene or fragment thereof, or T cell receptor delta constant (TRDC) gene or fragment thereof. In embodiments, the polynucleotide includes genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA). In embodiments, the polynucleotide includes messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA).

In embodiments, the methods and compositions described herein are utilized to analyze the various sequences of T cell receptors (TCRs) and B cell receptors (BCRs) from immune cells, for example various clonotypes. In embodiments, the target nucleic acid includes a nucleic acid sequence encoding a TCR alpha (TCRA) chain, a TCR beta (TCRB) chain, a TCR delta (TCRD) chain, a TCR gamma (TCRG) chain, or any fragment thereof (e.g., variable regions including VDJ or VJ regions, constant regions, transmembrane regions, fragments thereof, combinations thereof, and combinations of fragments thereof). In embodiments, the target nucleic acid includes a nucleic acid sequence encoding a B cell receptor heavy chain, B cell receptor light chain, or any fragment thereof (e.g., variable regions including VDJ or VJ regions, constant regions, transmembrane regions, fragments thereof, combinations thereof, and combinations of fragments thereof). In embodiments, the target nucleic acid includes a CDR3 nucleic acid sequence. In embodiments, the target nucleic acid includes a TCRA gene sequence or a TCRB gene sequence. In embodiments, the target nucleic acid includes a TCRA gene sequence and a TCRB gene sequence. In embodiments, the target nucleic acid includes sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), or T cell receptor delta constant genes (TRDC genes).

Methods

In an aspect, provided herein are methods of making tagged complements (e.g., interposing oligonucleotide barcode tagged complements) of a plurality of sample polynucleotides. In embodiments, the methods include (a) hybridizing to each of the plurality of sample polynucleotides a plurality of interposing oligonucleotide barcodes (alternatively referred to herein as interposing barcodes); (b) extending the 3' ends of the interposing oligonucleotide barcodes with one or more polymerases to create extension products; and (c) ligating adjacent ends of extension products hybridized to the same sample polynucleotide thereby making complements of the plurality of sample polynucleotides tagged with a plurality of interposing oligonucleotide barcodes. Each of the interposing oligonucleotide barcodes are as described herein, including embodiments. In embodiments, each of the interposing oligonucleotide barcodes include from 5' to 3': (i) a first hybridization pad complementary to a first sequence of a sample polynucleotide; (ii) a first stem region including a sequence common to the plurality of interposing oligonucleotide barcodes; (iii) a loop region; (iv) a second stem region including a sequence complementary to the first stem region, where the second stem region is capable of hybridizing to the first stem region under hybridization conditions; and (v) a second hybridization pad complementary to a second sequence of the sample polynucleotide. In embodiments, each of the interposing oligonucleotide barcodes include from 5' to 3': (i) a first hybridization pad complementary to a first sequence of a sample polynucleotide; (ii) a first stem region including a sequence common to the plurality of interposing oligonucleotide barcodes; (iii) a loop region, optionally including a barcode sequence, where the barcode sequence, alone or in combination with a sequence of one or both of (a) the sample polynucleotide, or (b) one or more additional barcode sequences, uniquely distinguishes the sample polynucleotide from other sample polynucleotides in the plurality; (iv) a second stem region including a sequence complementary to the first stem region, where the second stem region is capable of hybridizing to the first stem region under hybridization conditions; and (v) a second hybridization pad complementary to a second sequence of the sample polynucleotide. In embodiments, the loop region comprises a sample index sequence. In embodiments, the loop region is a sample index sequence. In embodiments, a tagged complement of a sample polynucleotide refers to a complementary nucleic acid sequence that contains an interposing oligonucleotide barcode as described herein. In embodiments, the tagged complements include at least two interposing oligonucleotide barcodes. In embodiments, the tagged complements include at least three interposing oligonucleotide barcodes. In embodiments, the tagged complements include at least four interposing oligonucleotide barcodes. In embodiments, the tagged complements include at least 5 interposing oligonucleotide barcodes.

In an aspect is provided a method of amplifying tagged complements of a plurality of sample polynucleotides, the method including: (a) hybridizing to each of the plurality of sample polynucleotides a plurality of interposing oligonucleotide barcodes, each of the interposing oligonucleotide barcodes including from 5' to 3': (i) a first hybridization pad complementary to a first sequence of a sample polynucleotide; (ii) a first stem region comprising a sequence common to the plurality of interposing oligonucleotide barcodes; (iii) a loop region comprising a barcode sequence, wherein the barcode sequence, alone or in combination with a sequence of one or both of (a) the sample polynucleotide, or (b) one or more additional barcode sequences, uniquely distinguishes the sample polynucleotide from other sample polynucleotides in the plurality; (iii) a second stem region comprising a sequence complementary to the first stem region, wherein the second stem region is capable of hybridizing to the first stem region under hybridization conditions; and (iv) a second hybridization pad complementary to a second sequence of the sample polynucleotide; extending the 3' ends of the second hybridization pads with one or more polymerases to create extension products; and ligating adjacent ends of extension products hybridized to the same sample polynucleotide thereby making integrated strands comprising complements of the plurality of sample polynucleotides tagged with a plurality of interposing oligonucleotide barcodes; and amplifying the integrated strands by an amplification reaction thereby amplifying the tagged complements of the plurality of sample polynucleotides.

In embodiments, amplifying includes hybridizing an amplification primer to the integrated strands and cycles of primer extension with a polymerase and nucleotides to generate amplified products. In embodiments, the amplification reaction includes polymerase chain reaction (PCR), strand displacement amplification (SDA), multiple displacement amplification (MDA), ligation chain reaction, transcription mediated amplification (TMA), nucleic acid sequence based amplification (NASBA), rolling circle amplification (RCA), exponential rolling circle amplification (eRCA), hyperbranched rolling circle amplification (HRCA), or a combination thereof.

In embodiments, the sample polynucleotide includes a gene or a gene fragment. In embodiments, the gene or gene fragment is a cancer-associated gene or fragment thereof, T cell receptor (TCRs) gene or fragment thereof, or a B cell receptor (BCRs) gene, or fragment thereof. In embodiments, the gene or gene fragment is a CDR3 gene or fragment thereof. In embodiments, the gene or gene fragment is a T cell receptor alpha variable (TRAV) gene or fragment thereof, T cell receptor alpha joining (TRAJ) gene or fragment thereof, T cell receptor alpha constant (TRAC) gene or fragment thereof, T cell receptor beta variable (TRBV) gene or fragment thereof, T cell receptor beta diversity (TRBD) gene or fragment thereof, T cell receptor beta joining (TRBJ) gene or fragment thereof, T cell receptor beta constant (TRBC) gene or fragment thereof, T cell receptor gamma variable (TRGV) gene or fragment thereof, T cell receptor gamma joining (TRGJ) gene or fragment thereof, T cell receptor gamma constant (TRGC) gene or fragment thereof, T cell receptor delta variable (TRDV) gene or fragment thereof, T cell receptor delta diversity (TRDD) gene or fragment thereof, T cell receptor delta joining (TRDJ) gene or fragment thereof, or T cell receptor delta constant (TRDC) gene or fragment thereof. In embodiments, the polynucleotide includes genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA). In embodiments, the polynucleotide includes messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA).

In embodiments, the tagged complement is at least 1000 bases (1 kb), at least 2 kb, at least 4 kb, at least 6 kb, at least 10 kb, at least 20 kb, at least 30 kb, at least 40 kb, or at least 50 kb in length. In embodiments, the entire sequence of the tagged complement is about 1 to 3 kb, and only a portion of that the tagged complement (e.g., 50 to 100 nucleotides) is sequenced at a time. In embodiments, the tagged complement is about 2 to 3 kb. In embodiments, the tagged complement is about 1 to 10 kb. In embodiments, the tagged complement is about 3 to 10 kb. In embodiments, the tagged complement is about 5 to 10 kb. In embodiments, the tagged complement is about 1 to 3 kb. In embodiments, the tagged complement is about 1 to 2 kb. In embodiments, the tagged complement is greater than 1 kb. In embodiments, the tagged complement is greater than 500 bases. In embodiments, the tagged complement is about 1 kb. In embodiments, the tagged complement is about 2 kb. In embodiments, the tagged complement is less than 1 kb. In embodiments, the tagged complement is about 500 nucleotides. In embodiments, the tagged complement is about 510 nucleotides. In embodiments, the tagged complement is about 520 nucleotides. In embodiments, the tagged complement is about 530 nucleotides. In embodiments, the tagged complement is about 540 nucleotides. In embodiments, the tagged complement is about 550 nucleotides. In embodiments, the tagged complement is about 560 nucleotides. In embodiments, the tagged complement is about 570 nucleotides. In embodiments, the tagged complement is about 580 nucleotides. In embodiments, the tagged complement is about 590 nucleotides. In embodiments, the tagged complement is about 600 nucleotides. In embodiments, the tagged complement is about 610 nucleotides. In embodiments, the tagged complement is about 620 nucleotides. In embodiments, the tagged complement is about 630 nucleotides. In embodiments, the tagged complement is about 640 nucleotides. In embodiments, the tagged complement is about 650 nucleotides. In embodiments, the tagged complement is about 660 nucleotides. In embodiments, the tagged complement is about 670 nucleotides. In embodiments, the tagged complement is about 680 nucleotides. In embodiments, the tagged complement is about 690 nucleotides. In embodiments, the tagged complement is about 700 nucleotides. In embodiments, the tagged complement is about 1,600 nucleotides. In embodiments, the tagged complement is about 1,610 nucleotides. In embodiments, the tagged complement is about 1,620 nucleotides. In embodiments, the tagged complement is about 1,630 nucleotides. In embodiments, the tagged complement is about 1,640 nucleotides. In embodiments, the tagged complement is about 1,650 nucleotides. In embodiments, the tagged complement is about 1,660 nucleotides. In embodiments, the tagged complement is about 1,670 nucleotides. In embodiments, the tagged complement is about 1,680 nucleotides. In embodiments, the tagged complement is about 1,690 nucleotides. In embodiments, the tagged complement is about 1,700 nucleotides. In embodiments, the tagged complement is about 1,710 nucleotides. In embodiments, the tagged complement is about 1,720 nucleotides. In embodiments, the tagged complement is about 1,730 nucleotides. In embodiments, the tagged complement is about 1,740 nucleotides. In embodiments, the tagged complement is about 1,750 nucleotides. In embodiments, the tagged complement is about 1,760 nucleotides. In embodiments, the tagged complement is about 1,770 nucleotides. In embodiments, the tagged complement is about 1,780 nucleotides. In embodiments, the tagged complement is about 1,790 nucleotides. In embodiments, the tagged complement is about 1,800 nucleotides.

In embodiments, the methods of making tagged complements of a plurality of sample polynucleotides include hybridizing to each of the plurality of sample polynucleotides a plurality of interposing oligonucleotide barcodes (alternatively referred to herein as interposing barcodes). In embodiments, the methods include interposing oligonucleotide barcodes according to any of the aspects or embodiments disclosed herein. In embodiments, methods of hybridizing are known to those skilled in the art, and include, for example, lowering or raising the temperature of a reaction mixture to enable annealing of oligonucleotides to a polynucleotide.

Figure 13:
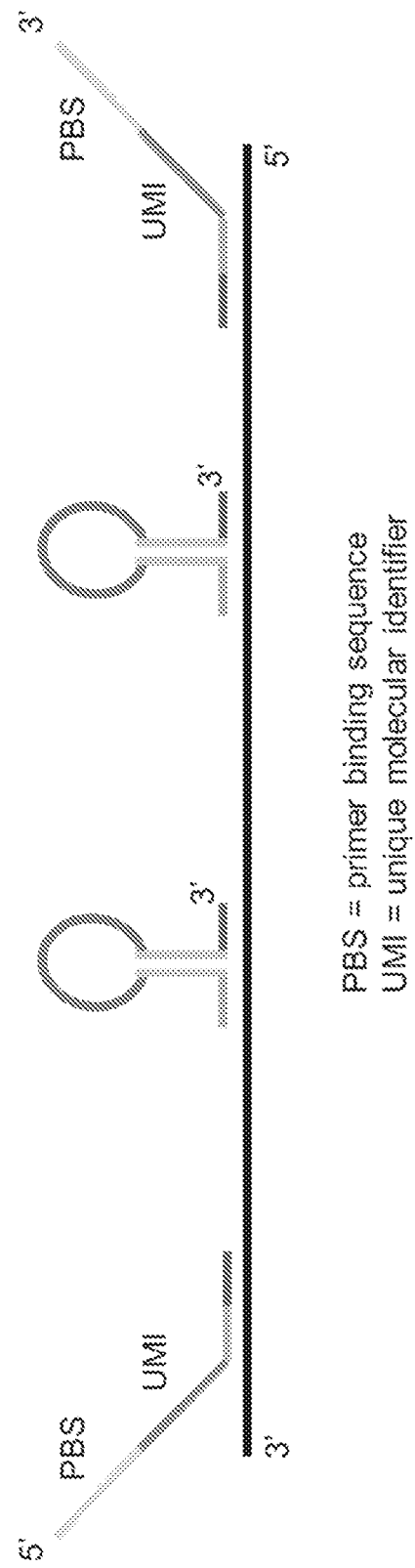
FIG. 13 illustrates an embodiment wherein IBCs are hybridized to a template polynucleotide in combination with terminal adapters. In embodiments, the terminal adapters include one or two hybridization pads as described herein, a barcode (e.g., a UMI), and a primer binding sequence.

In embodiments, the methods further include hybridizing one or more terminal adapters to the sample polynucleotide. A terminal adapter includes at least one hybridization pad as described herein (e.g., a hybridization pad of about 10 to about 30 nucleotides in length), a barcode (e.g., a UMI of about 8 to about 15 nucleotides in length), and a primer binding site (e.g., an amplification primer binding site of about 10 to about 25 nucleotides in length), as depicted in FIG. 13. In embodiments, the terminal adapter does not include a loop region or a stem region (e.g., a loop region or stem region as described herein). In embodiments, the terminal adapter is a single-stranded polynucleotide having at least one primer binding sequence. In embodiments, the terminal adapter includes at least one amplification primer binding sequence. In embodiments, the terminal adapter includes two or more amplification primer binding sequences. The amplification primer binding sequence refers to a nucleotide sequence that is complementary to a primer useful in initiating amplification (i.e., an amplification primer). Primer binding sequences usually have a length in the range of between 3 to 36 nucleotides, also 5 to 24 nucleotides, also from 14 to 36 nucleotides. In embodiments, the terminal adapter includes a barcode of about 8 nucleotides. In embodiments, the terminal adapter includes a barcode of about 12 nucleotides. In embodiments, the terminal adapter includes a barcode of about 15 nucleotides. In embodiments, the first and second hybridization pads have a total length of 15 to 25 nucleotides. In embodiments, the method includes hybridizing two terminal adapters to the sample polynucleotide.

In embodiments, the method further includes hybridizing a first terminal adapter having the sequence from 5' to 3', a primer binding sequence, a barcode, a first hybridization pad and a second hybridization pad to 3' end of a sample polynucleotide. In embodiments, the method further includes hybridizing a second terminal adapter having the sequence from 5' to 3', a first hybridization pad and a second hybridization pad, an index, and a primer binding sequence, wherein the first and the second hybridization pads anneal to the 5' end of a sample polynucleotide. In embodiments, both first and second terminal adapters are hybridized to a sample polynucleotide. In embodiments, amplifying includes hybridizing an amplification primer to the primer binding sequence of the terminal adapter and cycles of primer extension with a polymerase and nucleotides to generate amplified products.

In embodiments, the terminal adapter includes one or more phosphorothioate containing nucleotides. For example, one terminal adapter may include five terminal phosphorothioate linkages on the 3' end to prevent exonuclease degradation (e.g., exonuclease degradation by T4 DNA Polymerase). In embodiments, the terminal adapter includes one or more LNAs. In embodiments, the terminal adapter includes a modified nucleotide that contains an affinity tag (e.g., a biotin-containing nucleotide). The biotin-containing terminal adapter, for example, could then facilitate affinity purification of the tagged complement.

In embodiments, the methods of making tagged complements of a plurality of sample polynucleotides include extending the 3' ends of the interposing oligonucleotide barcodes with one or more polymerases to create extension products. Methods of extending 3' ends of oligonucleotides are known to those skilled in the art. In embodiments, extension is achieved by a DNA polymerase without strand displacement activity.

In embodiments, the methods of making tagged complements of a plurality of sample polynucleotides include ligating adjacent ends of extension products hybridized to the same sample polynucleotide thereby making complements of the plurality of sample polynucleotides tagged with a plurality of interposing oligonucleotide barcodes. Methods of ligation are known to those skilled in the art. In embodiments, the ligation includes enzymatic ligation. In embodiments, ligating includes enzymatic ligation including a ligation enzyme (e.g., CircLigase™ enzyme, Taq DNA Ligase, HiFi Taq DNA Ligase, T4 ligase, PBCV-1 DNA Ligase (also known as SplintR ligase) or Ampligase DNA Ligase). Non-limiting examples of ligases include DNA ligases such as DNA Ligase I, DNA Ligase II, DNA Ligase III, DNA Ligase IV, T4 DNA ligase, T7 DNA ligase, T3 DNA Ligase, E. coli DNA Ligase, PBCV-1 DNA Ligase (also known as SplintR ligase) or a Taq DNA Ligase. In embodiments, the ligating enzyme is T4 RNA ligase, T4 DNA ligase, T4 RNA ligase 2, Taq DNA ligase, or E. coli DNA ligase.

In embodiments, ligating includes chemical ligation (e.g., enzyme-free, click-mediated ligation). In embodiments, the extension products include a first bioconjugate reactive moiety capable of bonding upon contact with a second (complementary) bioconjugate reactive moiety. In embodiments, the extension products include an alkynyl moiety at the 3' and an azide moiety at the 5' end that, upon hybridization to the target nucleic acid react to form a triazole linkage during suitable reaction conditions. Reaction conditions and protocols for chemical ligation techniques that are compatible with nucleic acid amplification methods are known in the art, for example El-Sagheer, A. H., & Brown, T. (2012). *Accounts of chemical research*, 45(8), 1258-1267; Manuguerra I. et al. *Chem Commun (Camb)*. 2018; 54(36): 4529-4532; and Odeh, F., et al. (2019). *Molecules* (Basel, Switzerland), 25(1), 3, each of which is incorporated herein by reference in their entirety.

In embodiments, the methods of making tagged complements provided herein include interposing oligonucleotide barcodes according to any of the aspects disclosed herein. In embodiments, the methods of making tagged complements described herein include interposing oligonucleotide barcodes that include a phosphorylated 5' end.

In embodiments, the methods of making tagged complements provided herein do not include interposing oligonucleotide barcodes with a phosphorylated 5' end. In embodiments, the method includes phosphorylating the 5' ends of the interposing barcodes prior to step (c). Phosphorylation may be performed, before, during, or after extension. In embodiments, phosphorylation occurs in parallel with the extension reaction. In embodiments, ligation reaction occurs in parallel with the extension reaction.

In embodiments, the methods of making tagged complements provided herein further include sequencing the tagged complements.

In embodiments, the methods of making tagged complements provided herein include sequencing, where sequencing includes (a) amplifying the tagged complements of the plurality of sample polynucleotides by an amplification reaction thereby making amplified products; and (b) performing a sequencing reaction on the amplified products.

The nucleic acids described herein (e.g., the integrated strand, or the tagged complements) can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction comprises a suitable thermal stable polymerase. Thermal stable polymerases are known in the art and are stable for prolonged periods of time, at temperature greater than 80° C. when compared to common polymerases found in most mammals. In certain embodiments the term "amplified" refers to a method that comprises a polymerase chain reaction (PCR). Conditions conducive to amplification (i.e., amplification conditions) are known and often comprise at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

A nucleic acid can be amplified by a thermocycling method or by an isothermal amplification method. In some embodiments, a rolling circle amplification method is used. In some embodiments, amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface or substrate. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution-based primers can be used. Non-limiting examples of solid phase nucleic acid amplification reactions include interfacial amplification, bridge amplification, emulsion PCR, WildFire amplification (e.g., U.S. Patent Publ. No. 2013/0012399), the like or combinations thereof.

Suitable methods for amplification include, but are not limited to, the polymerase chain reaction (PCR), strand displacement amplification (SDA), transcription mediated amplification (TMA) and nucleic acid sequence based amplification (NASBA), for example, as described in U.S. Pat. No. 8,003,354, which is incorporated herein by reference in its entirety. The above amplification methods can be employed to amplify one or more nucleic acids of interest. For example, PCR, multiplex PCR, SDA, TMA, NASBA and the like can be utilized to amplify immobilized nucleic acid fragments. In embodiments, amplification includes thermal bridge polymerase chain reaction amplification; for example, as exemplified by the disclosures of U.S. Pat. Nos. 5,641,658; 7,115,400; 7,790,418; U.S. Patent Publ. No. 2008/0009420, each of which is incorporated herein by reference in its entirety. In general, bridge amplification uses repeated steps of annealing of primers to templates, primer extension, and separation of extended primers from templates. Because the forward and reverse primers are attached to the solid substrate, the extension products released upon separation from an initial template are also attached to the solid support. Both strands are immobilized on the solid substrate at the 5' end, preferably via a covalent attachment. The 3' end of an amplification product is then permitted to anneal to a nearby reverse primer, forming a "bridge" structure. The reverse primer is then extended to produce a further template molecule that can form another bridge. During bridge PCR, additional chemical additives may be included in the reaction mixture, in which the DNA strands are denatured by flowing a denaturant over the DNA, which chemically denatures complementary strands. This is followed by washing out the denaturant and reintroducing an amplification polymerase in buffer conditions that allow primer annealing and extension.

In embodiments, the amplifying includes rolling circle amplification (RCA) or rolling circle transcription (RCT) (see, e.g., Lizardi et al., Nat. Genet. 19:225-232 (1998), which is incorporated herein by reference in its entirety). Several suitable rolling circle amplification methods are known in the art. For example, RCA amplifies a circular polynucleotide (e.g., DNA) by polymerase extension of an amplification primer complementary to a portion of the template polynucleotide. This process generates copies of the circular polynucleotide template such that multiple complements of the template sequence arranged end to end in tandem are generated (i.e., a concatemer) locally preserved at the site of the circle formation. In embodiments, the amplifying occurs at isothermal conditions. In embodiments, amplifying includes exponential rolling circle amplification (eRCA). Exponential RCA is similar to the linear process except that it uses a second primer having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5(1994)). In embodiments, the amplifying includes hybridization chain reaction (HCR). HCR uses a pair of complementary, kinetically trapped hairpin oligomers to propagate a chain reaction of hybridization events, as described in Dirks, R. M., & Pierce, N. A. (2004) PNAS USA, 101(43), 15275-15278, which is incorporated herein by reference for all purposes. In embodiments, the amplifying includes branched rolling circle amplification (BRCA); e.g., as described in Fan T, Mao Y, Sun Q, et al. Cancer Sci. 2018; 109:2897-2906, which is incorporated herein by reference in its entirety. In embodiments, the amplifying includes hyberbranched rolling circle amplification (HRCA). Hyperbranched RCA uses a second primer complementary to the first amplification product. This allows products to be replicated by a strand-displacement mechanism, which yields drastic amplification within an isothermal reaction (Lage et al., Genome Research 13:294-307 (2003), which is incorporated herein by reference in its entirety). In embodiments, amplifying includes polymerase extension of an amplification primer. In embodiments, the polymerase is T4, T7, Sequenase, Taq, Klenow, and Pol I DNA polymerases. SD polymerase, Bst large fragment polymerase, or a phi29 polymerase or mutant thereof. In embodiments, the polymerase is a strand-displacing polymerase. In embodiments, the strand-displacing polymerase is phi29 polymerase, phi29 mutant polymerase or a thermostable phi29 mutant polymerase. A "phi polymerase" (or "Φ29 polymerase") is a DNA polymerase from the Φ29 phage or from one of the related phages that, like Φ29, contain a terminal protein used in the initiation of DNA replication. For example, phi29 polymerases include the B103, GA-1, PZA, Φ15, BS32, M2Y (also known as M2), Nf, G1, Cp-1, PRD1, PZE, SFS, Cp-5, Cp-7, PR4, PR5, PR722, L17, Φ21, and AV-1 DNA polymerases, as well as chimeras thereof. In embodiments, the polymerase is a phage or bacterial RNA polymerases (RNAPs). In embodiments, the polymerase is a T7 RNA polymerase. In embodiments, the polymerase is an RNA polymerase. Useful RNA polymerases include, but are not limited to, viral RNA polymerases such as T7 RNA polymerase, T3 polymerase, SP6 polymerase, and K11 polymerase; Eukaryotic RNA polymerases such as RNA polymerase I, RNA polymerase II, RNA polymerase III, RNA polymerase IV, and RNA polymerase V; and Archaea RNA polymerase.

In embodiments, amplifying includes extending an amplification primer with a strand-displacing polymerase at a temperature of about 20° C. to about 50° C. In embodiments, the method includes amplifying a template polynucleotide by extending an amplification primer with a strand-displacing polymerase at a temperature of about 30° C. to about 50° C. In embodiments, the method includes amplifying a template polynucleotide by extending an amplification primer with a strand-displacing polymerase at a temperature of about 25° C. to about 45° C. In embodiments, the method includes amplifying a template polynucleotide by extending an amplification primer with a strand-displacing polymerase at a temperature of about 35° C. to about 45° C. In embodiments, the method includes amplifying a template polynucleotide by extending an amplification primer with a strand-displacing polymerase at a temperature of about 35° C. to about 42° C. In embodiments, the method includes amplifying a template polynucleotide by extending an amplification primer with a strand-displacing polymerase at a temperature of about 37° C. to about 40° C. In embodiments, the strand-displacing enzyme is an SD polymerase, Bst large fragment polymerase, or a phi29 polymerase or mutant thereof. In embodiments, the strand-displacing polymerase is phi29 polymerase, phi29 mutant polymerase or a thermostable phi29 mutant polymerase. In embodiments, amplifying includes a plurality of cycles of strand denaturation, primer hybridization, and primer extension.

In embodiments, the methods provided herein include sequencing that includes (a) amplifying the tagged complements of the plurality of sample polynucleotides thereby making amplified products; (b) fragmenting the amplified products to produce fragments, (c) ligating adapters to the fragments, (d) amplifying the resultant products from step (c) to generate a polynucleotide, and (e) performing a sequencing reaction on the polynucleotide from step (d). In embodiments, the amplification method in step (a) is different than the amplification method in step (d). For example, the amplification method in step (a) includes solution phase amplification and the amplification method in step (d) includes solid phase amplification. In embodiments, the adapters have a length of 10 to 50 nucleotides. For example, an adapter may have a length of 10 to 40, 10 to 30, 10 to 20, 25 to 50, 15 to 40, 15 to 30, 20 to 50, 20 to 40, or 20 to 30 nucleotides. In some embodiments, the adapter has a length of 18 to 24 nucleotides. Examples of adapters include, but are not limited to, P5, P7, PE1, PE2, A19, or others known in the art and as provided in commercial kits.

In embodiments, sequencing includes: (a) fragmenting the amplified products to produce fragments, (b) ligating adapters to the fragments, (c) amplifying the resultant products from step (b) to generate a polynucleotide, and (d) performing a sequencing reaction on the polynucleotide from step (c). In embodiments, the sequencing reaction includes (i) immobilizing a polynucleotide to be sequenced on a solid support; (ii) hybridizing a sequencing primer to the immobilized polynucleotide; (iii) performing cycles of primer extension with a polymerase and labeled nucleotides to generate an extended sequencing primer and (iv) detecting the labeled nucleotides to determine the sequence of the immobilized polynucleotide. In embodiments, sequencing further includes (a) producing a plurality of sequencing reads; (b) grouping sequencing reads based on co-occurrence of barcode sequences; and (c) within each group, aligning the reads that belong to the same strand of an original sample polynucleotide based on the sequences of the barcode sequences (see for example FIG. 14).

In embodiments, the methods provided herein include sequencing that includes a sequencing reaction. The sequencing reaction includes (i) immobilizing a polynucleotide to be sequenced on a solid support; (ii) hybridizing a sequencing primer to the immobilized polynucleotide; (iii) performing cycles of primer extension with a polymerase (e.g., a sequencing polymerase) and labeled nucleotides to generate an extended sequencing primer; and (iv) detecting the labeled nucleotides to determine the sequence of the immobilized polynucleotide. In embodiments, the sequencing polymerase is a Taq polymerase, Therminator γ, 9° N polymerase (exo-), Therminator II, Therminator III, or Therminator IX. In embodiments, the sequencing polymerase is Therminator γ. In embodiments, the sequencing polymerase is 9° N polymerase (exo-). In embodiments, the sequencing polymerase is Therminator II. In embodiments, the sequencing polymerase is Therminator III. In embodiments, the sequencing polymerase is Therminator IX. In embodiments, the sequencing polymerase is a Taq polymerase. In embodiments, the sequencing polymerase is a sequencing polymerase. In embodiments, the sequencing polymerase is 9°N and mutants thereof. In embodiments, the sequencing polymerase is Phi29 and mutants thereof. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, both of which are incorporated by reference herein). In embodiments, the polymerase is DNA polymerase, a terminal deoxynucleotidyl transferase, or a reverse transcriptase. In embodiments, the enzyme is a DNA polymerase, such as DNA polymerase 812 (Pol 812) or DNA polymerase 1901

(Pol 1901), e.g., a polymerase described in US 2020/0131484, and US 2020/0181587, both of which are incorporated by reference herein.

In embodiments, the sequencing polymerase is a bacterial DNA polymerase, eukaryotic DNA polymerase, archaeal DNA polymerase, viral DNA polymerase, or phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, λ, σ, μ, and k, as well as the Revl polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. In embodiments, the polymerase is 3PDX polymerase as disclosed in U.S. Pat. No. 8,703,461, the disclosure of which is incorporated herein by reference. In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, or Telomerase reverse transcriptase.

A variety of sequencing methodologies can be used such as sequencing—by synthesis (SBS), pyrosequencing, sequencing by ligation (SBL), or sequencing by hybridization (SBH). In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting of steps. In embodiments, the methods include sequencing one or more bases of a target polynucleotide by extending a sequencing primer hybridized to a target polynucleotide. In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Sequencing can be carried out using any suitable sequencing-by-synthesis (SBS) technique, wherein modified nucleotides are added successively to a free 3' hydroxyl group, typically initially provided by a sequencing primer, resulting in synthesis of a polynucleotide chain in the 5' to 3' direction. In embodiments, sequencing includes detecting a sequence of signals. In embodiments, sequencing includes extension of a sequencing primer with labeled nucleotides. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging.

Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by N nucleotides, thereby detecting a sequence of length N. Example SBS procedures, fluidic systems and detection platforms that can be readily adapted for use with an array produced by the methods of the present disclosure are described, for example, in Bentley et al., Nature 456: 53-59 (2008), US 2018/0274024, WO 2017/205336, US 2018/0258472, each of which are incorporated herein in their entirety for all purposes.

In embodiments, sequencing includes a plurality of sequencing cycles. In embodiments, sequencing includes 20 to 100 sequencing cycles. In embodiments, sequencing includes 50 to 100 sequencing cycles. In embodiments, sequencing includes 50 to 300 sequencing cycles. In embodiments, sequencing includes 50 to 150 sequencing cycles. In embodiments, sequencing includes 50 to 100 sequencing cycles. In embodiments, sequencing includes at least 10, 20, 30 40, or 50 sequencing cycles. In embodiments, sequencing includes at least 10 sequencing cycles. In embodiments, sequencing includes 10 to 20 sequencing cycles. In embodiments, sequencing includes 10, 11, 12, 13, 14, or 15 sequencing cycles. In embodiments, sequencing includes (a) extending a sequencing primer by incorporating a labeled nucleotide, or labeled nucleotide analogue and (b) detecting the label to generate a signal for each incorporated nucleotide or nucleotide analogue.

In embodiments, sequencing includes extending a sequencing primer to generate a sequencing read. In embodiments, sequencing includes extending a sequencing primer by incorporating a labeled nucleotide, or labeled nucleotide analogue and detecting the label to generate a signal for each incorporated nucleotide or nucleotide analogue. In embodiments, the labeled nucleotide or labeled nucleotide analogue includes a reversible terminator moiety.

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

In embodiments, the methods provided herein include sequencing that further includes (a) producing a plurality of sequencing reads; (b) aligning a portion of each sequencing read to a reference sequence; and (c) grouping sequencing reads that belong to the same strand of an original sample polynucleotide based on the aligning and sequences of the barcode sequences.

In embodiments, the methods of making tagged complements provided herein include any sequencing method known to those skilled in the art and include for example, sequencing by synthesis, pyrosequencing, combinatorial probe anchor synthesis, sequencing by ligation, and nanopore sequencing. In embodiments, the sequencing reaction includes sequencing by synthesis, sequencing by ligation, or pyrosequencing. In embodiments, the sequencing reaction includes sequencing by synthesis. In embodiments, the sequencing reaction includes sequencing by ligation. In embodiments, the sequencing reaction includes pyrosequencing.

In embodiments, the methods of making and sequencing tagged complements provided herein include producing a plurality of sequencing reads. In embodiments, each sequencing read includes at least a portion (e.g., a barcode sequence) of two or more interposing oligonucleotide barcodes, or complements thereof. In embodiments, each sequencing read includes at least a portion (e.g., a barcode sequence) of three or more interposing oligonucleotide barcodes, or complements thereof. In embodiments, each sequencing read includes two or more interposing oligonucleotide barcodes, or complements thereof. In embodiments, each sequencing read includes three or more interposing oligonucleotide barcodes, or complements thereof. In embodiments, each sequencing read includes a portion of two or more interposing oligonucleotide barcodes, or complements thereof. In embodiments, each sequencing read includes a portion of two or more interposing oligonucleotide barcodes, or complements thereof. In embodiments, each sequencing read includes at least a portion of three interposing oligonucleotide barcodes, or complements thereof.

In embodiments, the methods of making and sequencing tagged complements provided herein include aligning a portion of each sequencing read to a reference sequence. General methods for performing sequence alignments are known to those skilled in the art. Examples of suitable alignment algorithms, include but are not limited to Burrows-Wheeler Aligner (BWA), Bowtie, the Needleman-Wunsch algorithm (see e.g. the EMBOSS Needle aligner available at www.ebi.ac.uk/Tools/psa/emboss_needle/, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/, optionally with default settings). Optimal alignment may be assessed using any suitable parameters of a chosen algorithm, including default parameters. In embodiments, the reference sequence is a reference genome. In embodiments, the methods of sequencing a template nucleic acid further include generating overlapping sequence reads and assembling them into a contiguous nucleotide sequence of a nucleic acid of interest. Assembly algorithms known in the art can align and merge overlapping sequence reads generated by methods of several embodiments herein to provide a contiguous sequence of a nucleic acid of interest. A person of ordinary skill in the art will understand which sequence assembly algorithms or sequence assemblers are suitable for a particular purpose taking into account the type and complexity of the nucleic acid of interest to be sequenced (e.g. genomic, PCR product, or plasmid), the number and/or length of deletion products or other overlapping regions generated, the type of sequencing methodology performed, the read lengths generated, whether assembly is de novo assembly of a previously unknown sequence or mapping assembly against a backbone sequence, etc. Furthermore, an appropriate data analysis tool will be selected based on the function desired, such as alignment of sequence reads, base-calling and/or polymorphism detection, de novo assembly, assembly from paired or unpaired reads, and genome browsing and annotation. In several embodiments, overlapping sequence reads can be assembled by sequence assemblers, including but not limited to ABySS, AMOS, Arachne WGA, CAP3, PCAP, Celera WGA Assembler/CABOG, CLC Genomics Workbench, CodonCode Aligner, Euler, Euler-sr, Forge, Geneious, MIRA, miraEST, NextGENe, Newbler, Phrap, TIGR Assembler, Sequencher, SeqMan NGen, SHARCGS, SSAKE, Staden gap4 package, VCAKE, Phusion assembler, Quality Value Guided SRA (QSRA), Velvet (algorithm), SPAdes, and the like. It will be understood that overlapping sequence reads can also be assembled into contigs or the full contiguous sequence of the nucleic acid of interest by available means of sequence alignment, computationally or manually, whether by pairwise alignment or multiple sequence alignment of overlapping sequence reads. Algorithms suited for short-read sequence data may be used in a variety of embodiments, including but not limited to Burrows-Wheeler Aligner (BWA), Cross_match, ELAND, Exonerate, MAQ, Mosaik, RMAP, SHRiMP, SOAP, SPAdes, SSAHA2, SXOligoSearch, ALLPATHS, Edena, Euler-SR, SHARCGS, SHRAP, SSAKE, VCAKE, Velvet, PyroBayes, PbShort, and ssahaSNP. In embodiments, aligning to a reference sequence is useful to validate the approaches described herein.

In embodiments, the methods of making and sequencing tagged complements provided herein further include forming a consensus sequence for reads having the same interposing oligonucleotide barcode, or a portion thereof (e.g., a barcode sequence). In embodiments, the consensus sequence is obtained by comparing all sequencing reads aligning at a given nucleotide position (optionally, only among those reads identified as originating from the same sample polynucleotide molecule), and identifying the nucleotide at that position as the one shared by a majority of the aligned reads.

In embodiments, the methods of making and sequencing tagged complements described herein further include computationally reconstructing sequences of a plurality of individual strands of original sample polynucleotides by removing interposing oligonucleotide barcode-derived sequences and joining sequences for adjacent portions of the sample polynucleotide. Reconstruction can be performed on individual reads, or on consensus sequences produced from those reads. In embodiments, the methods of making and sequencing tagged complements described herein further include aligning computationally reconstructed sequences.

A variety of suitable sequencing platforms are available for implementing methods disclosed herein (e.g., for performing the sequencing reaction). Non-limiting examples include SMRT (single-molecule real-time sequencing), ion semiconductor, pyrosequencing, sequencing by synthesis, combinatorial probe anchor synthesis, SOLiD sequencing (sequencing by ligation), and nanopore sequencing. Sequencing platforms include those provided by Illumina® (e.g., the HiSeq™, MiSeq™ and/or Genome Analyzer™ sequencing systems); Ion Torrent™ (e.g., the Ion PGM™ and/or Ion Proton™. sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems). See, for example U.S. Pat. Nos. 7,211,390; 7,244,559; 7,264,929; 6,255,475; 6,013,445; 8,882,980; 6,664,079; and 9,416,409.

In an aspect is provided a method of sequencing a target nucleic acid. In embodiments, the method includes combining a sample polynucleotide (e.g., a polynucleotide containing the target nucleic acid sequence), hybridizing a plurality of interposing oligonucleotide barcodes (e.g., the interposing oligonucleotide barcodes as described herein) to the sample polynucleotide, extending the 3' ends of the hybridization pad (e.g., the available second hybridization pad) with a polymerase to create an extension product, ligating the 3' end of the extension product with the 5' end of an adjacent hybridization pad (e.g., the first hybridization pad of an adjacent interposing oligonucleotide barcode) hybridized to the sample polynucleotide to generate a complement of the sample polynucleotide including a plurality of interposing oligonucleotide barcodes (see for example FIG. 2C), amplifying the complement to generate an amplified product, fragmenting the amplified product to produce fragments, sequencing the fragments to produce a plurality of sequence reads, assembling the sequence reads to produce an assembled sequence of the target nucleic acid. In embodiments, following fragmentation, the fragments are subjected to standard library preparation methods as known to those skilled in the art and described herein. For example, the method includes ligating adapters (e.g., platform specific oligonucleotide sequences) to the fragments, amplifying the resultant products (i.e., the fragments containing adapters) to generate a plurality of polynucleotides.

In embodiments, assembling the sequence reads includes grouping the sequencing reads based on co-occurrence of barcode sequences of the interposing oligonucleotide barcodes. In embodiments, the assembling further includes aligning the reads within each group that belong to the same strand of an original sample polynucleotide based on the sequences of the barcode sequences.

In an aspect is a method of identifying a pseudogene in a sample polynucleotide. The method includes i) amplifying tagged complements of a plurality of sample polynucleotides as described herein, wherein the sample polynucleotide includes a pseudogene nucleic acid sequence; ii) sequencing the amplified products to generate a plurality of sequencing reads; (iii) generating overlapping sequence reads and assembling them into a contiguous nucleotide sequence; (iv) aligning the contiguous nucleotide sequence to a reference sequence containing a parent gene; and (v) identifying a pseudogene in a sample polynucleotide when the contiguous nucleotide sequence includes a disruption in the sequence relative to the parent gene (e.g., a missing promotor, missing start codon, frameshift, premature stop codon, missing introns, or partial deletion). In embodiments, the method include distinguishing a pseudogene from a parent gene in a sample polynucleotide.

In embodiments, sample polynucleotide includes a ABCC6 pseudogene, ADAMTSL2 pseudogene, ANKRD11 pseudogene, BMPR1A pseudogene, CORO1A pseudogene, COX10 pseudogene, CSF2RA pseudogene, CYP21A2 pseudogene, DHFR pseudogene, F8 pseudogene, FOXD4 pseudogene, GK pseudogene, HYDIN pseudogene, IDS pseudogene, NCF1 pseudogene, NEB pseudogene, NOTCH2 pseudogene, OCLN pseudogene, OTOA pseudogene, PIK3CA pseudogene, PKD1 pseudogene, PMS2 pseudogene, PTEN pseudogene, RBM8A pseudogene, SHOX pseudogene, SMN1 pseudogene, SMN2 pseudogene, STRC pseudogene, TTN pseudogene, TUBB2A pseudogene, TUBB2B pseudogene, USP18 pseudogene, HBA1/HBA2 pseudogene, CHEK2 pseudogene, SMN1/SMN2 pseudogene, PMS2 pseudogene, BRAF exon 18 pseudogene, GBA pseudogene, or SDHA pseudogene. In embodiments, the sample polynucleotide includes a HBA1/HBA2 pseudogene, CHEK2 pseudogene, SMN1/SMN2 pseudogene, PMS2 pseudogene, BRAF exon 18 pseudogene, GBA pseudogene, or SDHA pseudogene.

Tagged Polynucleotides

In an aspect, provided herein are polynucleotides including a plurality of units, where each unit includes a portion of a genomic sequence, or a complement thereof, and a sequence of an interposing oligonucleotide barcode. Each of the interposing oligonucleotide barcodes are as described herein, including embodiments. In embodiments, each interposing oligonucleotide barcode includes from 5' to 3': (a) a first stem region including a sequence common to the plurality of interposing oligonucleotide barcodes; (b) a loop region; and (c) a second stem region including a sequence complementary to the first stem region, where the second stem region hybridizes to the first stem region during said hybridizing. In embodiments, each interposing oligonucleotide barcode includes from 5' to 3': (a) a first stem region including a sequence common to the plurality of interposing oligonucleotide barcodes; (b) a loop region including a barcode sequence, wherein each barcode sequence in the polynucleotide is different; and (c) a second stem region including a sequence complementary to the first stem region, where the second stem region hybridizes to the first stem region during said hybridizing.

In embodiments, the polynucleotides provided herein include three or more units. In embodiments, the polynucleotides provided herein include four or more units. In embodiments, the polynucleotides provided herein include five or more units. In embodiments, the polynucleotides provided herein include six or more units. In embodiments, the polynucleotides provided herein include three units. In embodiments, the polynucleotides provided herein include four units. In embodiments, the polynucleotides provided herein include five units. In embodiments, the polynucleotides provided herein include six units. In embodiments, the polynucleotides provided herein include seven units. In embodiments, the polynucleotides provided herein include eight units. In embodiments, the polynucleotides provided herein include nine units. In embodiments, the polynucleotides provided herein include ten units. In embodiments, the polynucleotides provided herein include 5 to 15 units. In embodiments, the polynucleotides provided herein include 4 to 8 units.

In embodiments, the polynucleotides including a plurality of units provided herein, where each unit includes a portion of a genomic sequence (e.g., a gene or gene fragment) and a sequence of an interposing oligonucleotide barcode, include interposing oligonucleotide barcode according to any aspect or embodiment described herein.

In embodiments, the polynucleotides including a plurality of units provided herein, where each unit includes a portion of a genomic sequence and a sequence of an interposing oligonucleotide barcode, includes interposing barcodes that include a first and second hybridization pad. In embodiments, each hybridization pad includes about 3 to about 5 nucleotides of random sequence. In embodiments, each hybridization pad includes about 5 to about 15 nucleotides of random sequence. In embodiments, each hybridization pad includes about 8 to about 12 nucleotides of random sequence. In embodiments, the interposing barcodes provided herein include a hybridization pad that includes 3 nucleotides. In embodiments, the interposing barcodes provided herein include a hybridization pad that includes 4 nucleotides. In embodiments, the interposing barcodes provided herein include a hybridization pad that includes 5 nucleotides.

In embodiments, the polynucleotides including a plurality of units provided herein, where each unit includes a portion of a genomic sequence and an interposing oligonucleotide barcode, include interposing oligonucleotide barcodes that include a first and second stem region. In embodiments, the first and second stem regions are complementary. In embodiments, each stem region includes a known sequence of about 5 to about 10 nucleotides. In embodiments of the interposing oligonucleotide barcodes provided herein, the first stem region includes about 5 nucleotides. In embodiments of the interposing oligonucleotide barcodes provided herein, the first stem region includes about 10 nucleotides. In embodiments of the interposing oligonucleotide barcodes provided herein, the second stem region includes about 5 nucleotides. In embodiments of the interposing oligonucleotide barcodes provided herein, the second stem region includes about 10 nucleotides.

In embodiments, the polynucleotides including a plurality of units provided herein, where each unit includes a portion of a genomic sequence and a sequence of an interposing oligonucleotide barcode. In embodiments, the interposing oligonucleotide barcode includes a barcode sequence. In embodiments, the barcode sequence includes about 5 to about 20 nucleotides. In embodiments, the barcode sequence includes about 5 nucleotides. In embodiments, the barcode sequence includes about 6 nucleotides. In embodiments, the barcode sequence includes about 7 nucleotides. In embodiments, the barcode sequence includes about 8 nucleotides. In embodiments, the barcode sequence includes about 9 nucleotides. In embodiments, the barcode sequence includes about 10 nucleotides. In embodiments, the barcode sequence includes about 11 nucleotides. In embodiments, the barcode sequence includes about 12 nucleotides. In embodiments, the barcode sequence includes about 13 nucleotides. In embodiments, the barcode sequence includes about 14 nucleotides. In embodiments the barcode sequence includes about 15 nucleotides. In embodiments, the barcode sequence includes about 16 nucleotides. In embodiments, the barcode sequence includes about 17 nucleotides. In embodiments, the barcode sequence includes about 18 nucleotides. In embodiments, the barcode sequence includes about 19 nucleotides. In embodiments, the barcode sequence includes about 20 nucleotides.

In embodiments, the interposing oligonucleotide barcode includes a barcode sequence. In embodiments, each barcode sequence is selected from a set of barcode sequences represented by a random or partially random sequence. In embodiments, each barcode sequence is selected from a set of barcode sequences represented by a random sequence. In embodiments, each barcode sequence is selected from a set of barcode sequences represented by a partially random sequence. In embodiments, each barcode sequence includes a random sequence. In embodiments, the random sequence excludes a subset of sequences, where the excluded subset includes sequences with three or more identical consecutive nucleotides. In embodiments, the excluded subset includes sequences with three identical consecutive nucleotides. In embodiments, the excluded subset includes sequences with four identical consecutive nucleotides (e.g., GGGG). In embodiments, the excluded subset includes sequences with five identical consecutive nucleotides (e.g., GGGGG).

In embodiments, the polynucleotides including a plurality of units provided herein, where each unit includes a portion of a genomic sequence and a sequence of an interposing oligonucleotide barcode, includes an interposing oligonucleotide barcode that includes a first stem region and second stem region that further include a sample index sequence. In embodiments, the loop region of the interposing oligonucleotide barcode includes a sample index sequence. A sample index sequence includes a sample index sequence according to any aspect described herein.

In embodiments, each barcode sequence differs from every other barcode sequence by at least two nucleotide positions. In embodiments, the interposing oligonucleotide barcodes provided herein include barcode sequences where each barcode sequence differs from every other barcode sequence by at least three nucleotide positions. In embodiments, the interposing oligonucleotide barcodes provided herein include barcode sequences where each barcode sequence differs from every other barcode sequence by at least four nucleotide positions. In embodiments, the interposing oligonucleotide barcodes provided herein include a barcode sequence where each barcode sequence differs from every other barcode sequence by at least five nucleotide positions.

In embodiments, the polynucleotides including a plurality of units provided herein, where each unit includes a portion of a genomic sequence and a sequence of an interposing oligonucleotide barcode, where the interposing oligonucleotide barcodes include a 5' phosphate moiety.

Kits

In an aspect, provided herein are kits including one or more components of any of the various methods or compositions disclosed herein. In embodiments, the kit includes a plurality of interposing oligonucleotide barcodes that include from 5' to 3': (a) a first stem region including a sequence common to the plurality of interposing oligonucleotide barcodes; (b) a loop region; and (c) a second stem region including a sequence complementary to the first stem region, where the second stem region hybridizes to the first stem region during said hybridizing. In embodiments, the kit includes a plurality of interposing oligonucleotide barcodes that include from 5' to 3': (a) a first stem region including a sequence common to the plurality of interposing oligonucleotide barcodes; (b) a loop region including a barcode sequence, wherein each barcode sequence in the polynucleotide is different; and (c) a second stem region including a sequence complementary to the first stem region, where the second stem region hybridizes to the first stem region during said hybridizing. In embodiments, the kit further includes instructions for use thereof. In embodiments, kits described herein include a polymerase. In embodiments, the polymerase is a DNA polymerase.

Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, labeled nucleotides, and/or modified nucleotides), buffers, salts, and/or labels (e.g., fluorophores). In embodiments, the kit includes components useful for ligating polynucleotides using a ligation enzyme (e.g., CircLigase™ enzyme, Taq DNA Ligase, HiFi Taq DNA Ligase, T4 DNA ligase, T4 RNA ligase, T4 RNA ligase 2, or Ampligase® DNA Ligase). For example, such a kit further includes the following components: (a) reaction buffer for controlling pH and providing an optimized salt composition for a ligation enzyme (e.g., CircLigase™ enzyme, Taq DNA Ligase, HiFi Taq DNA Ligase, T4 DNA ligase, T4 RNA ligase 2, or Ampligase® DNA Ligase), and (b) ligation enzyme cofactors, such as ATP and a divalent ion (e.g., $Mn^{2+}$ or $Mg^{2+}$).

In embodiments, the polymerase in the kit is a bacterial DNA polymerase, eukaryotic DNA polymerase, archaeal DNA polymerase, viral DNA polymerase, or phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases $\alpha$, $\beta$, $\gamma$, $\delta$, $\epsilon$, $\eta$, $\zeta$, $\lambda$, $\sigma$, $\mu$, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus* zilligi (Tzi) DNA polymerase, *Thermus thermophilus* (Tth) DNA polymerase, *Thermus* flavusu (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus* gorgonarius (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus* fumicolans DNA polymerase; *Aeropyrum pernix* DNA polymerase; and the heterodimeric DNA polymerase DP1/DP2. In embodiments, the polymerase is 3PDX polymerase as disclosed in U.S. Pat. No. 8,703,461, the disclosure of which is incorporated herein by reference. In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, or Telomerase reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, Bicine, Tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid. In embodiments, the buffer includes PEG (polyethylene glycol), PVP (polyvinylpyrrolidone), trehalose, ficoll, or dextran. In embodiments, the buffer includes additives such as Tween-20 or NP-40.

In embodiments, the kit includes a sequencing reaction mixture. As used herein, the term "sequencing reaction mixture" is used in accordance with its plain and ordinary meaning and refers to an aqueous mixture that contains the reagents necessary to allow a nucleotide or nucleotide analogue to be added to a DNA strand by a DNA polymerase.

Adapters, interposing oligonucleotide barcodes, and/or primers may be supplied in the kits ready for use, or more preferably as concentrates-requiring dilution before use, or even in a lyophilized or dried form requiring reconstitution prior to use. If required, the kits may further include a supply of a suitable diluent for dilution or reconstitution of the primers. Optionally, the kits may further include supplies of reagents, buffers, enzymes, and dNTPs for use in carrying out nucleic acid amplification and/or sequencing. Further components which may optionally be supplied in the kit include sequencing primers suitable for sequencing templates prepared using the methods described herein.

EXAMPLES

Example 1: Experimental Rationale

Described herein are methods pertaining to sequencing a nucleic acid. Traditional sequencing-by-synthesis (SBS) methodologies employ serial incorporation and detection of labeled nucleotide analogues. For example, high-throughput SBS technology (see, for example, Bentley D R, et al. Nature, 2008, 456, 53-59) uses cleavable fluorescent nucleotide reversible terminator (NRT) sequencing chemistry (see, for example, see U.S. Pat. No. 6,664,079; or Ju et al. Proc. Natl. Acad. Sci. USA, 2006, 103, 19635-19640). These cleavable fluorescent NRTs were designed based on the following rationale: each of the four nucleotides (A, C, G, T, and/or U) is modified by attaching a unique cleavable fluorophore to the specific location of the nucleobase and capping the 3'-OH group of the nucleotide sugar with a small reversible moiety (also referred to herein as a reversible terminator) so that they are still recognized by DNA polymerase as substrates. The reversible terminator temporarily halts the polymerase reaction after nucleotide incorporation while the fluorophore signal is detected. After incorporation and signal detection, the fluorophore and the reversible terminator is cleaved to resume the polymerase reaction in the next cycle.

These traditional SBS techniques require de novo assembly of relatively short lengths of DNA (e.g., 35 to 300 base pairs), which makes resolving complex regions with mutations or repetitive sequences difficult. The application of those technologies to de-novo genome assemblies is limited by short sequence read length, which, by previous methods, is insufficient to resolve complex genome structure and to produce consistent genome assembly. To address these limitations, researchers typically supplement short read sequencing data (e.g., short read sequencing data having an error rate of less than about 1.5%) with data from long read sequencers (e.g., read length 10 kb, error rate 10-15%). Further, it is difficult to reliable obtain phasing data (i.e., which variants are on the same chromosome) or detecting structural variants from short read data. Described herein are methods for achieving greater read lengths by utilizing specialized interposing oligonucleotide barcodes.

Inheritance patterns of genetic variation in complex traits may be influenced by interactions among multiple genes and alleles across long distances. Examination of phased variants are critical for a greater understanding of the genetic basis of complex phenotypes (see, for example, Snyder, M. W., Adey, A., Kitzman, J. O. & Shendure, J. "Haplotype-resolved genome sequencing: experimental methods and applications" Nat. Rev. Genet. 16, 344-358 (2015)). Additionally, resolving long-range information at the molecular level within complex samples, e.g., cancer samples, is essential to assemble and phase variants of subpopulations of cells, as genetic drivers and important diagnostic biomarkers in cancers and other diseases (see, for example, Moncunill, V. et al. Comprehensive characterization of complex structural variations in cancer by directly comparing genome sequence reads. Nat. Biotechnol. 32, 1106-1112 (2014)). Experiments herein demonstrate that long-ranged nucleic acid sequencing can be performed in one physical compartment. Embodiments herein provide certain advantages over other methods, such as those described in US 2013/0079231A1.

Example 2: T-Cell and B-Cell Receptor Repertoire Sequencing

Applications of NGS to genomes, transcriptomes, and epigenomes may be applied to immune profiling. The functions of immune cells such as B- and T-cells are predicated on the recognition through specialized receptors of specific targets (antigens) in pathogens. There are approximately $10^{10}$ to $10^{11}$ B-cells and $10^{11}$ T-cells in a human adult (see, for example, Ganusov V V, De Boer R J. Trends Immunol. 2007; 28(12):514-8; and Bains I, Antia R, Callard R, Yates A J. Blood. 2009; 113(22):5480-5487).

Immune cells are critical components of adaptive immunity and directly bind to pathogens through antigen-binding regions present on the cells. Within lymphoid organs (e.g., bone marrow for B cells and the thymus for T cells) the gene segments variable (V), joining (J), and diversity (D) rearrange to produce a novel amino acid sequence in the antigen-binding regions that allow for the recognition of antigens from a range of pathogens (e.g., bacteria, viruses, parasites, and worms) as well as antigens arising from cancer cells. The large number of possible V-D-J segments, combined with additional (junctional) diversity, lead to a theoretical diversity of $>10^{14}$, which is further increased during adaptive immune responses. Overall, the result is that each B- and T-cell expresses a highly variable receptor, whose sequence is the outcome of both germline diversity and somatic recombination. Somatic recombination is a process that creates new combinations of V, D and J segments via a complicated mechanism that involves gene excision and alternative splicing. These antibodies also contain a constant (C) region, which confers the isotype to the antibody. In most mammals, there are five antibody isotypes: IgA, IgD, IgE, IgG, and IgM. For example, each antibody in the IgA isotype shares the same constant region. Characterization of an individual's immune repertoire (i.e., the global profile of which immune cell receptors are present in an individual), requires full length sequencing of the recombined VDJ region, which is difficult to determine with short read sequencing data. Thus, obtaining long-range sequence data is incredibly insightful to gain insights into the adaptive immune response in healthy individuals and in those with a wide range of diseases.

For example, while parts of the B-cell immunoglobulin receptor (BCR) can be traced back to segments encoded in the germline (i.e., the V, D and J segments), the set of segments used by each receptor is something that needs to be determined as it is coded in a highly repetitive region of the genome (see, for example, Yaari G, Kleinstein S H. Practical guidelines for B-cell receptor repertoire sequencing analysis. Genome Med. 2015; 7:121. (2015)). Additionally, there are no pre-existing full-length templates to align the sequencing reads.

Sample library preparation involves the isolation and amplification of the target nucleic acid fragments for sequencing. There are two starting materials that can serve as the initial template to sequence immunoglobulin (Ig) repertoires-genomic DNA (gDNA) and mRNA. Use of gDNA as a template has particular advantages over mRNA when alternative splicing does not take place, namely using mRNA requires an additional step to convert RNA to DNA via reverse transcription. However, within a cell, there is a single copy of gDNA, whereas the quantity of mRNA varies by orders of magnitude. Regardless, either gDNA or mRNA can serve as input.

Briefly, an example interposing barcode is shown in FIG. 1A, and includes a loop region, a stem region, and two hybridization pads. The loop region includes about 10 to about 20 random nucleotides (e.g., AGCCTGCCTG (SEQ ID NO: 7)). Such random sequences may be referred to as molecular barcodes or unique molecular identifiers (UMI). In embodiments of the methods described herein, synthetic long reads are constructed by grouping together UMIs based on direct or indirect co-occurrence in the library, and then assembling the reads back into the original full-length molecule. In embodiments, the length of the UMI is optimized based on the total number of insertions sites (number of targeted molecules X number of insertion locations) to reduce the incorporation of two of the same UMIs in different molecules, while maximizing the amount of sequence in the read that is from the target molecule. Rare instances where the same UMI is observed in two different molecules can be addressed bioinformatically.

Figure 1B:
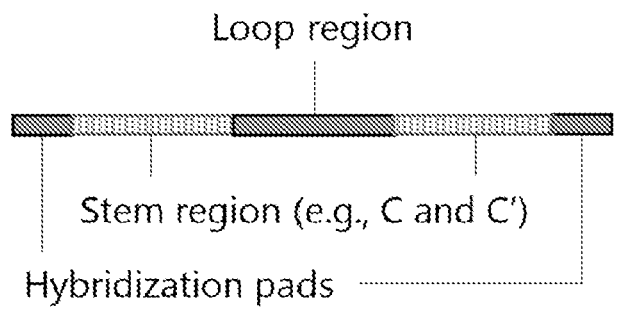

Aside from forming the backbone for long read alignment, the introduction of UMIs into sequencing libraries prior to target amplification by PCR has been shown to dramatically increase the sensitivity for rare mutations and enable absolute read counting. The stem region includes two known sequences capable of hybridizing to each other, ranging from about 5 to about 10 nucleotides, and is stable (i.e., capable to remaining hybridized together) at approximately a maximum temperature of 37° C., and unhybridizes (i.e., denatures) at temperatures greater than 50° C. Finally, the hybridization pads are each about 9 to about 15 nucleotides (e.g., AGTCG for pad 1, and GGGAG for pad 2) and are capable of hybridizing to single stranded template nucleic acids (i.e., they are a complement to the original target). The sequences of the hybridization pad may be random or may include a targeted priming sequence to maximize placement of the IBC. FIG. 1B depicts the interposing barcode when the stem regions are denatured. In embodiments, only Type 1 interposing barcodes are used. In other embodiments, only Type 2 interposing barcodes are used. Alternatively, the hybridization pads can include targeted priming sequences (e.g., nucleotide sequences that are complementary to regions in the constant region that are interspersed between the V, D, and J regions). In this alternative, the interposing barcodes have targeted priming sequences in the hybridization pads, wherein the priming sequences target the constant regions that flank the variable regions.

Figure 2A:
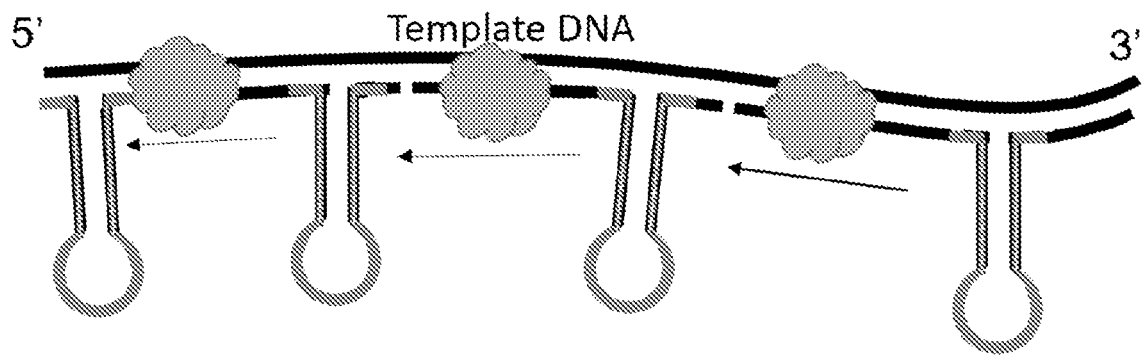
FIGS. 2A-2C illustrates a sequencing process, in accordance with an embodiment described herein.
Figure 2B:
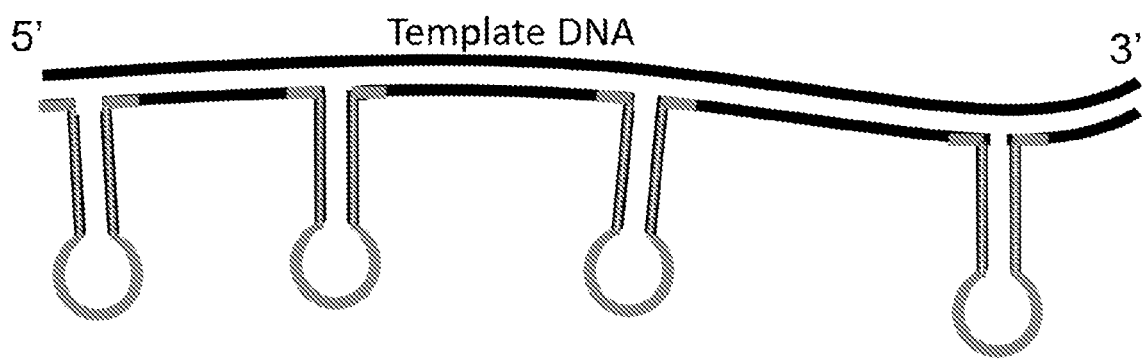

To an isolated DNA (e.g., B-cell immunoglobulin receptor) sample interposing barcodes (as described herein) are added at an appropriate concentration such that there are approximately 50-100 bases between each IBC. A non strand-displacing polymerase (e.g., Klentaq, T4, T7, Bst, Phusion, Tfl, Pfu, or Stoffel fragment) extends the complement strand to generate an extension segment, as shown in FIG. 2A, and a ligase (for example, Taq DNA Ligase, HiFi Taq DNA Ligase, T4 DNA ligase, or Ampligase® DNA Ligase) ligates the ends of the extension segment together with the next interposing barcode to produce a single integrated strand, as depicted in FIG. 2B. For example, a T4 extension-ligation reaction may be carried out by combining the polynucleotide ends, ligation buffer, ATP, T4 DNA ligase, water, and incubating the mixture at between about 20° C. to about 45° C., for between about 5 minutes to about 30 minutes. In embodiments, a T4 extension-ligation reaction may be carried out by combining the polynucleotide ends, ligation buffer, ATP, T4 DNA ligase, water, and incubating the mixture at between about 37° C., for between about 30 minutes to about 90 minutes. In some embodiments, the T4 extension-ligation reaction is incubated at 37° C. for 30 minutes. In some embodiments, the T4 extension-ligation reaction is incubated at 37° C. for 30 to 90 minutes. In some embodiments, the T4 extension-ligation reaction is incubated at 37° C. for 60 minutes. In some embodiments, the T4 extension-ligation reaction is incubated at 45° C. for 30 minutes. In some embodiments, the T4 extension-ligation reaction is incubated at 45° C. for 60 minutes. In embodiments, the ligase reaction is stopped by adding Tris buffer with high EDTA and incubating for 1 minute. The non strand-displacing polymerase can either be a naturally occurring enzyme, or one that is specifically engineered to minimize strand displacement.

As even "non strand-displacing" DNA polymerases can have a slight ability to displace a DNA oligonucleotide from a template strand of DNA, the hybridization of the oligonucleotide can be enhanced in order to stop strand displacement by the polymerase. Prevention of displacement can be achieved by using modifications to the oligonucleotide itself or by using additives that either stabilize the hybridization of the oligonucleotide or that stop the polymerase. Modifications to the oligonucleotides that reduce or inhibit the strand displacement activity of the polymerase are for instance 2' fluoro nucleosides, PNAs (peptide nucleic acids), ZNAs (zip nucleic acids), G-Clamps (U.S. Pat. No. 6,335,439, a cytosine analogue capable of Clamp Binding to Guanine) or LNAs (US 2003/0092905; U.S. Pat. No. 7,084,125). In embodiments, the non strand-displacing polymerase activity can be inhibited by the addition of Actinomycin D. Actinomycin D can be added to the reaction in sufficient amounts to avoid to reduce strand displacement of the polymerase as compared without actinomycin addition. In embodiments, Actinomycin D is added at about 50 μg/ml.

Figure 2C:
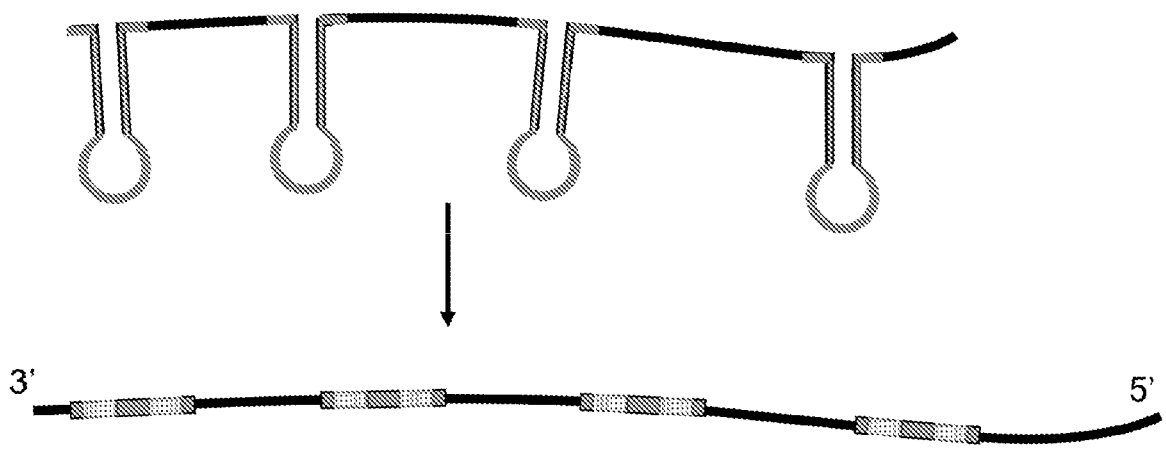

Optionally, the template DNA sample is washed away, and the resultant integrated strand may be subjected to reaction conditions (e.g., elevated temperature or denaturing additives) such that the stem regions of interposing barcodes and/or any secondary structures present denature to form a linear integrated strand, as schematically shown in FIG. 2C. The integrated strand may be amplified using methods known to those skilled in the art (e.g., standard PCR amplification or rolling circle amplification) and subjected to standard library preparation methods as known to those skilled in the art and described herein. Alternatively, the cDNA synthesis occurs in the presence of dUTP such that the template is enzymatically degraded. For example, cleavage and degradation at dUTP sites may be achieved using uracil DNA glycosylase and endonuclease VIII (USER™, NEB, Ipswich, Mass.), as described in U.S. Pat. No. 7,435,572. The integrated strand may serve as the input DNA with any commercially available library preparation kit. A variety of kits for making sequencing libraries from DNA are available commercially. The original template strand does not necessarily need to be removed and washed away. For example, in some applications it may be useful and convenient to take the template strands all the way through the sequencing steps and provide useful information in addition to the IBC tagged strand. See for example, FIG. 5C and the workflow description in Example 8 wherein the original template is not washed away. Library preparation methods are briefly summarized herein (e.g., see Example 8 for additional details). The integrated strand may be fragmented using techniques known to those in the art. Three approaches available to fragment nucleic acid chains include: physical, enzymatic, and chemical. DNA fragmentation is typically done by physical methods (i.e., nebulization, acoustic shearing, and sonication) or enzymatic methods (i.e., non-specific endonuclease cocktails and transposase tagmentation reactions).

Following fragmentation, the DNA fragments are end repaired or end polished. Typical polishing mixtures contain T4 DNA polymerase and T4 polynucleotide kinase. These enzymes excise 3' overhangs, fill in 3' recessed ends, and remove any potentially damaged nucleotides thereby generating blunt ends on the nucleic acid fragments. The T4 polynucleotide kinase used in the polishing mix adds a phosphate to the 5' ends of DNA fragments that can be lacking such, thus making them ligation-compatible to NGS adapters. Generally, a single adenine base is added to form an overhang via an A-tailing reaction. This "A" overhang allows adapters containing a single thymine overhanging base to base pair with the DNA fragments. Additional sequences such as adapters or primers may then be added using conventional means to permit platform specific sequences or to provide a binding site for sequencing primers. Following adapter ligation, the nucleic acid templates may be purified, amplified, or sequenced using methods known to those skilled in the art.

For example, the following protocol is then followed to prepare the integrated strand for sequencing on next generation sequencing devices.

The input DNA (i.e., the integrated strand) is fragmented to make small DNA molecules with a modal size of about 100 to about 400 base pairs with random ends. This is done by sonication, chemical fragmentation, or enzymatic fragmentation. The resulting DNA fragments generated by sonication are end polished to produce a library of DNA fragments with blunt, 5'-phosphorylated ends that are ready for ligation. The end polishing is accomplished by using the T4 DNA polymerase, which can fill in 5' overhangs via its polymerase activity and recess 3' overhangs via its 3'→5' exonuclease activity. The phosphorylation of 5' ends is accomplished by T4 polynucleotide kinase.

Adapter ligation: Ligation of double-stranded DNA adapters is accomplished by use of T4 DNA ligase. Depending on the adapter, some double-stranded adapters may not have 5' phosphates and contain a 5' overhang on one end to prevent ligation in the incorrect orientation.

Now the adapter-ligated library may be size-selected (e.g., selecting for approximately 200-250 base pair size range). By doing this, unligated adapters and adapter dimers are removed, and the optimal size-range for subsequent PCR and sequencing is selected. Adapter dimers are the result of self-ligation of the adapters without an insert sequence. These dimers form clusters very efficiently and consume valuable space on the flow cell without generating any useful data. Thus, known cleanup methods may be used, such as magnetic bead-based clean up, or purification on agarose gels.

Figure 3:
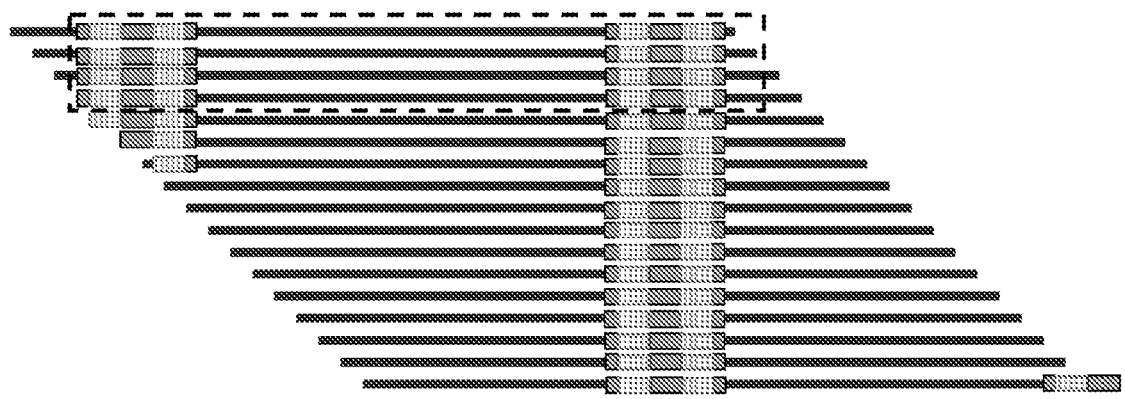
FIG. 3 depicts sequenced strands assembled into contiguous long reads by aligning the IBCs. Shown in the dashed box are instances where two IBCs are present on a single read, thus allowing greater information on the location and origin of the genomic input. The last read shows a complete IBC and a partial IBC on the lower right, conceptually depicting how utilizing embodiments of compositions and methods described herein provide a scaffold for the underlying genomic input.

The resultant strand is then subjected to a nucleic acid sequencing reaction using any available sequencing technology. Once data is available from the sequencing reaction, initial processing (often termed "pre-processing") of the sequences is typically employed prior to annotation. Pre-processing includes filtering out low-quality sequences, sequence trimming to remove continuous low-quality nucleotides, merging paired-end sequences, or identifying and filtering out PCR repeats using known techniques in the art. The sequenced reads may then be assembled and aligned using bioinformatic algorithms known in the art (e.g., as depicted in FIG. 3).

Example 3: Tandem Repeat Expansions

A short tandem repeat is a region of genomic DNA with multiple adjacent copies of short (e.g., 1-6 base) sequence units. These repeat regions are highly mutable due to replication errors that can occur during cell divisions and, importantly, over 30 human diseases are known to be caused by tandem repeat expansions or contractions (see, for example, Tang, H., Kirkness, E. F., Lippert, C., Biggs, W. H., Fabani, M., Guzman, E., et al. (2017). Profiling of short-tandem-repeat disease alleles in 12,632 human whole genomes. Am. J. Hum. Genet. 101, 700-715). Most of the disease-causing expansions are longer than the currently used NGS sequencing devices, making it virtually impossible to accurately assemble those regions of interest using typical sequencing methods.

Variability of the CGG tandem repeat in the 5' untranslated region (UTR) of the fragile X mental retardation gene (FMR1) is associated with various disorders. Whereas most individuals in the general population have around 30 CGG repeats (<45 repeats), patients with fragile X syndrome carry large, full expansions sized above 200 repeats. The intermediate zone (45-54 repeats) exists, and although carriers of intermediate alleles are generally believed to be healthy, some reports have shown that these alleles might be associated with Parkinsonism and fragile X-associated tremor/ataxia syndrome. Complicating matters, researchers have found the presence, location, and quantity of AGG triplets interrupting the repeat can influence the risk of offspring inheriting a disease.

Sequencing can be used to determine the repeat size and the detection of the number of interrupting AGG units utilizing the interposing barcodes as described herein. This data may be used clinically for improved genetic counselling for individuals weighing the risk of having a child with FXS.

Another example where this technology described herein can be useful is the ATTCT repeat embedded in intron 9 of the Spinocerebellar ataxia type 10 gene (SCA10) (see, for example, McFarland K N, Liu J, Landrian I, Godiska R, Shanker S, Yu F, Farmerie W G, Ashizawa T. PLoS One.

2015; 10(8):e0135906). The presence of those interruptions influence the phenotype of SCA10 patients and hence knowing the exact repeat structure allows for better genotype-phenotype correlations.

Briefly, an example interposing barcode is shown in FIG. 1A, and includes a loop region, a stem region, and two hybridization pads. The loop region includes about 10 to about 20 random nucleotides (e.g., TCTAATGATC (SEQ ID NO:8)). Such random sequences are referred to as molecular barcodes or unique molecular identifiers (UMI). In embodiments of the methods described herein, synthetic long reads are constructed by grouping together UMIs based on direct or indirect co-occurrence in the library, and then assembling the reads back into the original full-length molecule. In embodiments, the length of the UMI is optimized based on the total number of insertions sites (number of targeted molecules X number of insertion locations) to reduce the incorporation of two of the same UMIs in different molecules, while maximizing the amount of sequence in the read that is from the target molecule. Rare instances where the same UMI is observed in two different molecules can be addressed bioinformatically.

Aside from forming the backbone for long read alignment, the introduction of UMIs into sequencing libraries prior to target amplification by PCR has been shown to dramatically increase the sensitivity for rare mutations and enable absolute read counting. The stem region includes two known sequences capable of hybridizing to each other, ranging from about 5 to about 10 nucleotides, and is stable (i.e., capable to remaining hybridized together) at approximately a maximum temperature of 37° C., and unhybridizes (i.e., denatures) at temperatures greater than 50° C. Finally, the hybridization pads each includes about 9 to about 15 nucleotides (e.g., ACAGC for pad 1 and CTGCA for pad 2) and are capable of hybridizing to single stranded template nucleic acids (i.e., they are a complement to the original target). The sequences of the hybridization pad may be random or may include a targeted priming sequence to maximize placement of the IBC. FIG. 1B depicts the interposing barcode when the stem regions are denatured.

To an isolated DNA (e.g., UTR of the fragile X mental retardation gene (FMR1) or intron 9 of the Spinocerebellar ataxia type 10 gene (SCA10)) sample interposing barcodes (as described herein) are added at an appropriate concentration such that there are approximately 50-100 bases between each IBC (e.g., see Example 8 for additional details). A non strand-displacing sequencing polymerase (e.g., Klentaq, T4, T7, Bst, Phusion, Tfl, Pfu, or Stoffel fragment) extends the complement strand to generate an extension segment, as shown in FIG. 2A, and a ligase ligates the ends of the extension segment together with the next interposing barcode to produce a single integrated strand, as depicted in FIG. 2B. Optionally, the template DNA sample is washed away, and the resultant integrated strand may be subjected to reaction conditions (e.g., elevated temperature or denaturing additives) such that the stem regions of interposing barcodes and/or any secondary structures present denature to form a linear integrated strand, as schematically shown in FIG. 2C. The integrated strand may be amplified using methods known to those skilled in the art (e.g., standard PCR amplification or rolling circle amplification) and subjected to standard library preparation methods as known to those skilled in the art and described herein.

The input DNA (i.e., the integrated strand) is fragmented to make small DNA molecules with a modal size of about 100 to about 400 base pairs with random ends. This is done by sonication, chemical fragmentation, or enzymatic fragmentation. The resulting DNA fragments generated by sonication will be end polished to produce a library of DNA fragments with blunt, 5'-phosphorylated ends that are ready for ligation. The end polishing is accomplished by using the T4 DNA polymerase, which can fill in 5' overhangs via its polymerase activity and recess 3' overhangs via its 3'-5' exonuclease activity. The phosphorylation of 5' ends is accomplished by T4 polynucleotide kinase.

Adapter ligation: Ligation of double-stranded DNA adapters is accomplished by use of T4 DNA ligase. Depending on the adapter, some double-stranded adapters may not have 5' phosphates and contain a 5' overhang on one end to prevent ligation in the incorrect orientation.

Now the adapter-ligated library may be size-selected (e.g., selecting for approximately 200-250 base pair size range). By doing this, unligated adapters and adapter dimers are removed, and the optimal size-range for subsequent PCR and sequencing is selected. Any suitable clean up method known to those skilled in the art may be used, such as magnetic bead-based clean up, or purification on agarose gels.

The resultant strand is then subjected to a nucleic acid sequencing reaction using any available sequencing technology. Once data is available from the sequencing reaction, initial processing (often termed "pre-processing") of the sequences is typically employed prior to annotation. Pre-processing includes filtering out low-quality sequences, sequence trimming to remove continuous low-quality nucleotides, merging paired-end sequences, or identifying and filtering out PCR repeats using known techniques in the art. The sequenced reads may then be assembled and aligned using bioinformatic algorithms known in the art (e.g., as depicted in FIG. 3).

Example 4. Polymorphic Regions of HLA

Sequencing the human leukocyte antigen (HLA) region, or the human major histocompatibility complex (MHC), is crucial for diagnosing autoimmune disorders and selection of donors in organ and stem cell transplantation. Genes in the region can be highly polymorphic, HLA-B being the most variable with >2000 alleles. The high variability in sequence make this region exceptionally difficult to map with traditional sequencing technology (see, for example, Trowsdale J, Knight J C. Annu Rev Genomics Hum Genet. 2013; 14:301-23).

HLA can be divided into three molecule classes and regions, termed class I, II and III. Considering the Class I genes are approximately 3 kb in length, entire alleles, not simply exons only, can be sequenced using the technology and methods described herein. Class II genes can exceed 10 kb making them more difficult, but still possible with this technology.

Briefly, an example interposing barcode is shown in FIG. 1A, and includes a loop region, a stem region, and two hybridization pads. The loop region includes about 10 to about 20 random nucleotides (e.g., TCACGGCGAA (SEQ ID NO:9)). Such random sequences are referred to as molecular barcodes or unique molecular identifiers (UMI). In embodiments of the methods described herein, synthetic long reads are constructed by grouping together UMIs based on direct or indirect co-occurrence in the library, and then assembling the reads back into the original full-length molecule. In embodiments, the length of the UMI is optimized based on the total number of insertions sites (number of targeted molecules X number of insertion locations) to reduce the incorporation of two of the same UMIs in different molecules, while maximizing the amount of sequence in the read that is from the target molecule. Rare instances where the same UMI is observed in two different molecules can be addressed bioinformatically. Aside from forming the backbone for long read alignment, the introduction of UMIs into sequencing libraries prior to target amplification by PCR has been shown to dramatically increase the sensitivity for rare mutations and enable absolute read counting. The stem region includes two known sequences capable of hybridizing to each other, ranging from about 5 to about 10 nucleotides, and is stable (i.e., capable to remaining hybridized together) at approximately at a maximum temperature of 37° C., and unhybridizes (i.e., denatures) at temperatures greater than 50° C. Finally, the hybridization pads each includes about 9 to about 15 nucleotides (e.g., GACAT for pad 1 and TATAC for pad 2) and are capable of hybridizing to single stranded template nucleic acids (i.e., they are a complement to the original target). The sequences of the hybridization pad may be random or may include a targeted priming sequence to maximize placement of the IBC. FIG. 1B depicts the interposing barcode when the stem regions are denatured.

To an isolated DNA (e.g., HLA-B nucleic acid sequence) sample interposing barcodes (as described herein) are added at an appropriate concentration such that there are approximately 50 to 100 bases between each IBC (e.g., see Example 8 for additional details). A non strand-displacing sequencing polymerase (e.g., Klentaq, T4, T7, Bst, Phusion, Tfl, Pfu, or Stoffel fragment) extends the complement strand to generate an extension segment, as shown in FIG. 2A, and a ligase ligates the ends of the extension segment together with the next interposing barcode to produce a single integrated strand, as depicted in FIG. 2B. Optionally, the template DNA sample is washed away, and the resultant integrated strand may be subjected to reaction conditions (e.g., elevated temperature or denaturing additives) such that the stem regions of interposing barcodes and/or any secondary structures present denature to form a linear integrated strand, as schematically shown in FIG. 2C. The integrated strand may be amplified using methods known to those skilled in the art (e.g., standard PCR amplification or rolling circle amplification) and subjected to standard library preparation methods as known to those skilled in the art and described herein.

For example, the following protocol is then followed to prepare the integrated strand for sequencing on next generation sequencing devices. The input DNA (i.e., the integrated strand) is fragmented to make small DNA molecules with a modal size of about 100 to about 400 base pairs with random ends. This is done by sonication, chemical fragmentation, or enzymatic fragmentation. The resulting DNA fragments generated by sonication will be end polished to produce a library of DNA fragments with blunt, 5'-phosphorylated ends that are ready for ligation. The end polishing is accomplished by using the T4 DNA polymerase, which can fill in 5' overhangs via its polymerase activity and recess 3' overhangs via its 3'-5' exonuclease activity. The phosphorylation of 5' ends is accomplished by T4 polynucleotide kinase.

Adapter ligation: Ligation of double-stranded DNA adapters is accomplished by use of T4 DNA ligase. Depending on the adapter, some double-stranded adapters may not have 5' phosphates and contain a 5' overhang on one end to prevent ligation in the incorrect orientation.

Now the adapter-ligated library may be size-selected (e.g., selecting for approximately 200-250 base pair size range). By doing this, unligated adapters and adapter dimers are removed, and the optimal size-range for subsequent PCR and sequencing is selected. Any suitable clean up method known to those skilled in the art may be used, such as magnetic bead-based clean up, or purification on agarose gels.

The resultant strand is then subjected to a nucleic acid sequencing reaction using any available sequencing technology. Once data is available from the sequencing reaction, initial processing (often termed "pre-processing") of the sequences is typically employed prior to annotation. Pre-processing includes filtering out low-quality sequences, sequence trimming to remove continuous low-quality nucleotides, merging paired-end sequences, or identifying and filtering out PCR repeats using known techniques in the art. The sequenced reads may then be assembled and aligned using bioinformatic algorithms known in the art (e.g., as depicted in FIG. 3).

Example 5: RNA Sequencing Poly(A) Tails

Sequencing RNA (e.g., mRNA, rRNA, and tRNA) allows transcriptome investigation and discovery, and provides useful insight informing scientists which genes are turned on in a cell, what their level of expression is, and at what times they are activated or shut off.

Polyadenylation (poly(A)) is a post-transcriptional modification of RNA found in all eukaryotic cells and in organelles, and is critical for nuclear export, stability, and translation control, but difficulties in globally measuring poly (A)-tail lengths have impeded greater understanding of poly(A)-tail function. Most eukaryotic mRNAs have poly (A) tails, which are added by a poly(A) polymerase following cleavage of the primary transcript during transcriptional termination. These tails are typically then truncated by deadenylases, and in some cases (e.g. animal oocytes, early embryos, or at neuronal synapses), the poly(A) tail can be re-extended by cytoplasmic poly(A) polymerases. Although poly(A) tails must exceed a minimal length to promote translation, the influence of tail length beyond this minimum is largely unknown. The prevailing view is that longer tails generally lead to increased translation, a theory derived from appending increasing lengths of synthetic poly(A) tails on *Xenopus* oocytes resulting in increased translation (see, for example, Barkoff et al EMBO J. 1998 Jun. 1; 17(11): 3168-3175). Additional supporting studies found this to be true in yeasts, however the general relationship between tail length and translational efficiency has not been reported outside of yeast, primarily because transcriptome-wide measurements have been unfeasible for longer-tailed mRNAs.

The length of the poly(A) tail is crucial for the transport of the mature mRNAs to the cytoplasm, their translation efficiency in certain developmental stages, and the quality control and degradation of mRNA. Recent studies suggest the average poly(A) tail length is approximately 30 nucleotides in yeast and approximately 50-100 nucleotides in mammalian and *Drosophila* cell lines (see, for example, Subtelny A O, Eichhorn S W, Chen G R, Sive H, Bartel D P. Poly(A)-tail profiling reveals an embryonic switch in translational control. Nature 2014; 508:66-71). The poly(A) tail is a dynamic region of the mRNA that is controlled differently depending on a specific developmental stage. It has been shown that an increase in poly(A) polymerase activity is associated with poor prognosis in certain cancers (see, for example, Scorilas A. Crit Rev Clin Lab Sci 2002; 39:193-224) and hematological diseases, and therefore, an understanding and control of the poly(A) tail length may be a determinant factor in the development of some diseases.

Methods described herein provide a new method for sequencing poly(A) RNA in its entirety, including the transcription start site, the splicing pattern, the 3' end and the poly(A) tail. This approach may be validated by northern blotting and high-resolution poly(A) tail assays (Hire-PAT).

For example, starting with an RNA transcript, adapters may be ligated onto the 5' and 3' ends and in the presence of a non-strand displacing reverse transcriptase, a complement of the RNA transcript is used as the input polynucleotide and subjected to the long read methods described herein. Briefly, an example interposing barcode is shown in FIG. 1A, and includes a loop region, a stem region, and two hybridization pads. The loop region includes about 10 to about 20 random nucleotides (e.g., CGCCAGCACT (SEQ ID NO:10)). In embodiments of the methods described herein, synthetic long reads are constructed by grouping together UMIs based on direct or indirect co-occurrence in the library, and then assembling the reads back into the original full-length molecule. In embodiments, the length of the UMI is optimized based on the total number of insertions sites (number of targeted molecules X number of insertion locations) to reduce the incorporation of two of the same UMIs in different molecules, while maximizing the amount of sequence in the read that is from the target molecule. Rare instances where the same UMI is observed in two different molecules can be addressed bioinformatically. Aside from forming the backbone for long read alignment, the introduction of UMIs into sequencing libraries prior to target amplification by PCR has been shown to dramatically increase the sensitivity for rare mutations and enable absolute read counting. The stem region includes two known sequences capable of hybridizing to each other, ranging from about 5 to about 10 nucleotides, and is stable (i.e., capable to remaining hybridized together) at approximately at a maximum temperature of 37° C., and unhybridizes (i.e., denatures) at temperatures greater than 50° C. Finally, the hybridization pads each includes about 9 to about 15 nucleotides (e.g., GTAAT for pad 1 and AGGCA for pad 2) and are capable of hybridizing to single stranded template nucleic acids (i.e., they are a complement to the original target). The sequences of the hybridization pad may be random or may include a targeted priming sequence to maximize placement of the IBC. FIG. 1B depicts the interposing barcode when the stem regions are denatured.

The nucleic acid sample used for this experiment contains total RNA or mRNA, preferably purified RNA or mRNA, from an organism (e.g., human). Total RNA includes, but is not limited to, protein coding RNA also called coding RNA such as messenger RNA (mRNA) and non-protein coding RNA (non-coding RNA or ncRNA), such as ribosomal RNA (rRNA), transfer RNA (tRNA), micro RNA (miRNA), small interfering RNA (siRNA), piwi-interacting RNA (piRNA), small nuclear RNA (snRNA) and small nucleolar RNA (snoRNA). Each one of these RNA types may be used as input. Optionally, and preferably, the RNA will include a poly(A) tail, however the RNA molecule may not have a poly(A) tail (e.g., non-protein coding RNAs (ncRNA) such as ribosomal RNA (rRNA), transfer RNA (tRNA), micro RNA (miRNA), small interfering RNA (siRNA), piwi-interacting RNA (piRNA) and small nuclear RNA (snRNA)). For example, prokaryotic mRNA does not have a poly(A) tail. In RNA molecules that do not have a poly A tail, a poly(A) tail may be added synthetically (e.g. enzymatically) to validate these studies. In embodiments, a poly(A) tail is enzymatically added to the RNA molecule using known techniques in the art.

An isolated RNA molecule (e.g., mRNA), may be further purified and selected for polyadenylation utilizing known techniques in the art (e.g., by mixing RNA with poly(T) oligomers covalently attached to a substrate, such as magnetic beads). The RNA may be reverse transcribed (e.g., reverse transcription with a non-strand displacing RT) to cDNA, followed by a DNA polymerase-mediated second strand synthesis to yield an input DNA molecule. It is known that RNA representation bias can be introduced with the generation of cDNA; therefore it may be preferable to use the RNA as the template directly. However it is known that the quantity of mRNA is orders of magnitude different than genomic DNA; therefore, either one may be used as input. To the input DNA or RNA molecule, interposing barcodes (as described herein) are added at an appropriate concentration such that there are approximately 50-100 bases between each IBC (e.g., see Example 8 for additional details). A non strand-displacing sequencing polymerase (e.g., Klentaq, T4, T7, Bst, Phusion, Tfl, Pfu, or Stoffel fragment) extends the complement strand to generate an extension segment, as shown in FIG. 2A, and a ligase ligates the ends of the extension segment together with the next interposing barcode to produce a single integrated strand, as depicted in FIG. 2B. The template DNA sample is washed away, and the resultant integrated strand may be subjected to reaction conditions (e.g., elevated temperature or denaturing additives) such that the stem regions of interposing barcodes and/or any secondary structures present denature to form a linear integrated strand, as schematically shown in FIG. 2C. The integrated strand may be amplified using known methods in the art (e.g., standard PCR amplification) and subjected to standard library preparation methods as known in the art and described herein. The integrated strand may serve as the input DNA with any commercially available library preparation kit. A variety of kits for making sequencing libraries from DNA are available commercially.

For example, the following protocol is then followed to prepare the integrated strand for sequencing on next generation sequencing devices.

The input DNA (i.e., the integrated strand) is fragmented to make small DNA molecules with a modal size of about 100 to about 400 base pairs with random ends. This is done by sonication, chemical fragmentation, or enzymatic fragmentation. The resulting DNA fragments generated by sonication will be end polished to produce a library of DNA fragments with blunt, 5'-phosphorylated ends that are ready for ligation. The end polishing is accomplished by using the T4 DNA polymerase, which can fill in 5' overhangs via its polymerase activity and recess 3' overhangs via its 3'-5' exonuclease activity. The phosphorylation of 5' ends is accomplished by T4 polynucleotide kinase.

Adapter ligation: Ligation of double-stranded DNA adapters is accomplished by use of T4 DNA ligase. Depending on the adapter, some double-stranded adapters may not have 5' phosphates and contain a 5' overhang on one end to prevent ligation in the incorrect orientation.

Now the adapter-ligated library may be size-selected (e.g., selecting for approximately 200-250 base pair size range). By doing this, unligated adapters and adapter dimers are removed, and the optimal size-range for subsequent PCR and sequencing is selected. Any suitable clean up method known to those skilled in the art may be used, such as magnetic bead-based clean up, or purification on agarose gels.

The resultant strand is then subjected to a nucleic acid sequencing reaction using any available sequencing technology. Once data is available from the sequencing reaction, initial processing (often termed "pre-processing") of the sequences is typically employed prior to annotation. Pre-processing includes filtering out low-quality sequences, sequence trimming to remove continuous low-quality nucleotides, merging paired-end sequences, or identifying and filtering out PCR repeats using known techniques in the art. The sequenced reads may then be assembled and aligned using bioinformatic algorithms known in the art (e.g., as depicted in FIG. 3).

Example 6: Metagenomics and Profiling of Bacteria

The study of bacterial phylogeny and taxonomy by analyzing the 16S rRNA gene has become popular among microbiologists due to the need to study the diversity and structure of microbiomes thriving in specific ecosystems. Due to its presence in almost all bacteria, the 16S rRNA gene is a core component of the 30S small subunit of prokaryotes. The 16S sequence contains ten conserved (C) regions that are separated by nine variable (V1-V9) regions, wherein the V regions are useful for taxonomic identification. Due to limitations in NGS platforms, the entirety of the 16S gene (approximately 1,500-1,800 bp) is difficult to accurately sequence.

Clever design of primers have been reported and used for amplifying specific V regions of 16S rRNA; for example, the third, fourth, and fifth variable regions (V3, V4 and V5 regions, respectively) have been used for studies where classification and understanding phylogenic relationships is important (see for example, Baker G. C., et al J. of Microbiological Methods, V55 (2003), 541-555; and Wang, Y., et al. (2014). PloS one, 9(3), e90053). While the information gained from sequencing the V3 or V4 region is valuable, no single variable region can differentiate among all bacteria. For example, the V1 region has been demonstrated to be particularly useful for differentiating among species in the genus *Staphylococcus*, whereas V2 distinguished among Mycobacterial species and V3 among *Haemophilus* species (Chakravorty, S., et al (2007). Journal of microbiological methods, 69(2), 330-339). It would therefore be very beneficial to be able to sequence the entirety of the 16S gene without having to a priori select appropriate primer sets. The methods described herein provide a new method for sequencing the 16S rRNA gene in its entirety, including the constant and nine variable regions. The methods allow for accurate species level determination by sequencing the entirety of the 16S gene, see FIGS. 10A-10H.

In this example, the interposing barcodes have targeted priming sequences in the hybridization pads, wherein the priming sequences target the constant regions that flank the variable regions.

Example 7: Sequencing of Cancer Samples

Genomic profiling of tumors plays a critical role in personalized therapy and has become the gold standard in diagnosis and treatment of multiple cancer types. The genetic diversity in cancer genomes is complex and dynamic throughout cancer progression. Genome-wide aberrations in cancer include gene amplifications and deletions, inversions, translocations and somatic mutations (Malkin, 2009, Gresham, 2019). Importantly, these changes are the basis for changes in expression levels of many oncogenes and tumor suppressors. While somatic mutations and small deletions and rearrangements are readily detected with short sequencing reads, long range rearrangements like copy number variations of genes (CNVs) pose a challenge owing to their repetitive nature.

Numerous DNA microarray and NGS assays exist that can measure genome-wide copy number changes. Generally, NGS provides better base resolution, improved dynamic range and does not have the limitation of requiring a priori knowledge of the aberrant loci. However, CNV determination by NGS is by no means trivial and is limited by coverage uniformity and poor mapping of repetitive regions (Okamoto, 2016, Kutalik, 2013, Eichler, 2011). CNV determination relies on applying a combination of paired-end and split read mapping, modeling read depth of healthy regions to identify insertions/deletions and de novo assembly (Kutalik, 2013). Aside from coverage issues introduced by the sequencing platform, many NGS library preparation protocols give rise to physical copy number changes. For instance, exome libraries utilize hybridization probes whose capture efficiencies depend on the GC content of targeted regions. More commonly, library protocols include a PCR amplification step, a method that may be prone to amplification bias, and can often overrepresent shorter amplicons with low sequence complexity (Li, 2016). Taipale and coworkers were among the first groups to demonstrate absolute molecule by tagging library fragments with UMIs (Taipale, 2011, van Haessler, 2018). Attaching a UMI to each DNA fragment prior to amplification makes each molecule unique. The central idea underlying read counting by UMIs is to count the number of distinct UMI sequences detected rather than attempting to count the number of reads. The identities of the UMIs are determined by sequencing. When enough sequences have been obtained, many UMI will have been observed multiple times and the number of original DNA molecules can be determined simply by counting the number of UMIs. Hereby care must be taken to sequence with appropriate coverage, however, it is not necessary to directly observe all UMIs since the number of unobserved UMIs can be estimated based on the distribution of the copy numbers of the observed UMIs.

Using the proposed UMI-containing barcodes for whole genome library preparation, such as the interposing barcodes as described herein, will benefit cancer genome analysis in multiple ways. First, the linked reads and resulting longer reads will improve the mapping quality and assembly of repetitive regions. This will allow for more accurate assembly of regions with extensive gene amplifications. Second, each read will be quantifiable via the UMI (e.g., the loop region), facilitating read depth modeling along the chromosomes. Third, the presence of the UMI will allow for distinguishing somatic mutations from mutations that are introduced during PCR (Li, 2016, Gresham, 2017, Weng, 2018). With these corrections, rare mutations with frequencies of 1-5% can be detected in heterogenous tissues. Error correction might be additionally aided by fragments (i.e., sequencing reads) that are linked to two interposed adapters because those help to identify point mutations in the UMI itself.

REFERENCES

1: Shlien A, Malkin D. Copy number variations and cancer. Genome Med. 2009 Jun. 16; 1(6):62. doi: 10.1186/gm62. PubMed PMID: 19566914; PubMed Central PMCID: PMC2703871.

2: Hieronymus H, Murali R, Tin A, Yadav K, Abida W, Moller H, Berney D, Scher H, Carver B, Scardino P, Schultz N, Taylor B, Vickers A, Cuzick J, Sawyers C L.

Tumor copy number alteration burden is a pan-cancer prognostic factor associated with recurrence and death. Elife. 2018 Sep. 4; 7. pii: e37294. doi: 10.7554/eLife.37294. PubMed PMID: 30178746; PubMed Central PMCID: PMC6145837.

3: Lauer S, Gresham D. An evolving view of copy number variants. Curr Genet. 2019 December; 65(6):1287-1295. doi: 10.1007/s00294-019-00980-0. Epub 2019 May 10. Review. PubMed PMID: 31076843.

4: Valsesia A, Mace A, Jacquemont S, Beckmann J S, Kutalik Z. The Growing Importance of CNVs: New Insights for Detection and Clinical Interpretation. Front Genet. 2013 May 30; 4:92. doi: 10.3389/fgene.2013.00092. eCollection 2013. PubMed PMID: 23750167; PubMed Central PMCID: PMC3667386.

5: Yamamoto T, Shimojima K, Ondo Y, Imai K, Chong P F, Kira R, Amemiya M, Saito A, Okamoto N. Challenges in detecting genomic copy number aberrations using next-generation sequencing data and the eXome Hidden Markov Model: a clinical exome-first diagnostic approach. Hum Genome Var. 2016 Aug. 18; 3:16025. doi: 10.1038/hgv.2016.25. eCollection 2016. PubMed PMID: 27579173; PubMed Central PMCID: PMC4989049.

6: Alkan C, Coe B P, Eichler E E. Genome structural variation discovery and genotyping. Nat Rev Genet. 2011 May; 12(5):363-76. doi: 10.1038/nrg2958. Epub 2011 Mar. 1. Review. PubMed PMID: 21358748; PubMed Central PMCID: PMC4108431.

7: Kou R, Lam H, Duan H, Ye L, Jongkam N, Chen W, Zhang S, Li S. Benefits and Challenges with Applying Unique Molecular Identifiers in Next Generation Sequencing to Detect Low Frequency Mutations. PLoS One. 2016 Jan. 11; 11(1):e0146638. doi: 10.1371/journal.pone.0146638. eCollection 2016. PubMed PMID: 26752634; PubMed Central PMCID: PMC4709065.

8: Kivioja T, Vaharautio A, Karlsson K, Bonke M, Enge M, Linnarsson S, Taipale J. Counting absolute numbers of molecules using unique molecular identifiers. Nat Methods. 2011 Nov. 20; 9(1):72-4. doi: 10.1038/nmeth. 1778. PubMed PMID: 22101854.

9: Pflug F G, von Haeseler A. TRUmiCount: correctly counting absolute numbers of molecules using unique molecular identifiers. Bioinformatics. 2018 Sep. 15; 34(18):3137-3144. doi: 10.1093/bioinformatics/bty283. PubMed PMID: 29672674; PubMed Central PMCID: PMC6157883.

10: Fu Y, Wu P H, Beane T, Zamore P D, Weng Z. Elimination of PCR duplicates in RNA-seq and small RNA-seq using unique molecular identifiers. BMC Genomics. 2018 Jul. 13; 19(1):531. doi: 10.1186/s12864-018-4933-1. PubMed PMID: 30001700; PubMed Central PMCID: PMC6044086.

11: Hong J, Gresham D. Incorporation of unique molecular identifiers in TruSeq adapters improves the accuracy of quantitative sequencing. Biotechniques. 2017 Nov. 1; 63(5):221-226. doi: 10.2144/000114608. PubMed PMID: 29185922.

12: Smith T, Heger A, Sudbery I. UMI-tools: modeling sequencing errors in Unique Molecular Identifiers to improve quantification accuracy. Genome Res. 2017 March; 27(3):491-499. doi: 10.1101/gr.209601.116. Epub 2017 Jan. 18. PubMed PMID: 28100584; PubMed Central PMCID: PMC5340976.

Example 8: Library Preparation and Nucleic Acid Workflow

Figure 5A:
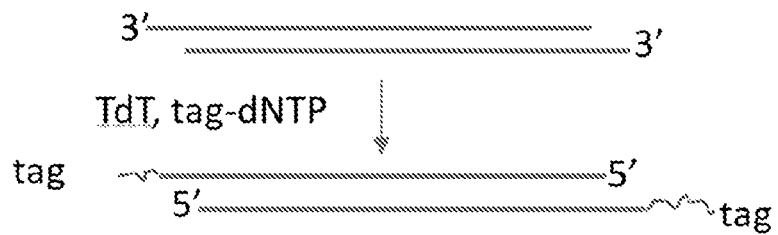
FIGS. 5A-5C demonstrate potential DNA workflow options as further described in Example 8.
Figure 5A:
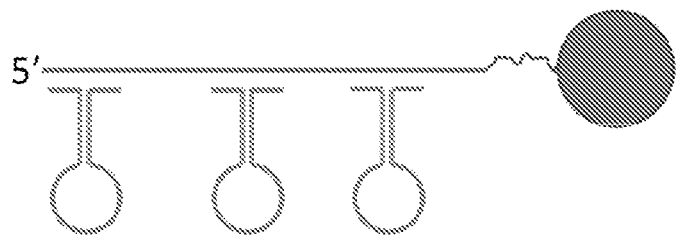
Figure 5A:
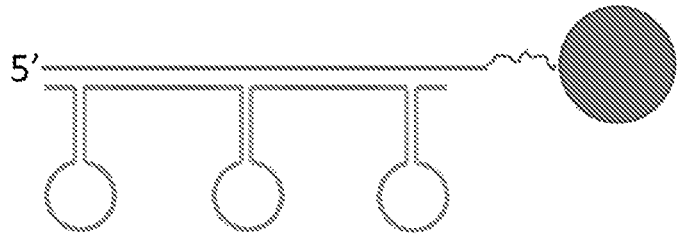

DNA Library Preparation is performed according to known methods in the art, e.g., described elsewhere and briefly below. For whole genome workflows, one option as depicted in FIG. 5A, genomic DNA is tethered to an affinity tag (e.g., biotinylated) using known techniques in the art. For example, biotin-containing dideoxynucleotide triphosphates (biotin-ddNTP) are added in the presence of a non strand-displacing DNA polymerase (e.g., Klentaq, T4, T7, Bst, Phusion, Tfl, Pfu, or Stoffel fragment) or terminal transferase (TdT) such that the input genomic DNA is biotinylated on the 3' ends. Next, the double stranded biotinylated DNA is subjected to denaturing conditions (e.g., elevated temperature or NaOH, followed by neutralization) and attached to a complementary affinity (e.g., streptavidin) decorated bead. The biotin reacts to covalently attach the 3' end of the single strand DNA.

Sample interposing barcodes (as described herein) are added at an appropriate concentration such that there are approximately 50-100 bases between each hybridized IBC. A non strand-displacing polymerase (e.g., Klentaq, T4, T7, Bst, Phusion, Tfl, Pfu, or Stoffel fragment) extends the complement strand to generate an extension segment, as shown in FIG. 2A, and a ligase (e.g., T4 DNA ligase, Ampligase, Tth ligase, T7 ligase, E. coli DNA ligase, 9° N™ DNA Ligase (NEB), or Taq Ligase) ligates the ends of the extension segment together with the next interposing barcode to produce a single integrated strand, as depicted in FIG. 2B. As non strand-displacing DNA polymerases have a slight ability to displace a DNA oligonucleotide from a template strand, the hybridization of the oligonucleotide can be enhanced in order to stop strand displacement by the polymerase.

Figure 5B:
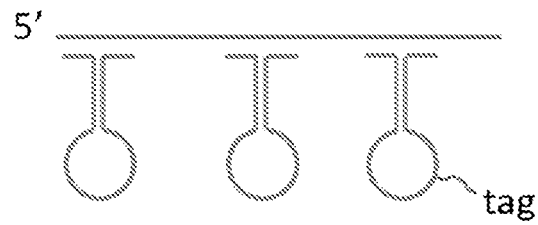
Figure 5B:
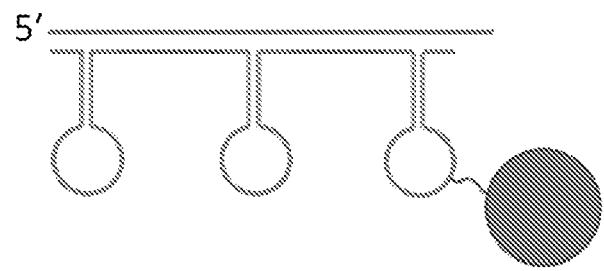
Figure 5B:

Alternatively, as illustrated in FIG. 5B, the loop region of an IBC includes a modified nucleotide that contains an affinity tag (e.g., a biotin containing nucleotide). A mixture of modified IBCs and non-modified IBCs are added are added at an appropriate concentration such that there are approximately 50-100 bases between each hybridized IBC. A non strand-displacing polymerase (e.g., Klentaq, T4, T7, Bst, Phusion, Tfl, Pfu, or Stoffel fragment) extends the complement strand to generate an extension segment, as shown in FIG. 2A, and a ligase (e.g., T4 DNA ligase, Ampligase, Tth ligase, T7 ligase, E. coli DNA ligase, 9° N™ DNA Ligase (NEB), or Taq Ligase) ligates the ends of the extension segment together with the next interposing barcode to produce a single integrated strand, as depicted in FIG. 2B. As non strand-displacing DNA polymerases have a slight ability to displace a DNA oligonucleotide from a template strand, the hybridization of the oligonucleotide can be enhanced in order to stop strand displacement by the polymerase. The modified IBC reacts with a complementary affinity tag (e.g., streptavidin) decorated bead to immobilize the nucleic acid sequence.

The template DNA sample may be washed away (e.g., step 4 of FIG. 5A or step 3 of FIG. 5B, and the resultant integrated strand (i.e., the complementary strand containing a plurality of adapters) may be subjected to reaction conditions (e.g., elevated temperature or denaturing additives) such that the stem regions of interposing barcodes and/or any secondary structures present denature to form a linear integrated strand, as schematically shown in FIG. 2C. The integrated strand is then converted to double stranded DNA (e.g., Single Strand Adapter Library Prep (SALP) or by ss-DNA ligation using CircLigaser™) and amplified using known techniques in the art.

Figure 5C:
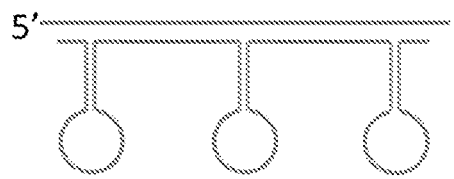
Figure 5C:
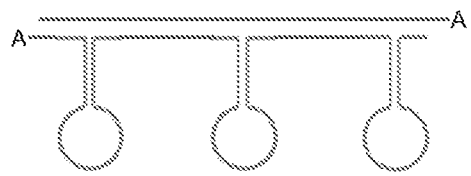
Figure 5C:
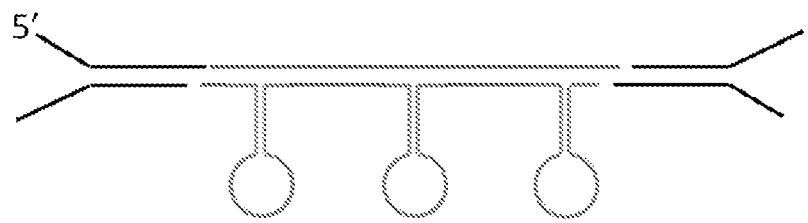
Figure 5C:
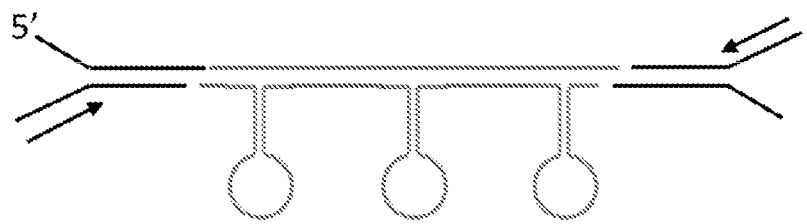

An alternative workflow is presented in FIG. 5C, wherein the original template is not washed away. In this workflow, genomic DNA is denatured and IBCs are added at an appropriate concentration such that there are approximately 50-100 bases between each hybridized IBC. A non strand-displacing polymerase (e.g., Klentaq, T4, T7, Bst, Phusion, Tfl, Pfu, or Stoffel fragment) extends the complement strand to generate an extension segment, as shown in FIG. 2A, and a ligase (e.g., T4 DNA ligase, Ampligase, Tth ligase, T7 ligase, E. coli DNA ligase, 9° N™ DNA Ligase (NEB), or Taq Ligase) ligates the ends of the extension segment together with the next interposing barcode to produce a single integrated strand, as depicted in FIG. 2B. As non strand-displacing DNA polymerases have a slight ability to displace a DNA oligonucleotide from a template strand, the hybridization of the oligonucleotide can be enhanced in order to stop strand displacement by the polymerase. The DNA fragments are end repaired or end polished. Generally, a single adenine base is added to form an overhang via an A-tailing reaction. This "A" overhang allows adapters containing a single thymine overhanging base to base pair with the DNA fragments. Additional sequences such as universal adapters or primers may then be added using conventional means to permit platform specific sequences or to provide a binding site for sequencing primers (e.g., see FIG. 5C), followed by fragmentation and additional library preparation steps according to commercial library prep kits.

Figure 6A:
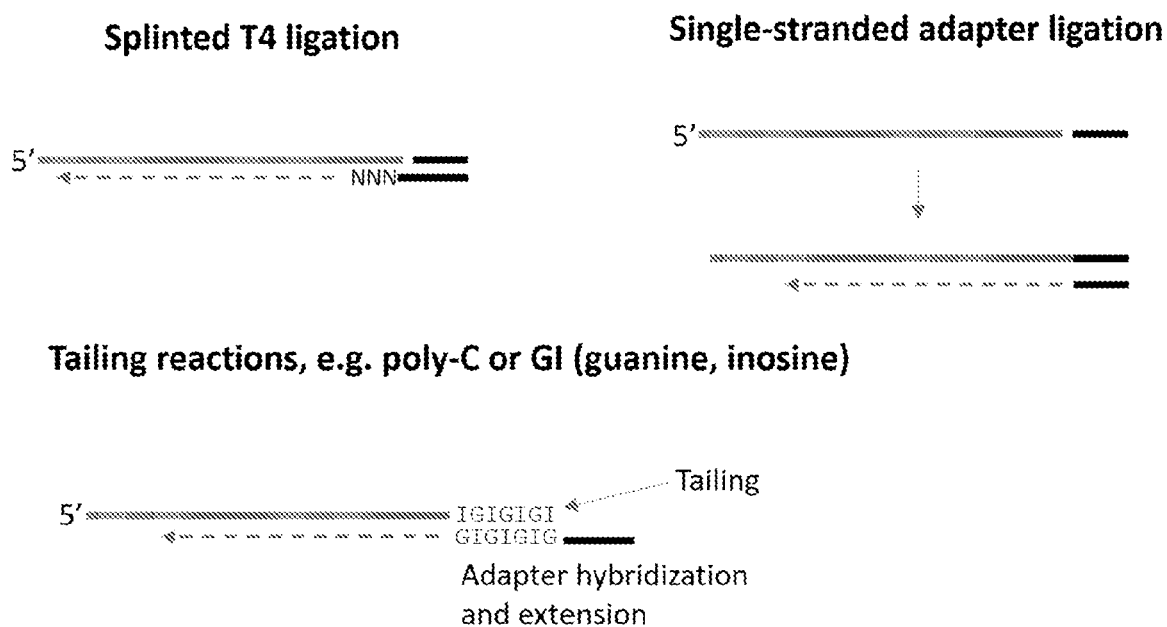
FIGS. 6A-6D provides illustrative embodiments of amplification options.
Figure 6B:
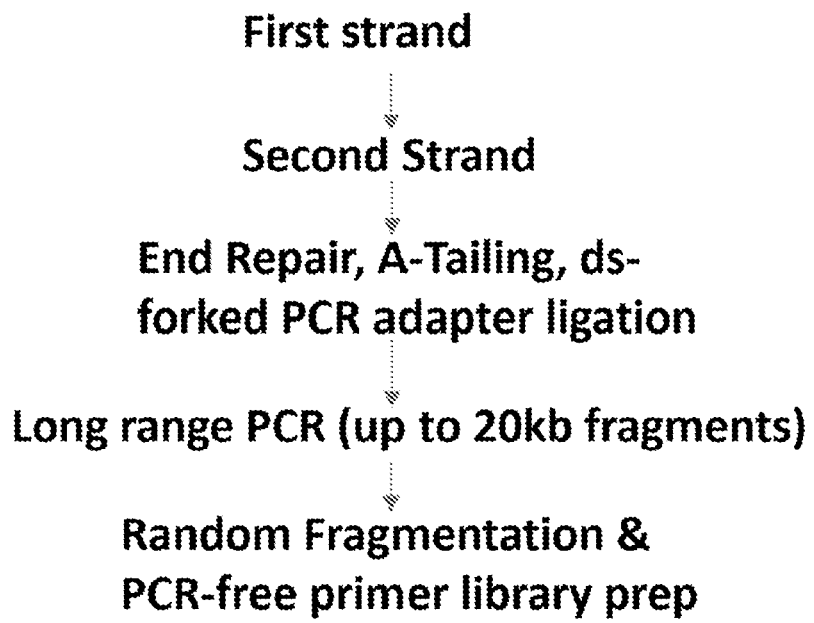
Figure 6C:
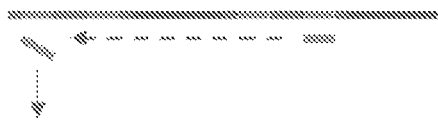
Figure 6C:
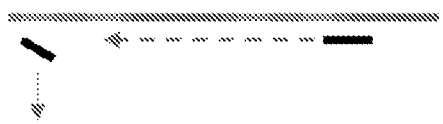
Figure 6D:

The workflows described in FIGS. 5A-5C conclude with an amplification process. Depicted in FIG. 6A-6D are potential amplification options for the integrated strand (i.e., the nucleic acid sequence containing interposing barcodes, as described herein). FIG. 6A illustrates splinted T4 ligation of a suitable primer with a random 5' overhang to initiate amplification. FIG. 6A also illustrates single-stranded adapter ligation, wherein the primer serves as the complement to an amplification primer. FIG. 6A further illustrates potential tailing reactions (e.g., GI tailing) followed by hybridization of an appropriate complementary amplification primer. FIG. 6B provides a schematic overview for the methods depicted in FIG. 6A. An additional amplification workflow is shown in FIG. 6C, which requires strand displacing amplification. FIG. 6D provides a schematic overview for the methods depicted in FIG. 6C.

Figure 7A:
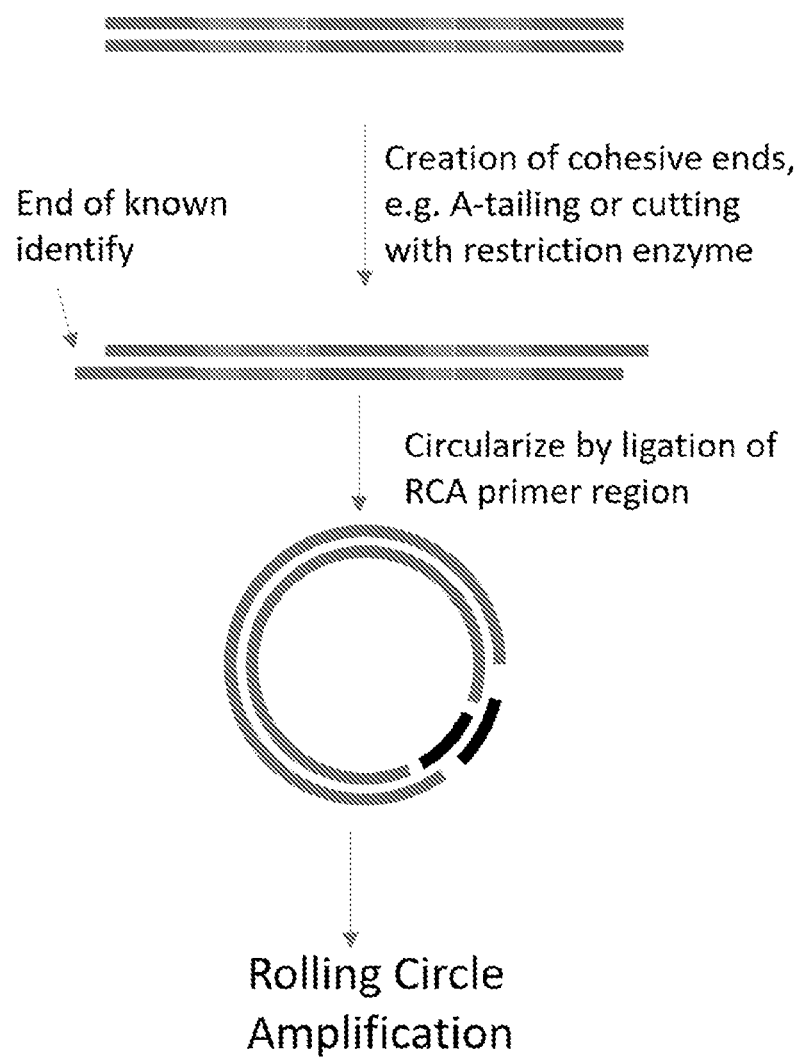
FIGS. 7A-7B provides workflow examples for rolling circle amplification with different starting materials: unfragmented double stranded DNA (FIG. 7A) and unfragmented single stranded DNA (FIG. 7B).
Figure 7B:
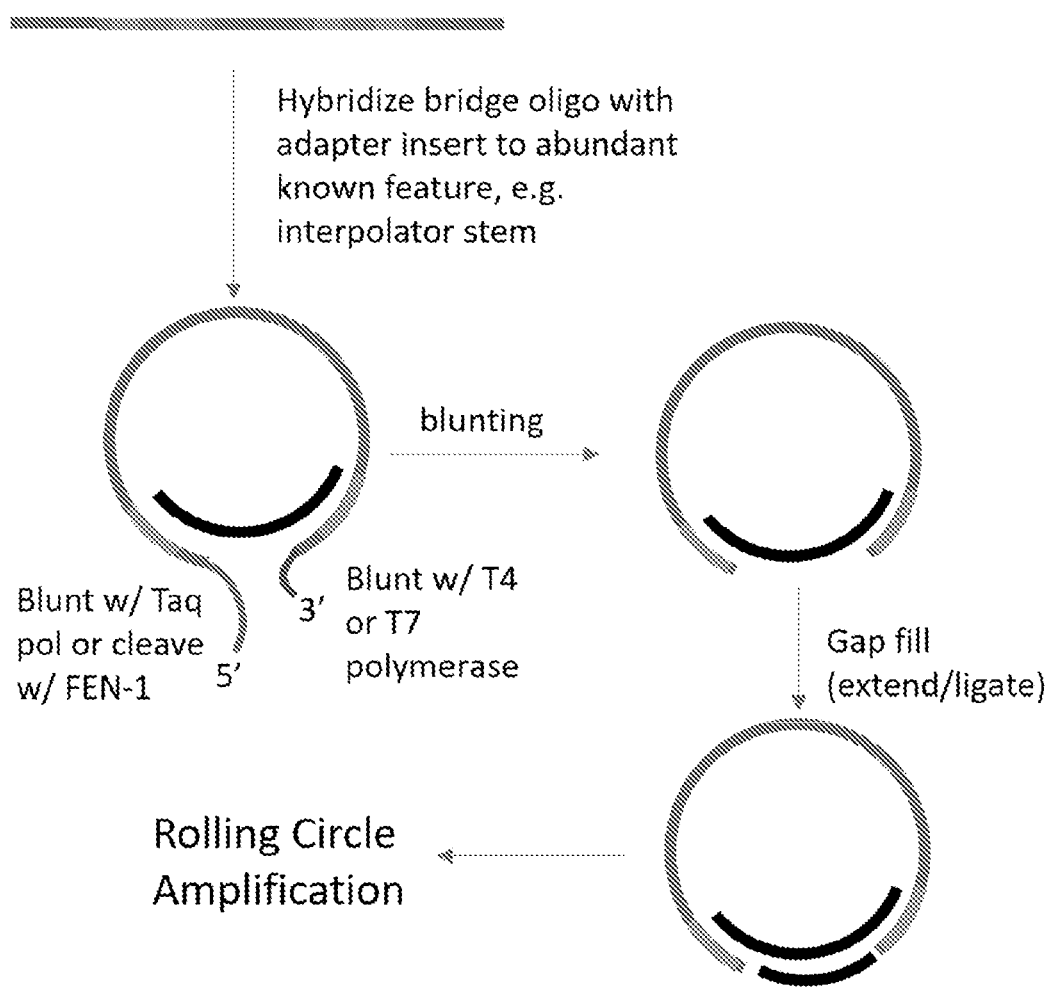

Amplification may be performed using circularization amplification according to known methods in the art (e.g., S. Myllykangas et al. BMC Biotechnology 2011, 11:122 (2011)). As shown in FIG. 7A and FIG. 7B, unfragmented double stranded DNA containing IBCs (FIG. 7A) or unfragmented single stranded DNA containing IBCs (FIG. 7B) may be used as starting material. Both of the methods depicted in the FIGS. 7A-7B outline the initial steps for amplifying the integrated strand (i.e., the nucleic acid sequence containing IBCs generated according to the methods provided herein) via rolling circle amplification (RCA).

Figure 8A:
FIGS. 8A-8B demonstrate potential RNA workflow options as further described in Example 8.
Figure 8A:
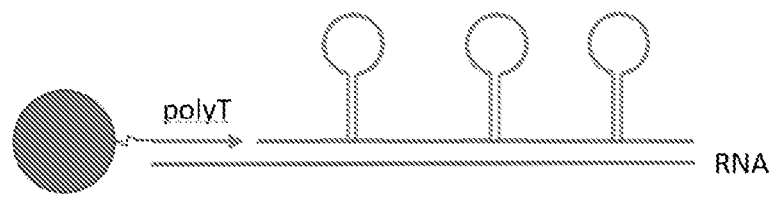
Figure 8B:
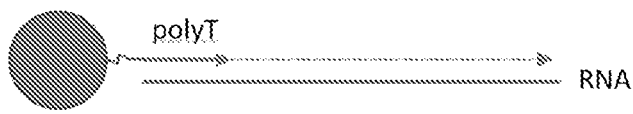
Figure 8B:
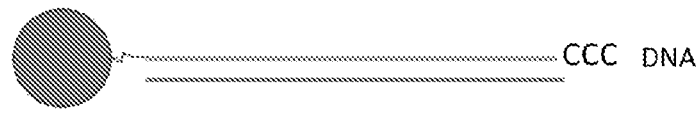
Figure 8B:
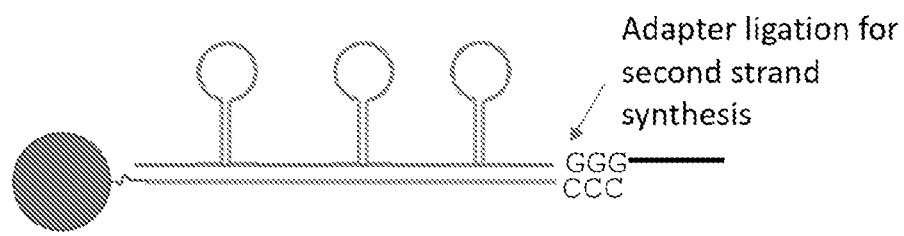
Figure 9:
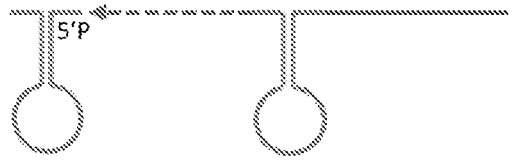
FIG. 9 illustrates a method for improved ligation by taking advantage of a 5' flap overhang, which is common for non-strand displacing polymerases.
Figure 9:
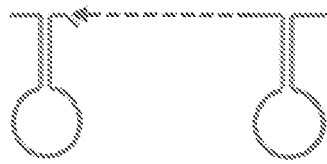
Figure 9:
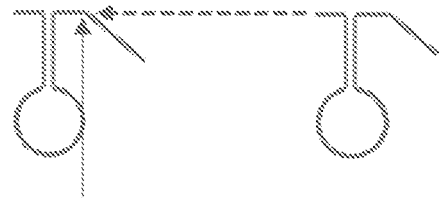
Figure 10A:
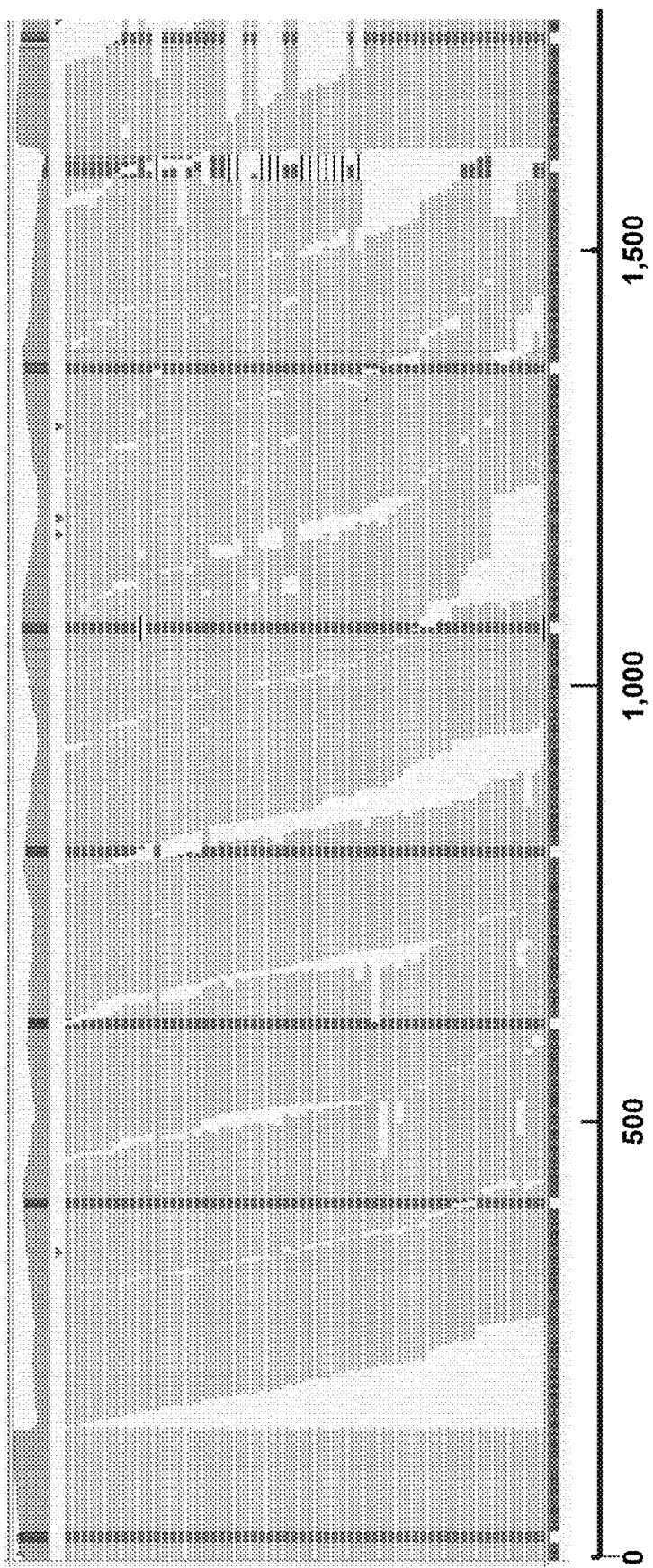
FIGS. 10A-10H shows the results of an IBC-based bioinformatic reconstruction of a *Enterococcus faecalis* 16S gene (FIG. 10A); *Escherichia coli* 16S gene (FIG. 10B); *Listeria monocytogenes* 16S gene (FIG. 10C); *Meiothermus ruber* 16S gene (FIG. 10D); *Pedobacter heparinus* 16S gene (FIG. 10E); *Pseudomonas aeruginosa* 16S gene (FIG. 10F); *Salmonella enterica* 16S gene (FIG. 10G); and *Staphylococcus aureus* 16S gene (FIG. 10H). The groups of vertical lines in the contig sequence represent unique molecular identifiers (UMIs) that were used for aligning the reads. Each grey horizontal line represents a sequenced fragment, and a visual representation of the coverage is represented on the top. The arrows are indicative of at least one insertion event. The axis indicates nucleotide length.
Figure 10B:
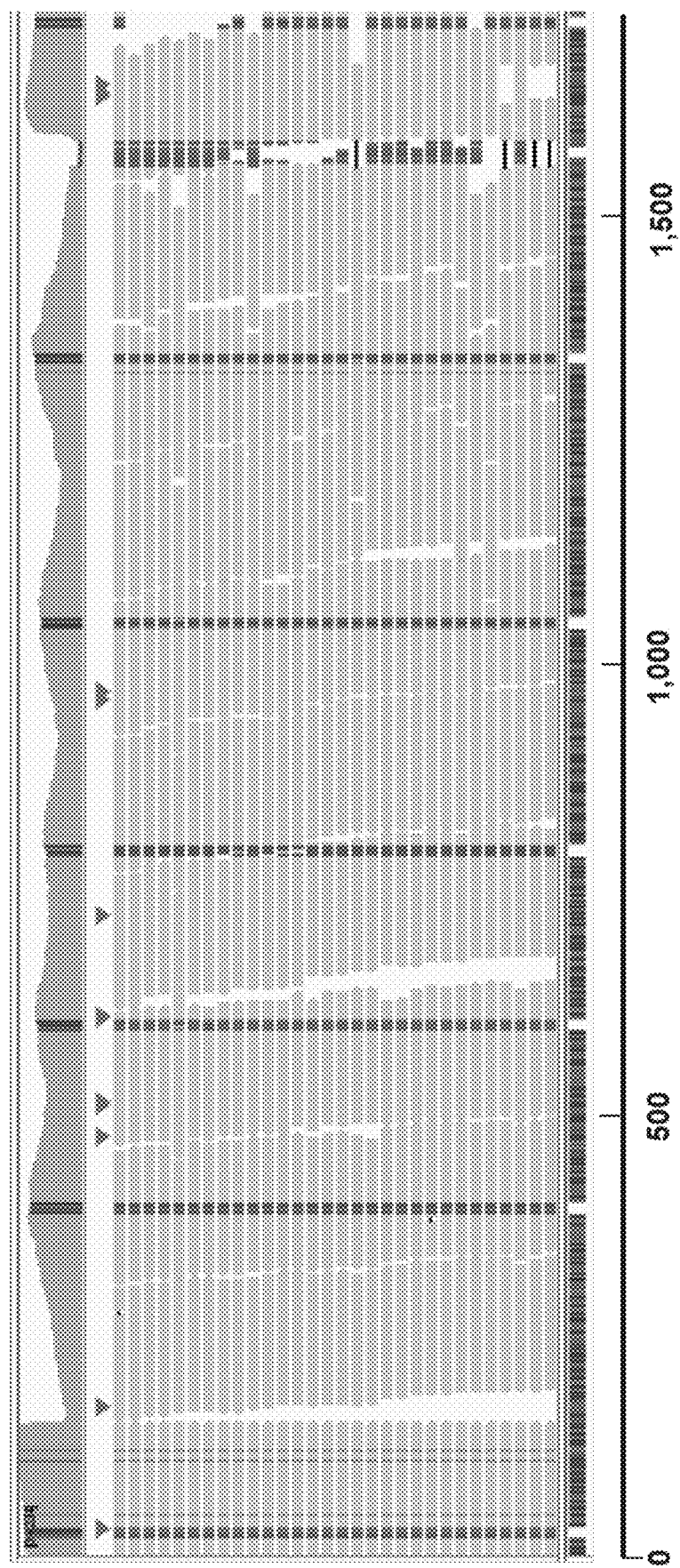
Figure 10C:
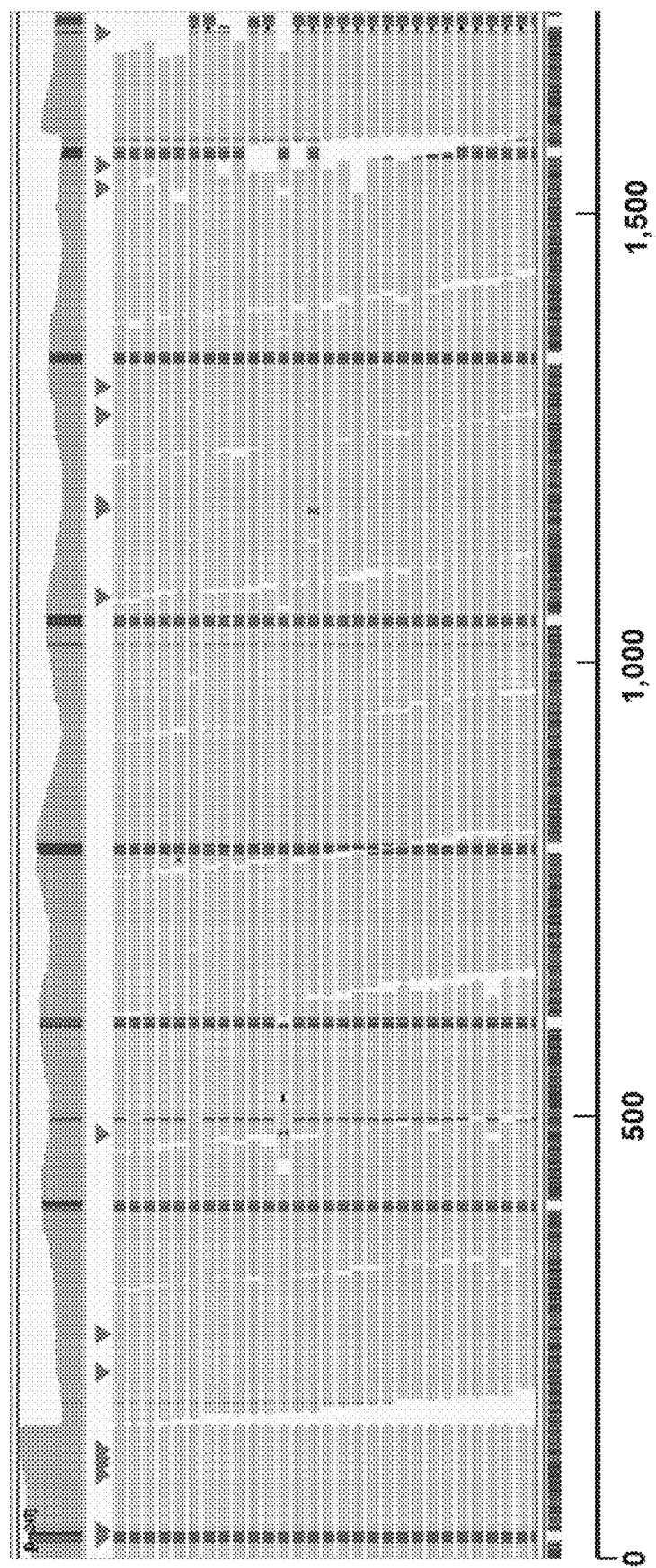
Figure 10D:
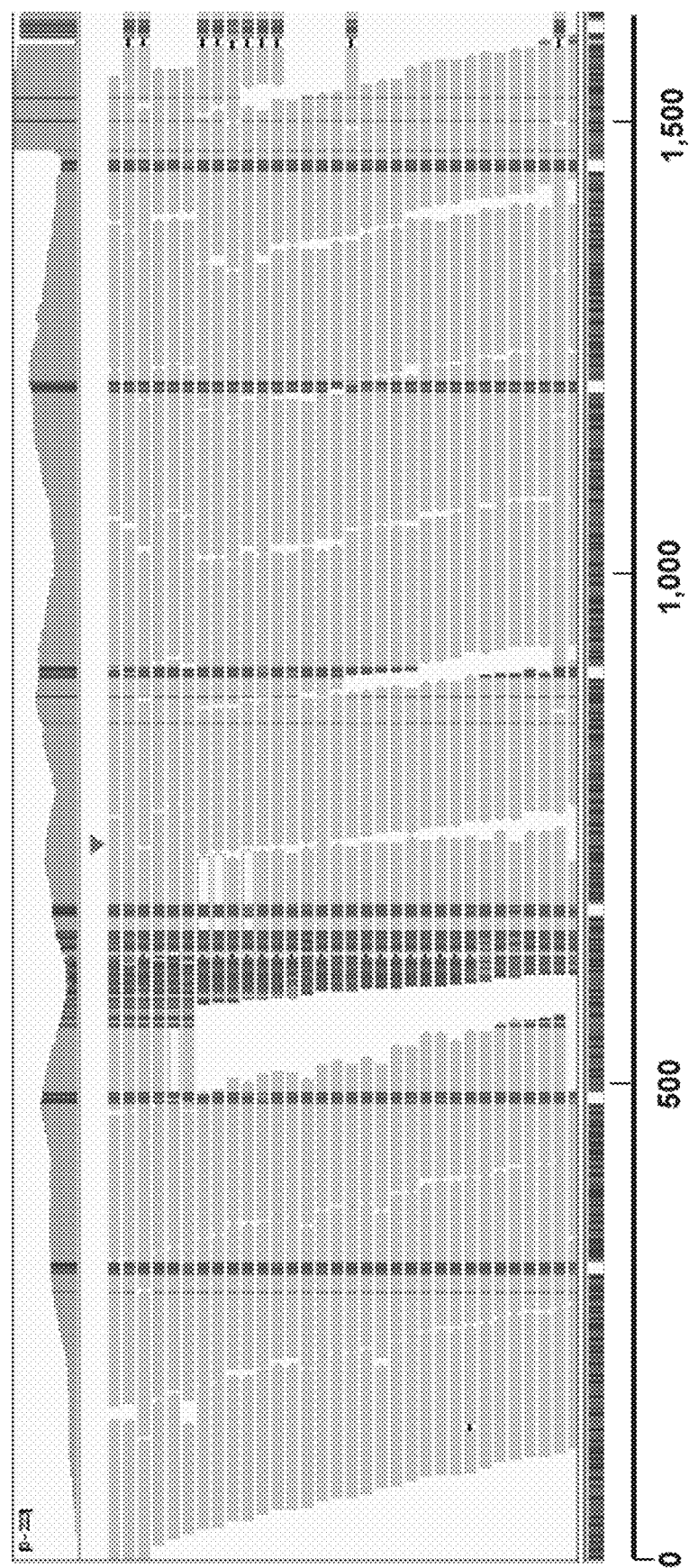
Figure 10E:
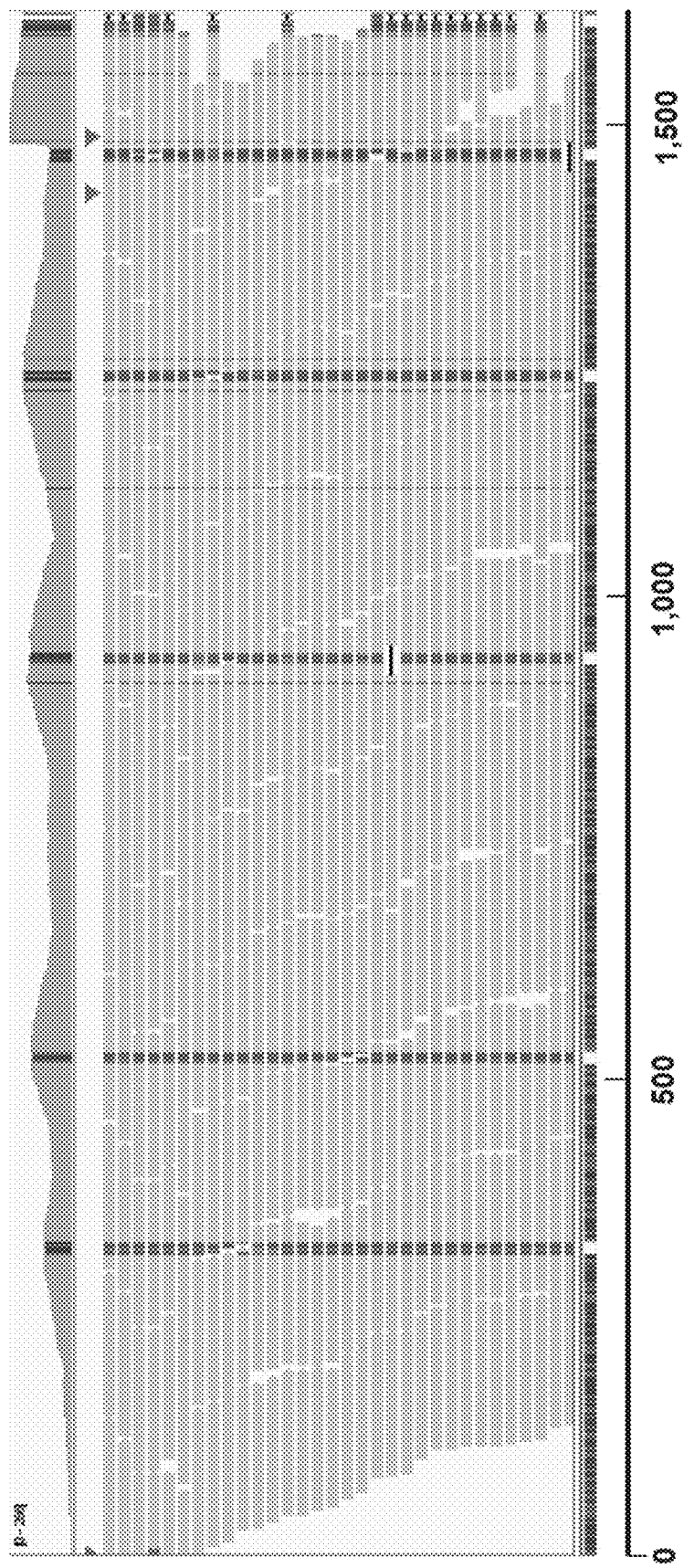
Figure 10F:
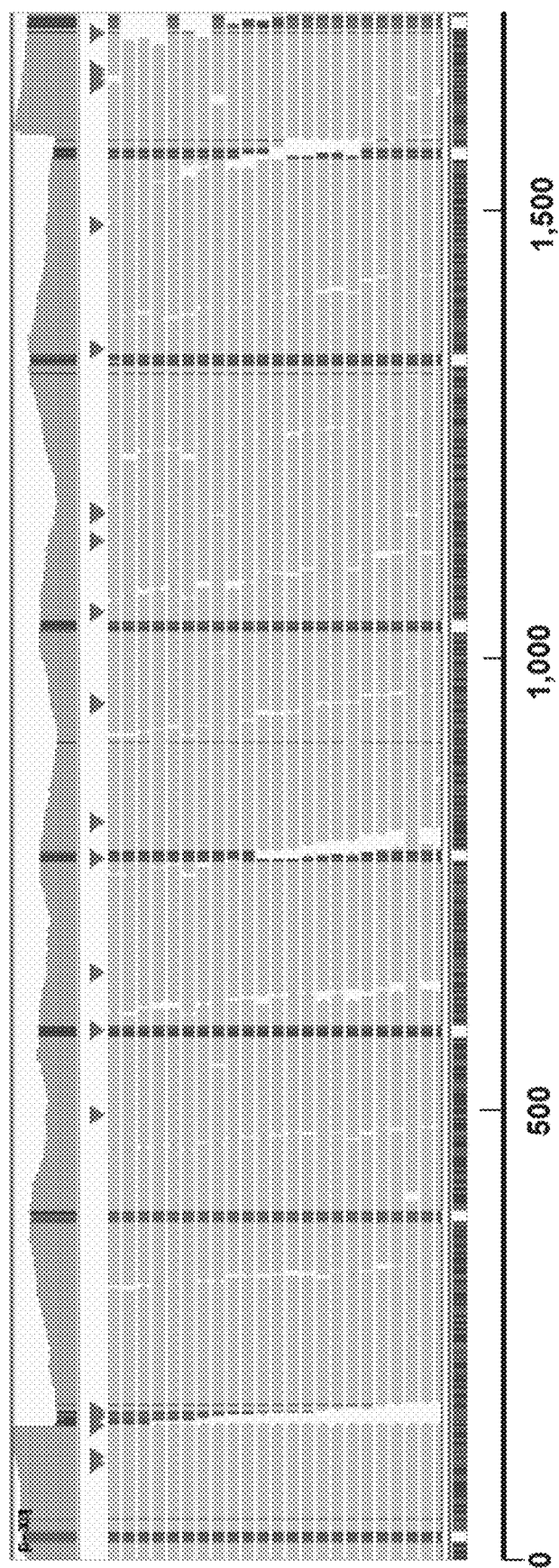
Figure 10G:
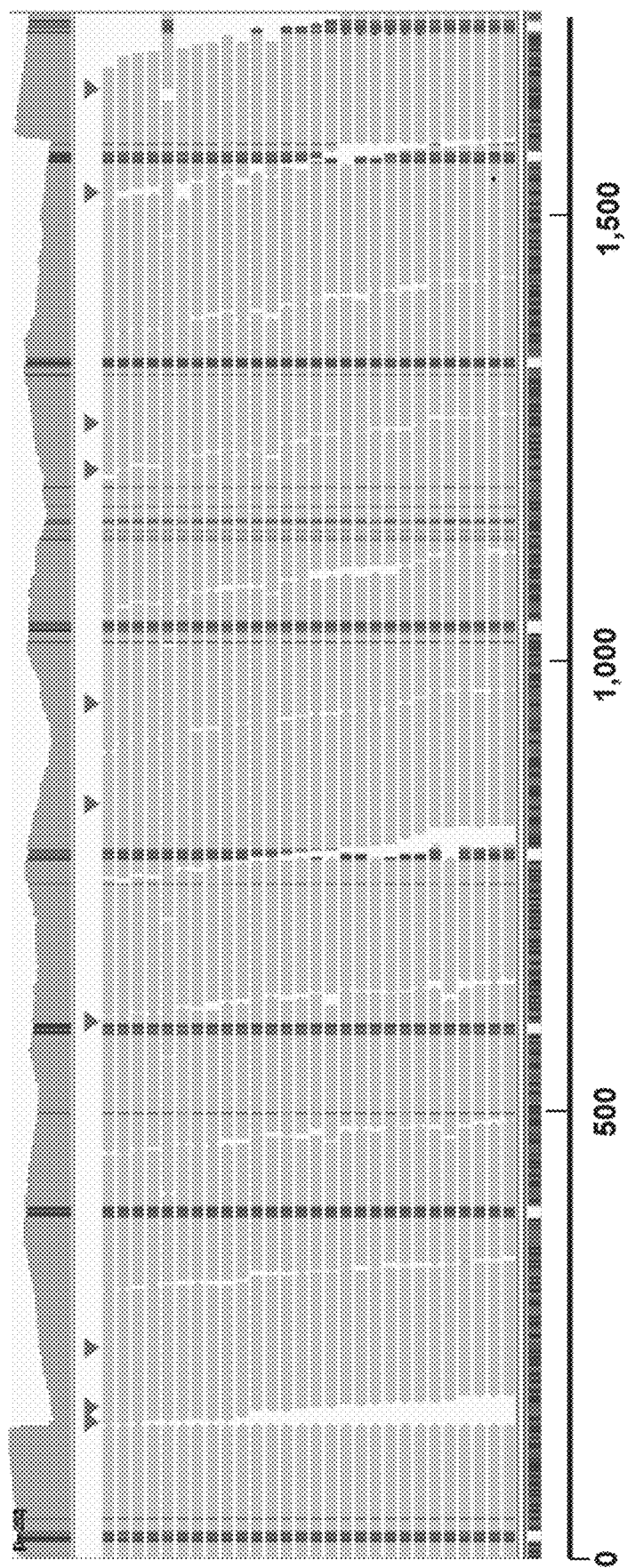
Figure 10H:
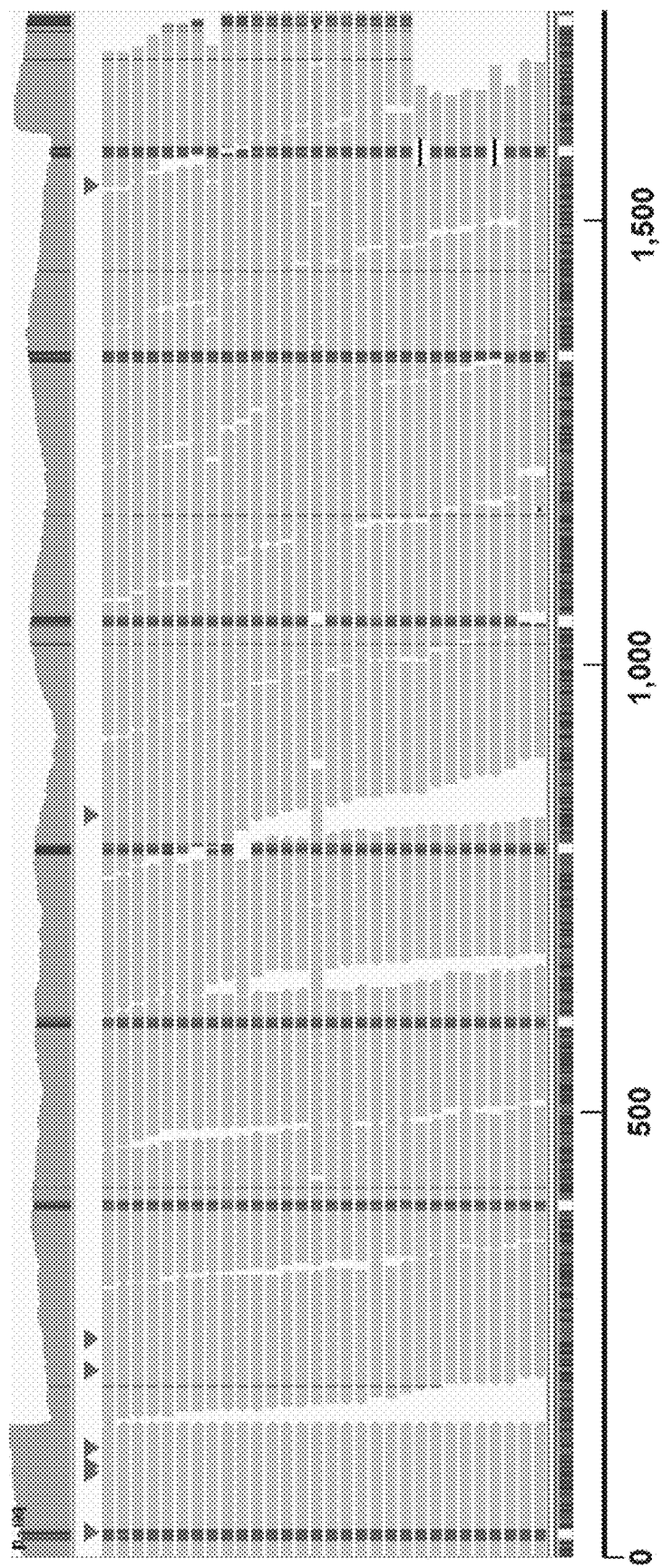

RNA Library Preparation is performed according to known methods in the art, e.g., described elsewhere and briefly below. One option, as depicted in FIG. 8A, RNA (e.g., mRNA) is captured by taking advantage of the polyadenylated (poly(A)) tail. Briefly, a surface immobilized poly(T) (e.g., a bead containing a poly(T) sequence) hybridizes with the poly(A) portion of the input RNA. Sample interposing barcodes (as described herein) are added at an appropriate concentration such that there are approximately 50-100 bases between each hybridized adapter. A non strand-displacing polymerase extends the complementary strand to generate an extension segment, as shown in FIG. 2A, and a ligase (e.g., T4 RNA ligase, T4 RNA Ligase 2, or PBCV-1 DNA Ligase) ligates the ends of the extension segment together with the next interposing barcode to produce a single integrated strand, as depicted in FIG. 2B. An alternative option, illustrated in FIG. 8B, a surface immobilized poly(T) (e.g., a bead containing a poly(T) sequence) hybridizes with the poly(A) portion of the input RNA. Also present, either before or after the poly(T) sequence, is a priming region for a reverse transcriptase. In the presence of a reverse transcriptase, complementary DNA (cDNA) is generated. The cDNA may be optionally terminated with a plurality of cytosines, referred to as C-tailing in FIG. 8B. The RNA is then removed and sample interposing barcodes (as described herein) are added at an appropriate concentration such that there are approximately 50-100 bases between each hybridized adapter. A non strand-displacing polymerase extends the complement strand to generate an extension segment, as shown in FIG. 2A, and a ligase (e.g., T4 RNA ligase, T4 RNA Ligase 2, or PBCV-1 DNA Ligase) ligates the ends of the extension segment together with the next interposing barcode to produce a single integrated strand, as depicted in FIG. 2B.

The resultant integrated strand (i.e., the complementary strand containing a plurality of adapters) may be subjected to reaction conditions (e.g., elevated temperature or denaturing additives) such that the stem regions of interposing barcodes and/or any secondary structures present denature to form a linear integrated strand, as schematically shown in FIG. 2C. The integrated strand is then converted to double stranded DNA (dsDNA) using known techniques in the art (e.g., Single Strand Adapter Library Prep (SALP) or by ss-DNA ligation using a CircLigase™) and amplified according to the methods known in the art or described herein.

Example 9: IBC-LED Reconstruction of Synthetic Long Reads

Using the methods described supra and herein, we performed a proof-of-concept experiment sequencing synthetic templates comprising either a 16S bacterial gene or an antibody VDJ region. UMI-containing IBCs were implemented to generate an integrated strand that was then amplified and sequenced. Following the sequencing, the synthetic long reads were constructed by aligning all sequencing reads that contained the same UMI.

Nucleic acid preparation: Template regions to be sequenced (e.g. synthetic 16S bacterial region or VDJ region of antibody) were amplified by PCR with a biotinylated primer and a non-biotinylated primer and a dNTP mix containing dUTP, dTTP, dATP, dGTP and dCTP. 0.25 pmols of template was pulled down using 100 ug of MyOne Streptavidin C1 (Invitrogen) beads in binding and wash buffer. The non-biotinylated strand of the template was then separated by denaturing with 0.1M NaOH.

Adapter annealing: Following template denaturation, the biotinylated strand-bound beads were then washed twice with binding and wash buffer and resuspended in 1×T4 DNA ligase buffer in the presence of 0.5 mM total dNTPs and synthetic long read adapters at a final concentration of 150 nM each. The adapters were annealed onto the template by heating to 95° C. for three minutes and then cooling to 37° C. at 0.1° C./min and incubating at 37° C. for an additional 30 minutes. The slow rate of cooling ensures proper hybridization of the IBC to the target sequence.

Concatenation of adapters and synthetic strand isolation: Following adapter annealing, 1200 units of T4 DNA ligase (NEB) and 3 units of T4 DNA polymerase (NEB) were then added to the samples and samples incubated for a further 1 hour at 37° C. in order to produce the synthetic construct containing multiple IBCs. Beads were then pelleted, and the supernatant discarded. Beads were washed twice with 1× binding and wash buffer. The synthetic strand was then eluted by combining the beads with 20 uL of 0.1 M NaOH and incubating for 3 minutes and transferring 18 uL of the supernatant to a fresh tube containing 9 uL of 200 mM Tris, pH 8. The samples were treated with 1U of Thermolabile User II enzyme (NEB) in the presence of 1× Cutsmart buffer (NEB) for 15 minutes and then purified with 1× volume sparQ beads (Quantabio).

Amplification and purification: 1 uL of the synthetic strand product was then amplified by PCR using primers that bind to the terminal adapters using Q5 or Phusion enzymes (NEB). PCR amplification was followed in real-time and stopped once the PCR reached the exponential phase. Samples were purified using sparQ beads and run on a 2% agarose gel. Products of appropriate size was then cut out and purified using the DNA agarose gel extraction kit (Zymo). 10,000 gel extracted molecules were then used as template for a second round of PCR using the Q5 enzyme, with this PCR reaction also followed in real-time and stopped as soon as the reaction hit the exponential phase.

Library prep and sequencing: The $2^{nd}$ PCR reaction was then used as input to prepare sequencing library using the Quantabio DNA fragmentation and Library prep kit. Sequencing libraries were sequenced as 2×150 bp paired-end runs on a HiSeq X-10 sequencer (Illumina) to obtain 20 million reads (10 million clusters) per sample.

Figure 14:
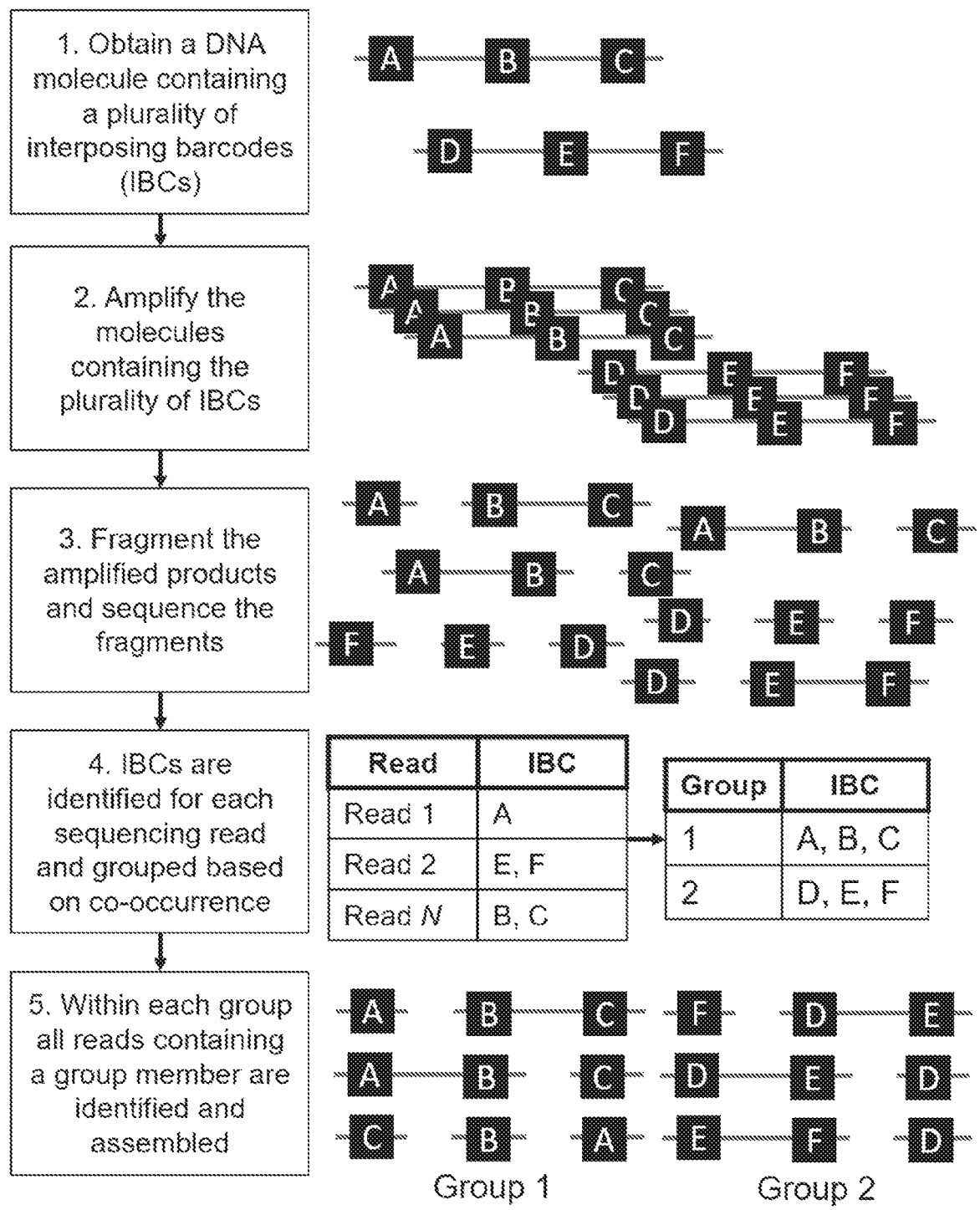
FIG. 14 describes a non-limiting example of the methods described herein. As described herein, a plurality of interposing barcodes (IBCs), are hybridized to a sample polynucleotide, extended, and ligated together to form a tagged complement of the sample polynucleotide. The IBCs are represented as A, B, C, D, E, and F in FIG. 14. The tagged complement is then amplified (step 2 of FIG. 14) and fragmented. The fragments may be prepared according to standard library prep methods (e.g., polishing, A-tailing, etc.) and have platform specific primers/adapters ligated to the ends to make them compatible with particular sequencing modalities. The fragments are then sequenced and the barcodes are identified for each sequencing read. The sequencing reads are grouped according the co-occurrence of IBCs, and within each group all the sequencing reads containing a group member are identified and assembled.

As depicted in FIG. 14, a non-limiting example of the assembly process is described. As described herein, a plurality of interposing barcodes (IBCs), are hybridized to a sample polynucleotide, extended, and ligated together to form a tagged complement of the sample polynucleotide. The IBCs are represented as single letters: A, B, C, D, E, and F in FIG. 14. The tagged complement was then amplified (step 2 of FIG. 14) and fragmented. The fragments are then sequenced, and the IBCs are identified for each sequencing read. The sequencing reads are grouped according the co-occurrence of IBCs, (i.e., if UMI A is observed with B, and B is observed with C, A B and C must have all come from the same molecule). Inter-molecular chimeras can form during library prep, leading to UMIs from two distinct molecules being incorrectly associated. To resolve these errors, spurious UMI associations can be identified and filtered out based on their absolute frequency within the library (e.g., employing a filter that does not associate UMIs that are only observed together in a single read), or their relative frequency to other associations within the group (e.g., filter out UMI associations that are observed at <10 times the frequency of other neighboring UMI associations within a group). Given each processed UMI grouping, all the sequencing reads containing a group member are identified and assembled reconstruct the full-length target molecule. For illustrative purposes, the reads contained within a single group are aligned against the target molecule to produce the Integrated Genomics Viewer plots depicted in FIGS. 10A-10H and FIGS. 12A-12J.

Results: Bacterial 16S genes from *Enterococcus faecalis* 16S gene, 1754 bp, (FIG. 10A); *Escherichia coli* 16S gene, 1729 bp, (FIG. 10B); *Listeria monocytogenes* 16S gene, 1737 bp, (FIG. 10C); *Meiothermus ruber* 16S gene, 1614 bp, (FIG. 10D); *Pedobacter heparinus* 16S gene, 1622 bp, (FIG. 10E); *Pseudomonas aeruginosa* 16S gene, 1723 bp, (FIG. 10F); *Salmonella enterica* 16S gene, 1729 bp, (FIG. 10G); and *Staphylococcus aureus* 16S gene, 1739 bp, (FIG. 10H) were successfully reconstructed. The results depicted in FIGS. 10A-10H show the methods and compositions described herein are capable of sequencing 1.5 kb-1.8 kb genes.

Figure 11:
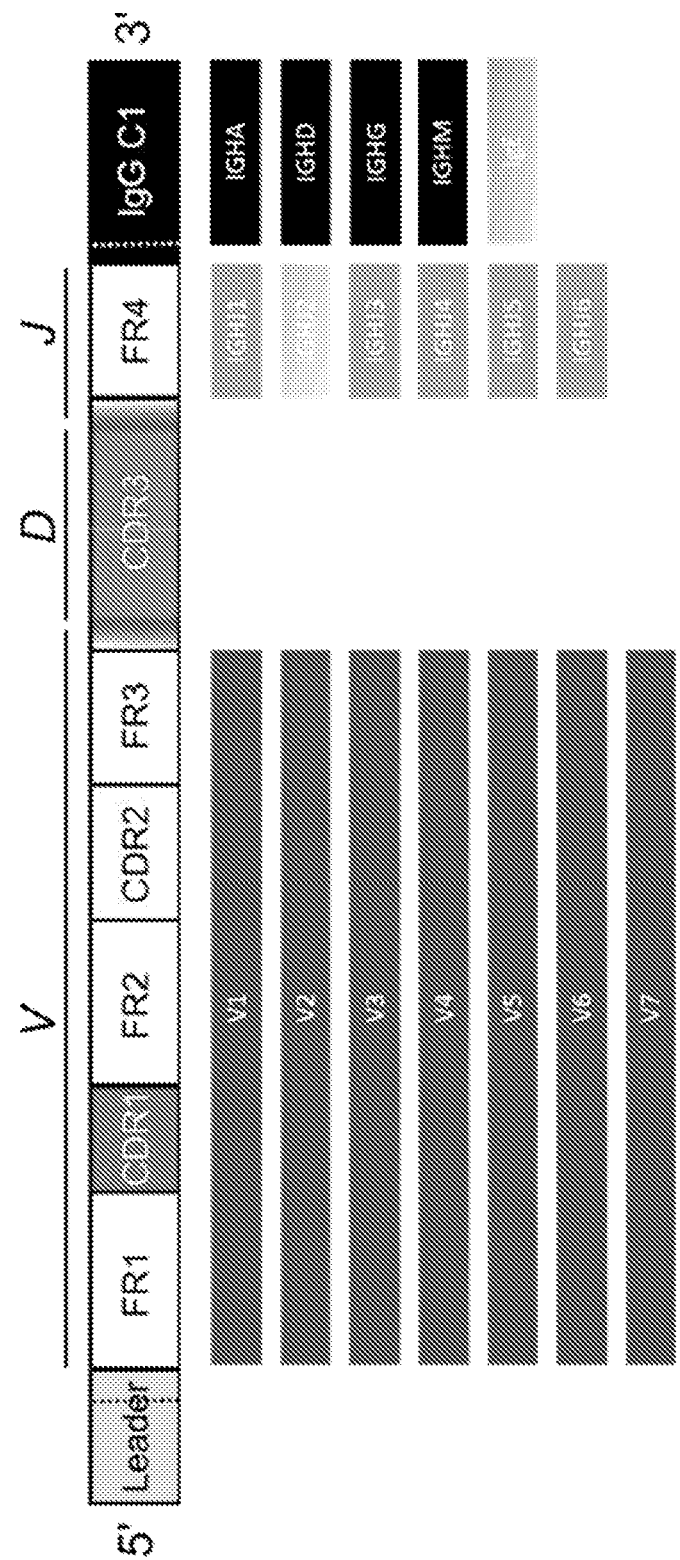
FIG. 11 illustrates the V (variable), J (joining) and H (heavy chain constant) regions of an Ig sequence. There are 7 distinct V-region families, 6 J-region families, and 5 different constant regions/Ig isotypes. Families of Igs share the same framework (FR) conserved regions, which may be targeted utilizing targeted primer sequences in the hybridization pad.

The immunoglobulin sequences clones can be broken down into different V (variable), J (joining) and H (heavy chain constant) regions. Within each region, there are multiple families where the antibody will share high sequence homology in the IBC-targeted sequences. For example, as illustrated in FIG. 11, there are 7 distinct V-region families, 6 J-region families, and 5 different constant regions/Ig isotypes. Families will share the same framework (FR) conserved region, which we designed different sets of IBCs to target. We created templates that contained a sampling of each one of the families, described in Table 1.

TABLE 1

Ig templates with known VDJ regions.

| Internal Ref No. | V region | D region | J region | IgG C1 region |
|---|---|---|---|---|
| C1245 | V1 | CDR3 | IGHJ4 | IGHD |
| C392 | V1 | CDR3 | IGHJ6 | IGHM |
| C719 | V2 | CDR3 | IGHJ3 | IGHG1 |
| C1113 | V2 | CDR3 | IGHJ6 | IGHM |
| C75 | V3 | CDR3 | IGHJ6 | IGHM |
| C479 | V4 | CDR3 | IGHJ4 | IGHA1 |
| C1051 | V4 | CDR3 | IGHJ6 | IGHM |
| C957 | V5 | CDR3 | IGHJ6 | IGHM |
| C77 | V6 | CDR3 | IGHJ5 | IGHM |
| C538 | V7 | CDR3 | IGHJ6 | IGHM |

Figure 12A:
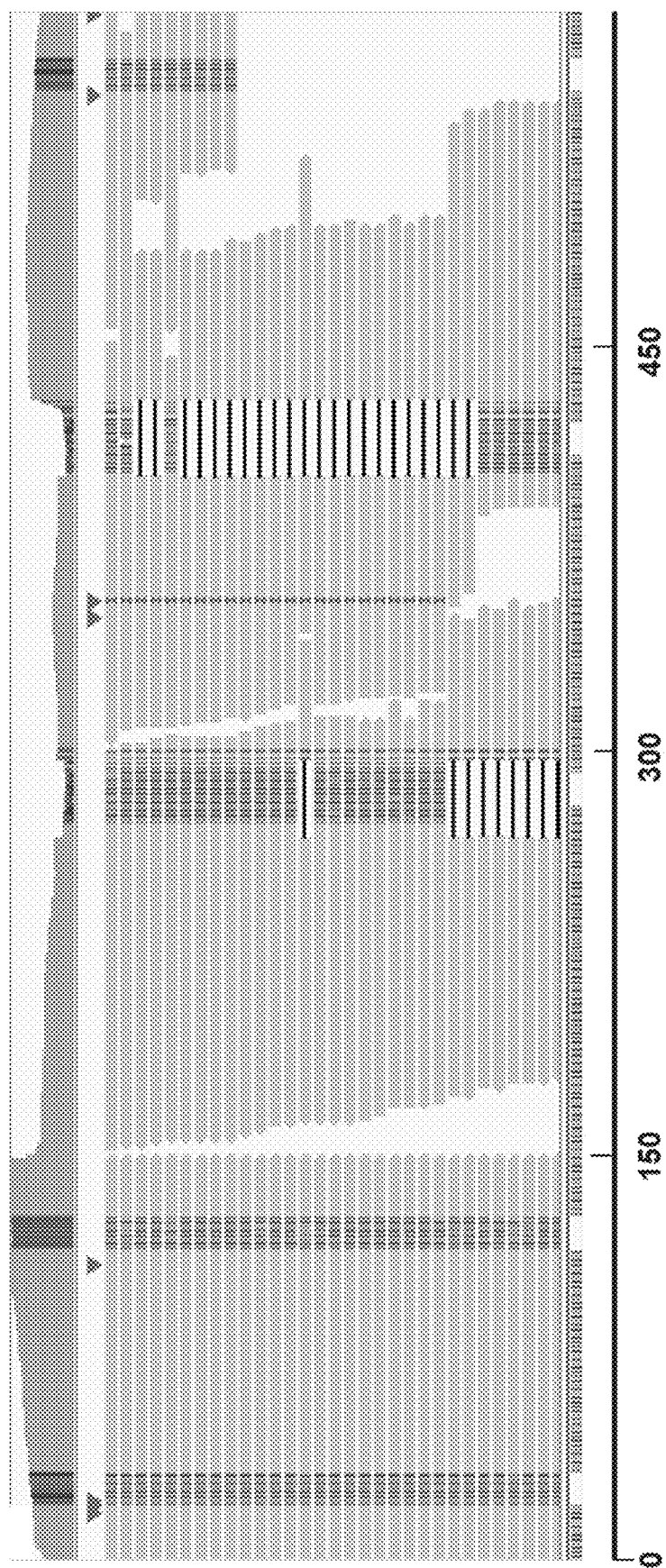
FIGS. 12A-12J shows the results of an IBC-based bioinformatic reconstruction of an antibody VDJ region for the following immunoglobulin (Ig) repertoires: C1245 (FIG. 12A); C392 (FIG. 12B); C719 (FIG. 12C); C1113 (FIG. 12D); C75 (FIG. 12E); C479 (FIG. 12F); C1051 (FIG. 12G); C957 (FIG. 12H); C77 (FIG. 12I); and C538 (FIG. 12J). The groups of vertical lines in the contig sequence represent each unique UMI that was used for aligning the reads. Each grey horizontal line represents a sequenced fragment, and a visual representation of the coverage is represented on the top. The arrows are indicative of at least one insertion event. The axis indicates nucleotide length.
Figure 12B:
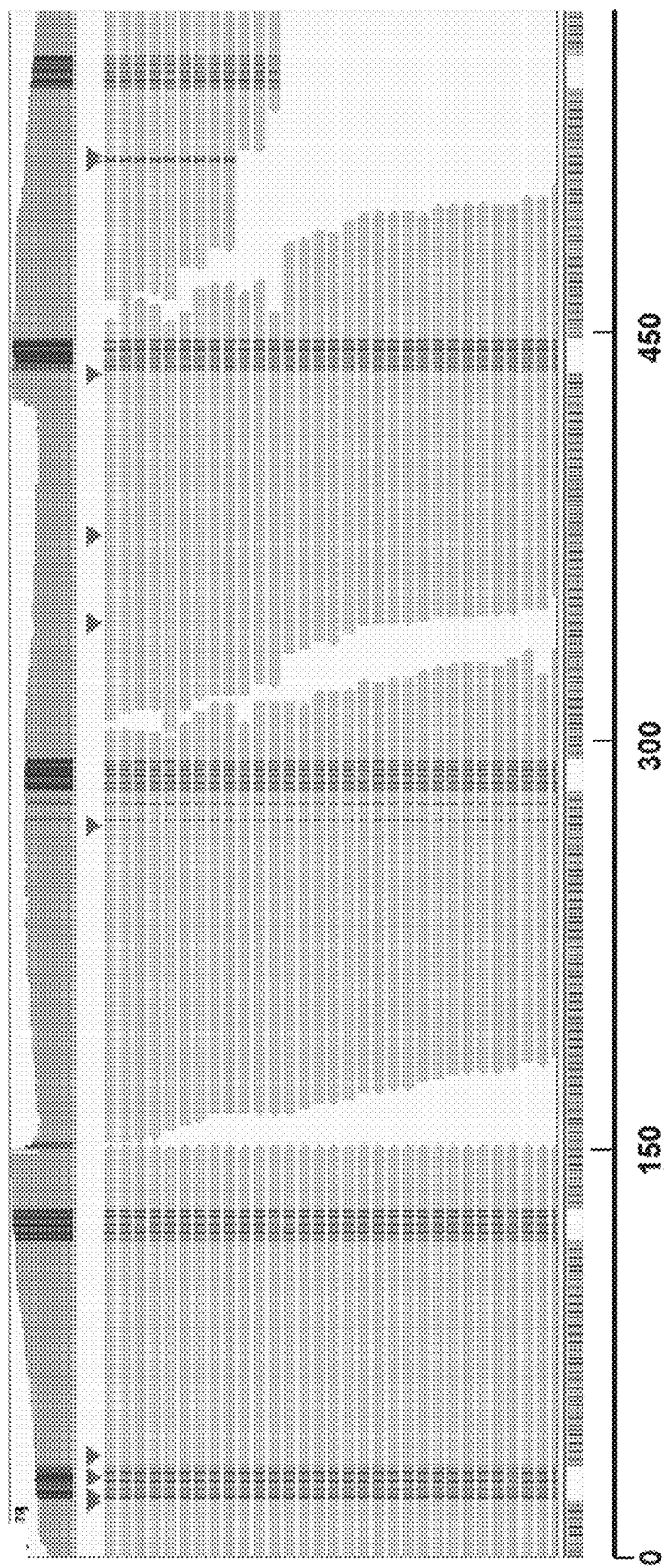
Figure 12C:
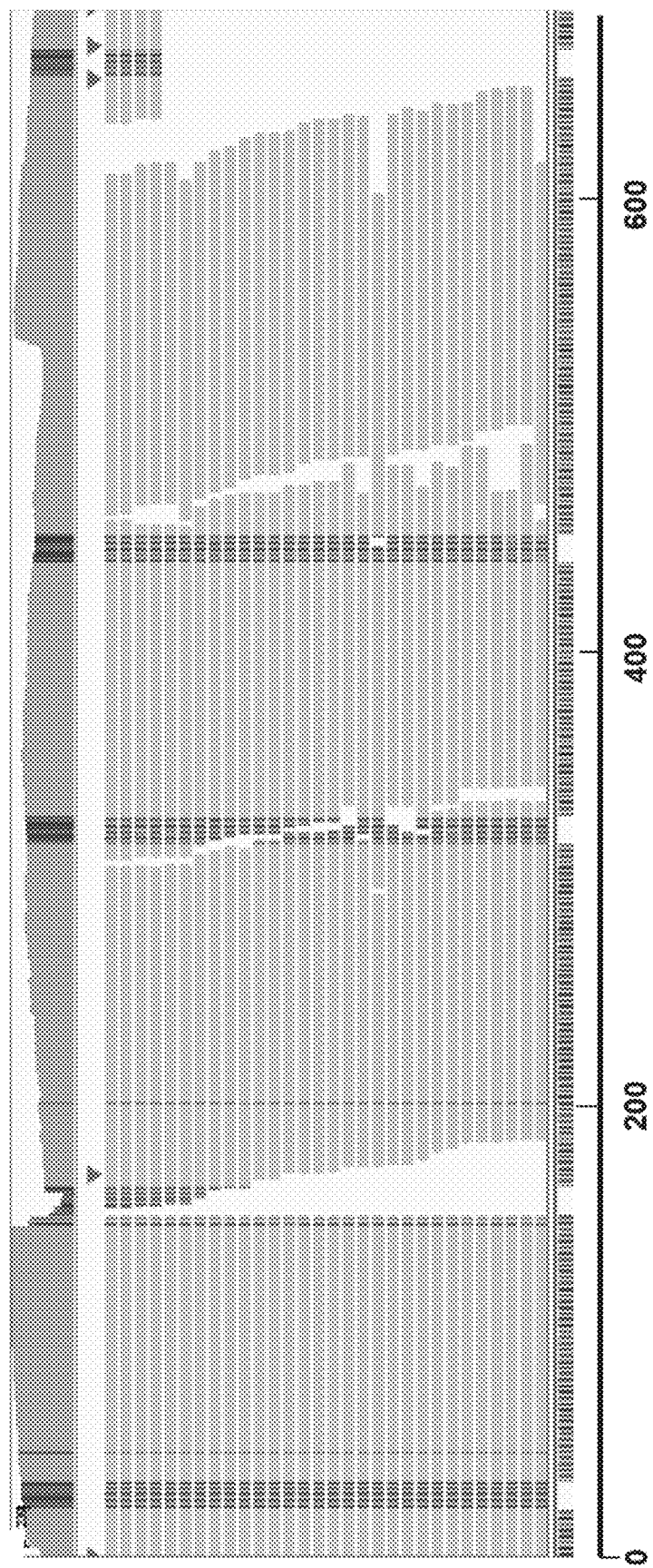
Figure 12D:
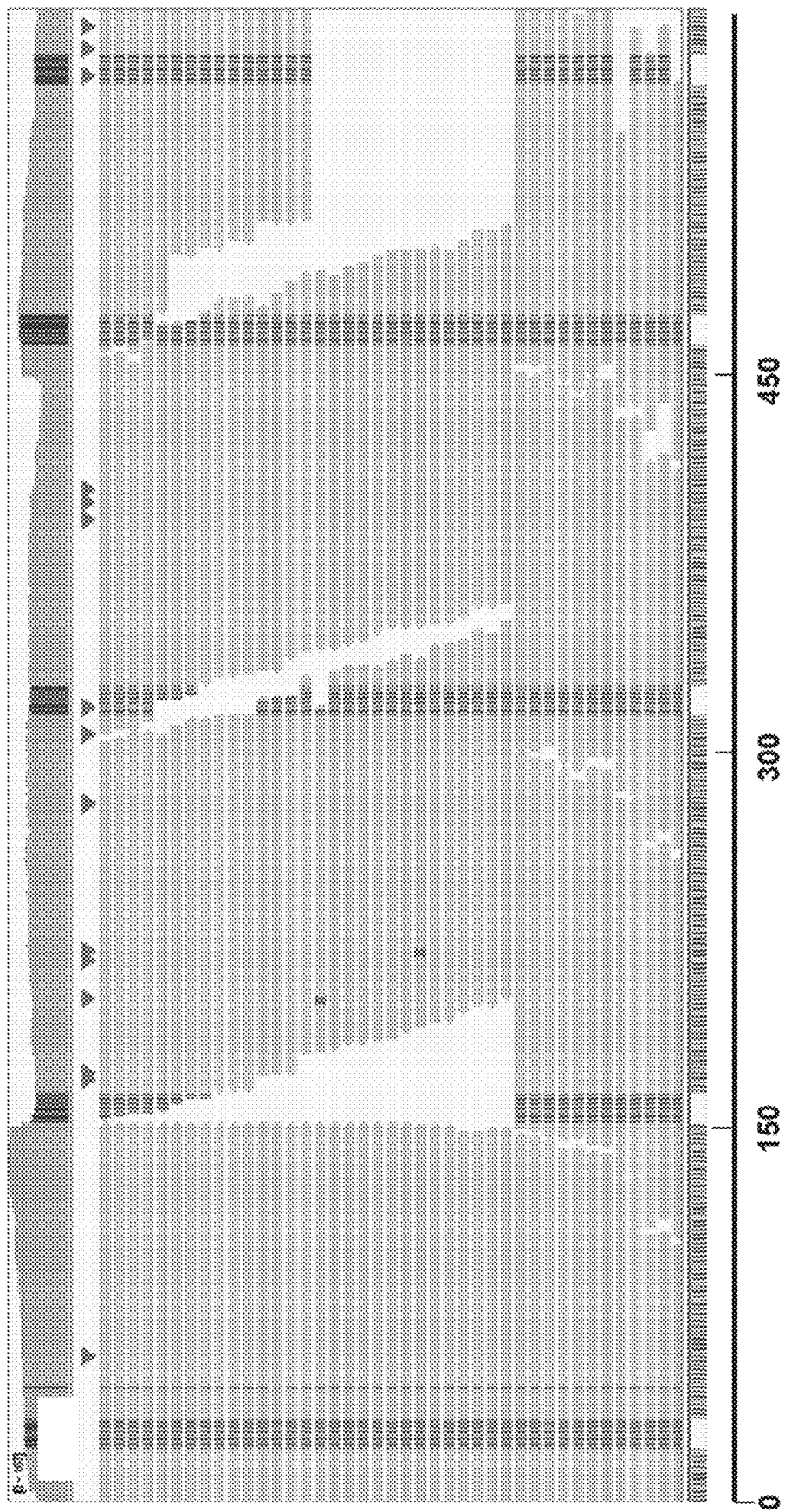
Figure 12E:
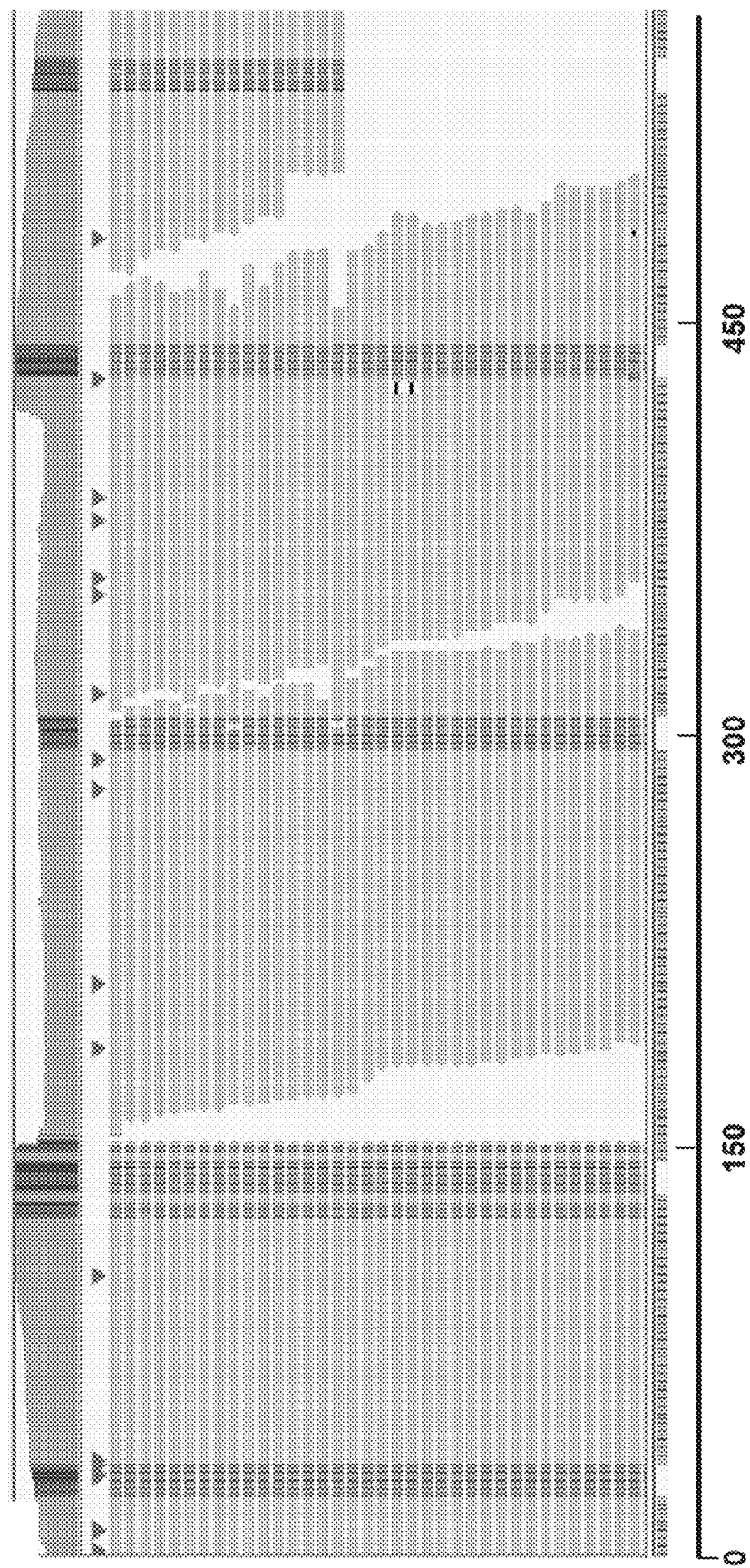
Figure 12F:
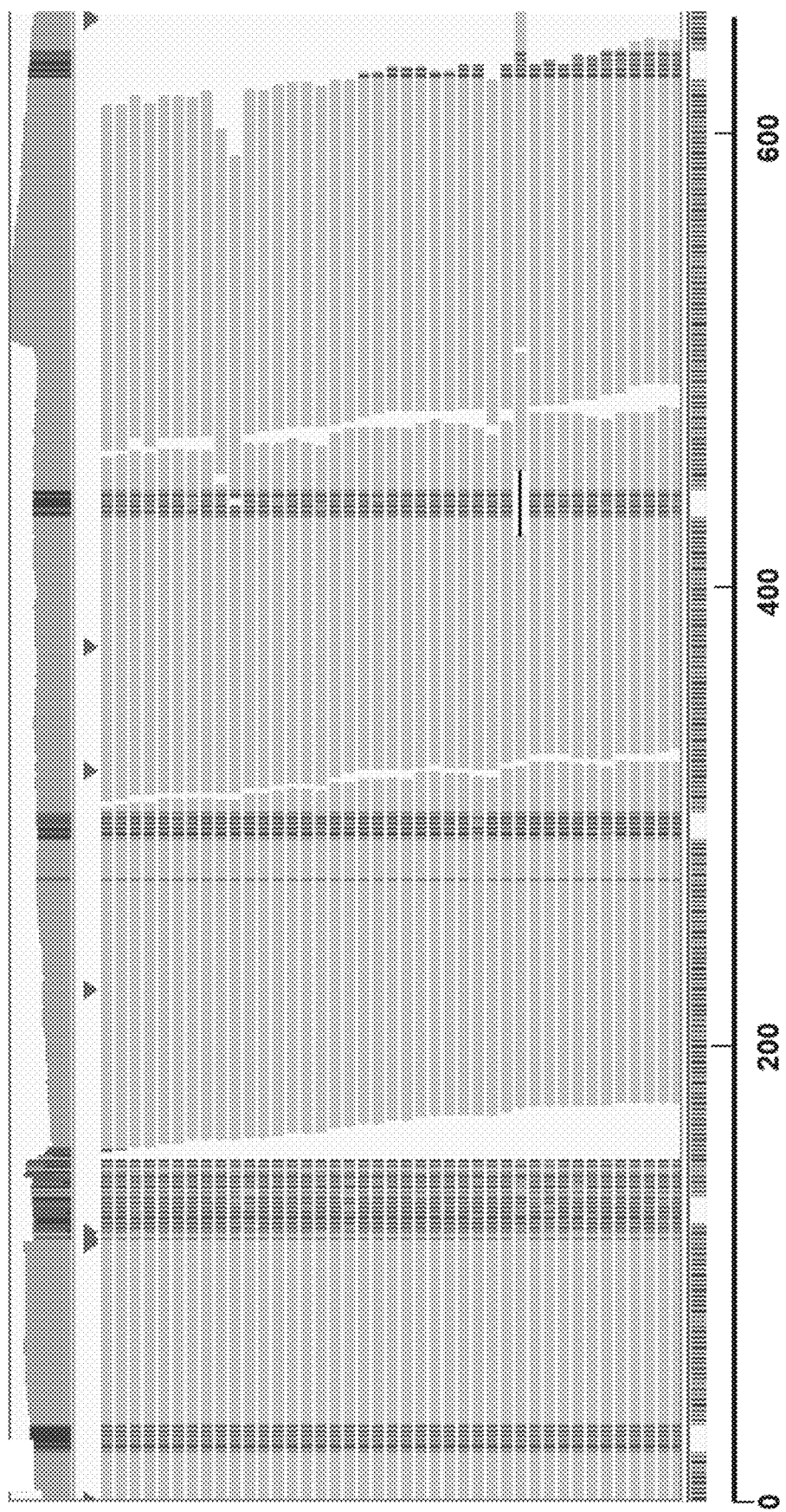
Figure 12G:
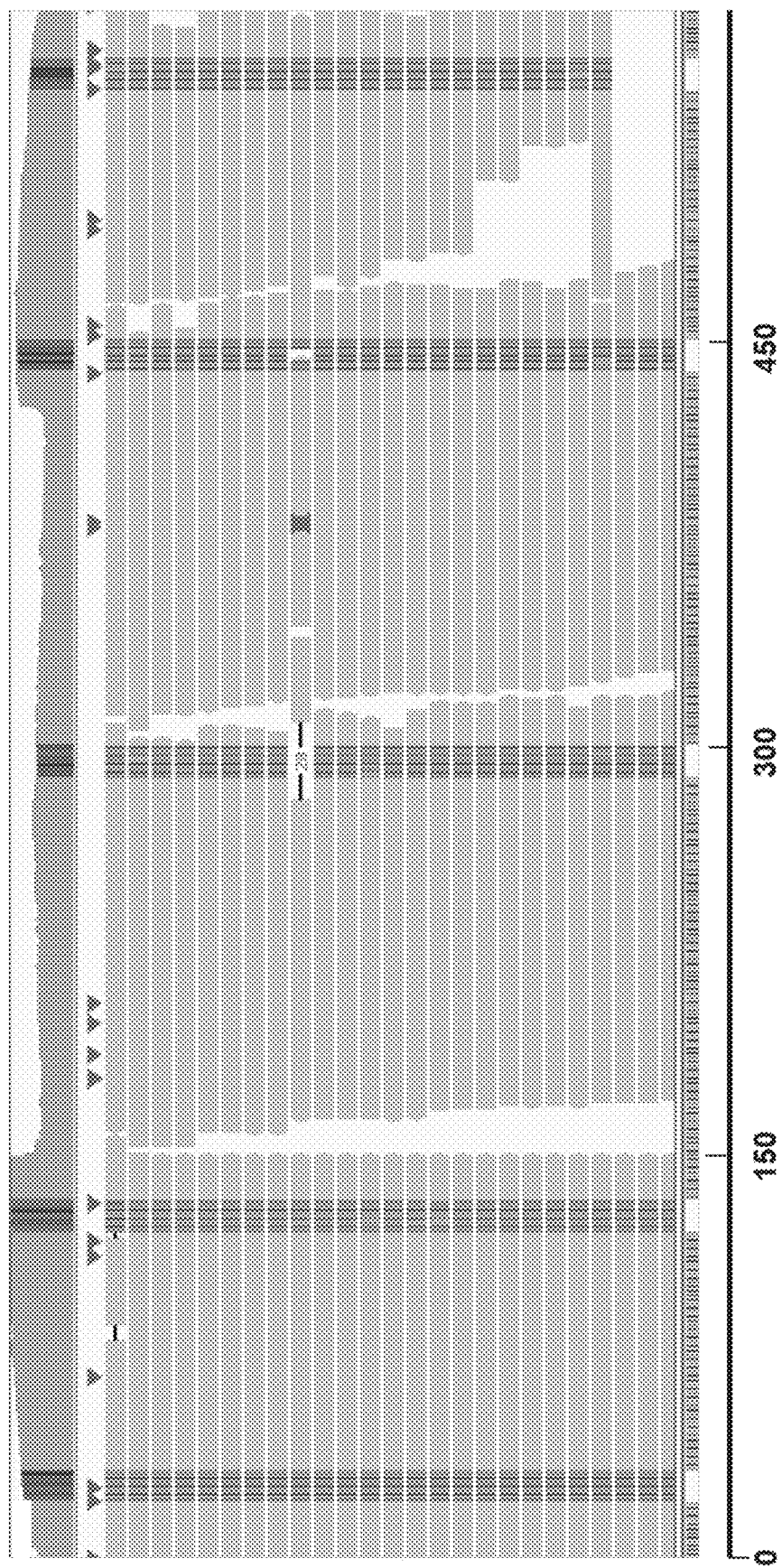
Figure 12H:
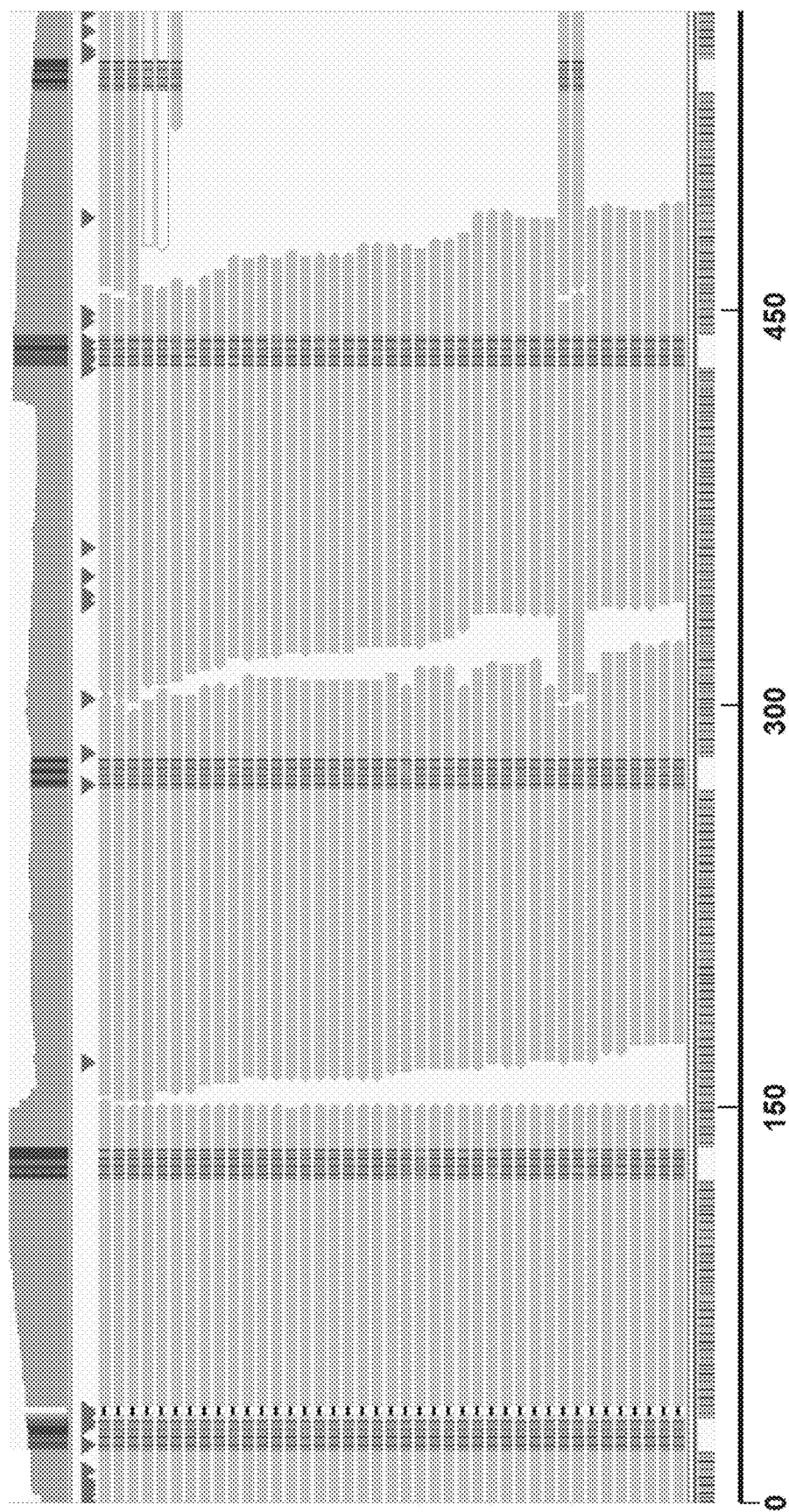
Figure 12I:
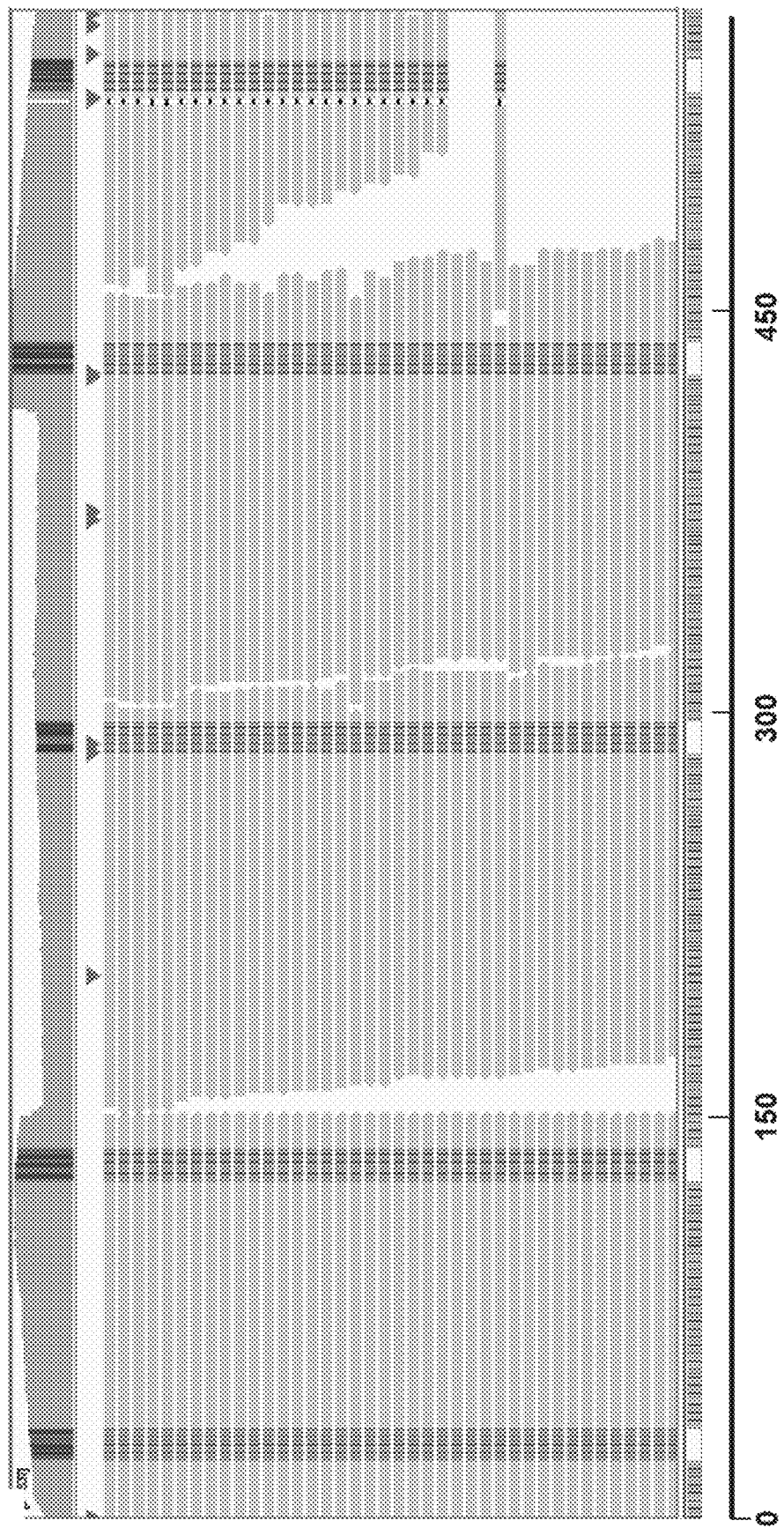
Figure 12J:
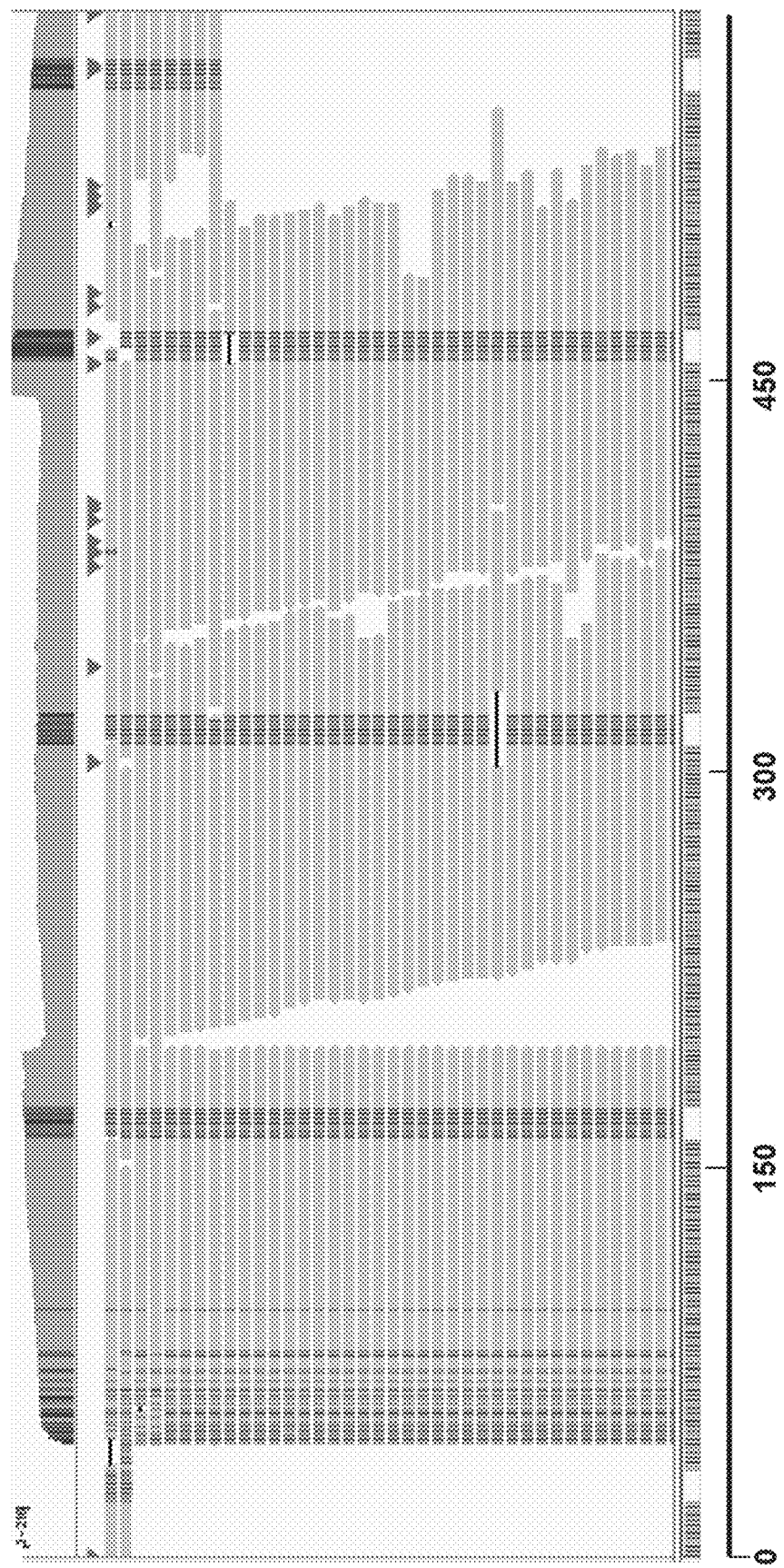

Shown in FIGS. 12A-12J are the reconstructed antibody VDJ regions for C1245 (FIG. 12A); C392 (FIG. 12B); C719 (FIG. 12C); C1113 (FIG. 12D); C75 (FIG. 12E); C479 (FIG. 12F); C1051 (FIG. 12G); C957 (FIG. 12H); C77 (FIG. 12I); and C538 (FIG. 12J) reconstructed using unique IBCs and the methods described herein. The arrows are indicative of at least one insertion event in one of the sequencing reads. Most of these insertions only occur in one or two reads while the consensus indicates there is no insertion event. There are only a few examples where an insertion is found to be consensus (see C392 at approximately 500 bp where all reads share the same insertion), indicating the methods described herein are capable of determining insertion events. The regularly spaced UMI signatures in the aligned sequences are successful indicators of the reconstructed long read. These results demonstrate the potential for long-range sequencing of templates with lengths ranging from at least 570 bp to over 1,700 bp.

Example 10: Pseudogene Analysis and Determination

Homopolymeric nucleic acid regions are repetitive elements that present major logistical and computational challenges for assembling fragments produced by traditional sequencing technologies, especially considering that approximately two-thirds of the sequence of the human genome consists of repetitive units. For example, the human genome includes minisatellite regions, repetitive motifs ranging in length from about 10-100 base pairs and can be repeated about 5 to 50 times in the genome, and short tandem repeats (STR), regions ranging in length from about 1-6 base pairs and can be repeated about 5 to 50 times in the genome (e.g., the sequence TATA is a dinucleotide STR). Complicating matters, mutations often lead to the gain or loss of an entire repeat unit, and sometimes two or more repeats simultaneously, which can significantly burden traditional sequencing methodologies.

The methods described herein are useful at identifying a pseudogene. A pseudogene is a nucleic acid region that has high sequence similarity (homology) to a known gene but is nonfunctional, that is, a pseudogene does not produce a functional final protein product that the parent gene produces. Usually, the DNA sequences of a pseudogene and of its functional parent gene are about 65% to 100% identical, and typically accumulate more variants than their parent genes.

Due to the relatively short length of the fragments of nucleic acids used in conventional NGS technologies, ranging in length from 35 to 600 base pairs, many technologies may struggle with accurately distinguishing pseudogenes from the parent gene. For example, if sequence reads containing a pseudogene-derived variant are inappropriately mapped to the parent gene, it may result in a false positive variant call. Similarly, if a parent gene-derived variant is inappropriately mapped to the pseudogene, it may result in a false negative result.

Complicating matters, it is estimated that humans have greater than 10,000 pseudogenes (Pei, B. et al. (2012). Genome biology, 13(9), R51). The ability to differentiate a gene from a pseudogene depends on the degree of homology between the duplicated region and the parent gene. Generally, variants in genes sharing 90%-98% homology with a pseudogene are still accurately detected and mapped. However, when the homology is greater than 98%, accurate detection and mapping of pseudogenes is challenging. For example, the ABCC6, ADAMTSL2, ANKRD11, BMPR1A, SDHA, GBA, CORO1A, HYDIN, HBA1/HBA2, CHEK2, SMN1/SMN2, PMS2, and BRAF exon 18 genes are typically challenging to correctly identify from their pseudogenes. In embodiments, identifying a disruption in the sequence relative to the parent gene (e.g., a missing promotor, missing start codon, frameshift, premature stop codon, missing introns, or partial deletion) is a useful way of identifying a pseudogene. In embodiments, the methods described herein allow for determining the sequence of long templates comprising such repetitive sequences. This greatly facilitates accurate assembly of sequence reads to determine the overall template sequence and identification of a pseudogene.

Briefly, an example interposing barcode is shown in FIG. 1A, and includes a loop region, a stem region, and two hybridization pads. The loop region includes about 15 random nucleotides, and may be referred to as molecular barcodes or unique molecular identifiers (UMIs). In embodiments of the methods described herein, the synthetic long reads are constructed by aligning all sequencing reads that contain the same UMI. In embodiments of the methods described herein, synthetic long reads are constructed by grouping together UMIs based on direct or indirect co-occurrence in the library, and then assembling the reads back into the original full-length molecule. In embodiments, the length of the UMI is optimized based on the total number of insertions sites (number of targeted molecules X number of insertion locations) to reduce the incorporation of two of the same UMIs in different molecules, while maximizing the amount of sequence in the read that is from the target molecule. Rare instances where the same UMI is observed in two different molecules can be addressed bioinformatically. Aside from forming the backbone for long read alignment, the introduction of UMIs into sequencing libraries prior to target amplification by PCR has been shown to dramatically increase the sensitivity for rare mutations and enable absolute read counting. The stem region includes two known sequences capable of hybridizing to each other, ranging from about 6 nucleotides, and is stable (i.e., capable to remaining hybridized together) at approximately a maximum temperature of 37° C., and unhybridizes (i.e., denatures) at temperatures greater than 50° C. Finally, the hybridization pads each includes about 9 to about 15 nucleotides and are capable of hybridizing to single stranded template nucleic acids (i.e., they are a complement to the original target). FIG. 1B depicts the interposing barcode when the stem regions are denatured.

To an isolated nucleic acid (e.g., a nucleic acid sequence containing a gene or pseudogene) sample interposing barcodes are added at an appropriate concentration such that there are approximately 50-100 bases between each IBC (e.g., see Example 8 for additional details). A non strand-displacing sequencing polymerase (e.g., Klentaq, T4, T7, Bst, Phusion, Tfl, Pfu, or Stoffel fragment) extends the complement strand to generate an extension segment, as shown in FIG. 2A, and a ligase ligates the ends of the extension segment together with the next interposing barcode to produce a single integrated strand, as depicted in FIG. 2B. Optionally, the template DNA sample is washed away or degraded, and the resultant integrated strand may be subjected to reaction conditions (e.g., elevated temperature or denaturing additives) such that the stem regions of interposing barcodes and/or any secondary structures present denature to form a linear integrated strand, as schematically shown in FIG. 2C. The integrated strand may be amplified using methods known to those skilled in the art (e.g., standard PCR amplification or rolling circle amplification) and subjected to standard library preparation methods as known to those skilled in the art and described herein.

The input DNA (i.e., the integrated strand) is fragmented to make small DNA molecules with a modal size of about 100 to about 200 base pairs with random ends. The resulting DNA fragments generated by sonication will be end polished to produce a library of DNA fragments with blunt, 5'-phosphorylated ends that are ready for ligation. The end polishing is accomplished by using the T4 DNA polymerase, which can fill in 5' overhangs via its polymerase activity and recess 3' overhangs via its 3'-5' exonuclease activity. The phosphorylation of 5' ends is accomplished by T4 polynucleotide kinase.

Adapter ligation: Ligation of double-stranded DNA adapters is accomplished by use of T4 DNA ligase. Depending on the adapter, some double-stranded adapters may not have 5' phosphates and contain a 5' overhang on one end to prevent ligation in the incorrect orientation. Now the adapter-ligated library may be size-selected (e.g., selecting for approximately 200-250 base pair size range). By doing this, unligated adapters and adapter dimers are removed, and the optimal size-range for subsequent PCR and sequencing is selected. Any suitable clean up method known to those skilled in the art may be used, such as magnetic bead-based clean up, or purification on agarose gels.

The resultant strand is then subjected to a nucleic acid sequencing reaction using any available sequencing technology. Once data is available from the sequencing reaction, initial processing (often termed "pre-processing") of the sequences is typically employed prior to annotation. Pre-processing includes filtering out low-quality sequences, sequence trimming to remove continuous low-quality nucleotides, merging paired-end sequences, or identifying and filtering out PCR repeats using known techniques in the art. The sequenced reads may then be assembled and aligned using bioinformatic algorithms known in the art (e.g., as depicted in FIG. 3 and FIG. 14).

P-Embodiments

The present disclosure provides the following illustrative embodiments.

Embodiment P1. A method of making tagged complements of a plurality of sample polynucleotides, the method comprising: a. hybridizing to each of the plurality of sample polynucleotides a plurality of interposing oligonucleotide barcodes, each of the interposing oligonucleotide barcodes comprising from 5' to 3': i. a first hybridization pad complementary to a first sequence of a sample polynucleotide; ii. a first stem region comprising a sequence common to the plurality of interposing oligonucleotide barcodes; iii. a loop region comprising a barcode sequence, wherein the barcode sequence, alone or in combination with a sequence of one or both of (a) the sample polynucleotide, or (b) one or more additional barcode sequences, uniquely distinguishes the sample polynucleotide from other sample polynucleotides in the plurality; iv. a second stem region comprising a sequence complementary to the first stem region, wherein the second stem region is capable of hybridizing to the first stem region under hybridization conditions; and v. a second hybridization pad complementary to a second sequence of the sample polynucleotide; b. extending the 3' ends of the adapters with one or more polymerases to create extension products; and c. ligating adjacent ends of extension products hybridized to the same sample polynucleotide thereby making complements of the plurality of sample polynucleotides tagged with a plurality of interposing oligonucleotide barcodes.

Embodiment P2. The method of Embodiment P1, wherein each of the interposing oligonucleotide barcodes comprise a phosphorylated 5' end.

Embodiment P3. The method of Embodiment P1, wherein the method comprises phosphorylating the 5' ends of the interposing oligonucleotide barcodes prior to step (c).

Embodiment P4. The method of one of Embodiment P1 to Embodiment P3, wherein each hybridization pad comprises about 3 to about 5 nucleotides.

Embodiment P5. The method of one of Embodiment P1 to Embodiment P4, wherein the first and second stem regions are complementary and wherein each stem region comprises a known sequence of about 5 to about 10 nucleotides.

Embodiment P6. The method of one of Embodiment P1 to Embodiment P5, wherein the loop region comprises about 5 to about 20 nucleotides, or about 10 to about 20 nucleotides.

Embodiment P7. The method of one of Embodiment P1 to Embodiment P6, wherein each barcode sequence is selected from a set of barcode sequences represented by a random or partially random sequence.

Embodiment P8. The method of one of Embodiment P1 to Embodiment P7, wherein each barcode sequence is selected from a set of barcode sequences represented by a random sequence.

Embodiment P9. The method of one of Embodiment P1 to Embodiment P8, wherein the loop region further comprises a sample index sequence.

Embodiment P10. The method of one of Embodiment P1 to Embodiment P9, wherein each barcode sequence differs from every other barcode sequence by at least two nucleotide positions.

Embodiment P11. The method of one of Embodiment P1 to Embodiment P10, further comprising sequencing the tagged complements.

Embodiment P12. The method of Embodiment P11, wherein the sequencing comprises (a) amplifying the tagged complements of the plurality of sample polynucleotides by an amplification reaction thereby making amplified products; and (b) performing a sequencing reaction on the amplified products.

Embodiment P13. The method of Embodiment P11, wherein the sequencing comprises (a) amplifying the tagged complements of the plurality of sample polynucleotides thereby making amplified products; (b) fragmenting the amplified products to produce fragments, (c) ligating adapters to the fragments, (d) amplifying the resultant products from step (c) to generate a polynucleotide, and (e) performing a sequencing reaction on the polynucleotide from step (d).

Embodiment P14. The method of Embodiment P12 or Embodiment P13, wherein the sequencing reaction comprises (i) immobilizing a polynucleotide to be sequenced on a solid support; (ii) hybridizing a sequencing primer to the immobilized polynucleotide; (iii) performing cycles of primer extension with a polymerase and labeled nucleotides to generate an extended sequencing primer and (iv) detecting the labeled nucleotides to determine the sequence of the immobilized polynucleotide.

Embodiment P15. The method of one of Embodiment P11 to Embodiment P14, wherein the sequencing further comprises (a) producing a plurality of sequencing reads; (b) aligning a portion of each sequencing read to a reference sequence; and (c) grouping sequencing reads that belong to the same strand of an original sample polynucleotide based on the aligning and sequences of the barcode sequences.

Embodiment P16. The method of one of Embodiment P11 to Embodiment P15, wherein the sequencing reaction comprises sequencing by synthesis, sequencing by ligation, or pyrosequencing.

Embodiment P17. The method of Embodiment P15, wherein each of the sequencing reads comprise at least a portion of two or more barcode sequences, or complements thereof.

Embodiment P18. The method of one of Embodiment P15 to Embodiment P17, wherein the reference sequence is a reference genome.

Embodiment P19. The method of one of Embodiment P15 to Embodiment P18, further comprising forming a consensus sequence for reads having the same barcode sequence.

Embodiment P20. The method of one of Embodiment P15 to Embodiment P19, further comprising computationally reconstructing sequences of a plurality of individual strands of original sample polynucleotides by removing interposing oligonucleotide barcode-derived sequences and joining sequences for adjacent portions of the sample polynucleotide.

Embodiment P21. The method of Embodiment P20, further comprising aligning computationally reconstructed sequences.

Embodiment P22. A plurality of interposing oligonucleotide barcodes capable of hybridizing to a sample polynucleotide, the interposing oligonucleotide barcodes comprising from 5' to 3': i. a first hybridization pad complementary to a first sequence of the sample polynucleotide; ii. a first stem region comprising a sequence common to the plurality of interposing oligonucleotide barcodes; iii. a loop region comprising a barcode sequence, wherein the barcode sequence, alone or in combination with a sequence of one or both of (a) the sample polynucleotide, or (b) one or more additional barcode sequences, uniquely distinguishes the sample polynucleotide from other sample polynucleotides in the plurality; iv. a second stem region comprising a sequence complementary to the first stem region, wherein the second stem region is capable of hybridizing to the first stem region under hybridization conditions; and v. a second hybridization pad complementary to a second sequence of the sample polynucleotide.

Embodiment P23. The interposing oligonucleotide barcodes of Embodiment P22, wherein each hybridization pad comprises about 3 to about 5 nucleotides.

Embodiment P24. The interposing oligonucleotide barcodes of Embodiment P22 or Embodiment P23, wherein the first and second stem regions are complementary and wherein each stem region comprises a known sequence of about 5 to about 10 nucleotides.

Embodiment P25. The interposing oligonucleotide barcodes of Embodiment P22, wherein the first stem region and the second stem region further comprise a sample index sequence.

Embodiment P26. The interposing oligonucleotide barcodes of any of Embodiment P22 to Embodiment P24, wherein the barcode sequence comprises about 5 to about 20 nucleotides, or about 10 to about 20 nucleotides.

Embodiment P27. The interposing oligonucleotide barcodes of any of Embodiment P22 to Embodiment P26, wherein each barcode sequence is selected from a set of barcode sequences represented by a random or partially random sequence.

Embodiment P28. The interposing oligonucleotide barcodes of any of Embodiment P22 to Embodiment P27, wherein each barcode sequence is selected from a set of barcode sequences represented by a random sequence.

Embodiment P29. The interposing oligonucleotide barcodes of Embodiment P28, wherein random sequence excludes a subset of sequences, wherein the excluded subset comprises sequences with three or more identical consecutive nucleotides.

Embodiment P30. The interposing oligonucleotide barcodes of Embodiment P28, wherein each barcode sequence differs from every other barcode sequence by at least two nucleotide positions.

Embodiment P31. The interposing oligonucleotide barcodes of any of Embodiment P22 to Embodiment P30, wherein the interposing oligonucleotide barcodes comprise a 5' phosphate.

Embodiment P32. A composition comprising a sample polynucleotide hybridized to the plurality of oligonucleotides barcodes of any of Embodiment P22 to Embodiment P31.

Embodiment P33. The composition of Embodiment P32, wherein the second hybridization pad is at least twice as long as the first hybridization pad.

Embodiment P34. A polynucleotide comprising a plurality of units, wherein each unit comprises a portion of a genomic sequence and a sequence of an interposing oligonucleotide barcode, wherein each interposing oligonucleotide barcode comprises from 5' to 3': a. a first stem region comprising a sequence common to the plurality of units; b. a loop region comprising a barcode sequence, wherein each barcode sequence in the polynucleotide is different; and c. a second stem region comprising a sequence complementary to the first stem region, wherein the second stem region hybridizes to the first stem region during said hybridizing.

Embodiment P35. The polynucleotide of Embodiment P34, wherein the polynucleotide comprises three or more units.

Embodiment P36. The polynucleotide of Embodiment P34 or Embodiment P35, wherein each hybridization pad comprises about 3 to about 5 nucleotides of random sequence.

Embodiment P37. The polynucleotide of any of Embodiment P34 to Embodiment P36, wherein the first and second stem regions are complementary and wherein each stem region comprises a known sequence of about 5 to about 10 nucleotides.

Embodiment P38. The polynucleotides of any of Embodiment P34 to Embodiment P37, wherein the barcode sequence comprises about 5 to about 20 nucleotides, or about 10 to about 20 nucleotides.

Embodiment P39. The polynucleotides of any of Embodiment P34 to Embodiment P38, wherein each barcode sequence is selected from a set of barcode sequences represented by a random or partially random sequence.

Embodiment P40. The polynucleotides of any of Embodiment P34 to Embodiment P39, wherein each barcode sequence is selected from a set of barcode sequences represented by a random sequence.

Embodiment P41. The polynucleotides of Embodiment P40, wherein the first stem region and the second stem region further comprise a sample index sequence.

Embodiment P42. The polynucleotides of any of Embodiment P34 to Embodiment P41, wherein each barcode sequence differs from every other barcode sequence by at least two nucleotide positions.

Embodiment P43. The polynucleotides of any of Embodiment P34 to Embodiment P42, wherein the interposing oligonucleotide barcodes comprise a 5' phosphate moiety.

Embodiment P44. A plurality of polynucleotides of any of Embodiment P34 to Embodiment P43, wherein each polynucleotide in the plurality comprises a different combination of barcode sequences.

Embodiment P45. A plurality of tagged complements of a plurality of sample polynucleotides, produced according to the method of any of Embodiment P1 to Embodiment P21.

Embodiment P46. A kit comprising a plurality of oligonucleotides barcodes of any of Embodiment P22 to Embodiment P31.

Additional Embodiments

The present disclosure provides the following additional illustrative embodiments.

Embodiment 1. A method of amplifying tagged complements of a plurality of sample polynucleotides, the method comprising:
a. hybridizing to each of the plurality of sample polynucleotides a plurality of interposing oligonucleotide barcodes, each of the interposing oligonucleotide barcodes comprising from 5' to 3':
   i. a first hybridization pad complementary to a first sequence of a sample polynucleotide;
   ii. a first stem region comprising a sequence common to the plurality of interposing oligonucleotide barcodes;
   iii. a loop region comprising a barcode sequence, wherein the barcode sequence, alone or in combination with a sequence of one or both of (a) the sample polynucleotide, or (b) one or more additional barcode sequences, uniquely distinguishes the sample polynucleotide from other sample polynucleotides in the plurality;
    iv. a second stem region comprising a sequence complementary to the first stem region, wherein the second stem region is capable of hybridizing to the first stem region under hybridization conditions; and
    v. a second hybridization pad complementary to a second sequence of the sample polynucleotide;
  b. extending the 3' ends of the second hybridization pads with one or more polymerases to create extension products; and
  c. ligating adjacent ends of extension products hybridized to the same sample polynucleotide thereby making integrated strands comprising complements of the plurality of sample polynucleotides tagged with a plurality of interposing oligonucleotide barcodes; and
  d. amplifying the integrated strands by an amplification reaction thereby amplifying the tagged complements of the plurality of sample polynucleotides.

Embodiment 2. The method of embodiment 1, wherein each of the interposing oligonucleotide barcodes comprise a phosphorylated 5' end.

Embodiment 3. The method of embodiment 1, wherein the method comprises phosphorylating the 5' ends of the interposing oligonucleotide barcodes prior to step (c).

Embodiment 4. The method of any one of embodiments 1-3, wherein each hybridization pad comprises about 9 to about 15 nucleotides.

Embodiment 5. The method of any one of embodiments 1-3, wherein each hybridization pad comprises about 8 to about 12 nucleotides.

Embodiment 6. The method of any one of embodiments 1-3, wherein each hybridization pad comprises a targeted primer sequence.

Embodiment 7. The method of any one of embodiments 1-3, wherein each hybridization pad comprises at least one locked nucleic acid.

Embodiment 8. The method of any one of embodiments 1-3, wherein the total combined length of the first hybridization pad and the second hybridization pad comprises about 18 to about 25 nucleotides.

Embodiment 9. The method of any one of embodiments 1-7, wherein the first and second stem regions are complementary and wherein each stem region comprises a known sequence of about 5 to about 10 nucleotides.

Embodiment 10. The method of any one of embodiments 1-7, wherein the first and second stem regions are complementary and wherein each stem region comprises a known sequence of about 6 to about 8 nucleotides.

Embodiment 11. The method of any one of embodiments 1-10, wherein the loop region comprises about 5 to about 20 nucleotides, or about 10 to about 20 nucleotides.

Embodiment 12. The method of any one of embodiments 1-10, wherein the loop region comprises about 12 to about 16 nucleotides.

Embodiment 13. The method of any one of embodiments 1-12, wherein each barcode sequence is selected from a set of barcode sequences represented by a random or partially random sequence.

Embodiment 14. The method of any one of embodiments 1-12, wherein each barcode sequence is selected from a set of barcode sequences represented by a random sequence.

Embodiment 15. The method of any one of embodiments 1-14, wherein the loop region further comprises a sample index sequence.

Embodiment 16. The method of any one of embodiments 1-15, wherein each barcode sequence differs from every other barcode sequence by at least two nucleotide positions.

Embodiment 17. The method of any one of embodiments 1-16, wherein the sample polynucleotides comprise a gene or a gene fragment.

Embodiment 18. The method of embodiment 17, wherein the gene or gene fragment is a cancer-associated gene or fragment thereof, T cell receptor (TCRs) gene or fragment thereof, or a B cell receptor (BCRs) gene, or fragment thereof.

Embodiment 19. The method of embodiment 17, wherein the gene or gene fragment is a CDR3 gene or fragment thereof, T cell receptor alpha variable (TRAV) gene or fragment thereof, T cell receptor alpha joining (TRAJ) gene or fragment thereof, T cell receptor alpha constant (TRAC) gene or fragment thereof, T cell receptor beta variable (TRBV) gene or fragment thereof, T cell receptor beta diversity (TRBD) gene or fragment thereof, T cell receptor beta joining (TRBJ) gene or fragment thereof, T cell receptor beta constant (TRBC) gene or fragment thereof, T cell receptor gamma variable (TRGV) gene or fragment thereof, T cell receptor gamma joining (TRGJ) gene or fragment thereof, T cell receptor gamma constant (TRGC) gene or fragment thereof, T cell receptor delta variable (TRDV) gene or fragment thereof, T cell receptor delta diversity (TRDD) gene or fragment thereof, T cell receptor delta joining (TRDJ) gene or fragment thereof, or T cell receptor delta constant (TRDC) gene or fragment thereof.

Embodiment 20. The method of any one of embodiments 1-16, wherein the sample polynucleotides comprise genomic DNA, complementary DNA (cDNA), cell-free DNA (cfDNA), messenger RNA (mRNA), transfer RNA (tRNA), ribosomal RNA (rRNA), cell-free RNA (cfRNA), or non-coding RNA (ncRNA).

Embodiment 21. The method of any one of embodiments 1-16, wherein the sample polynucleotides comprise messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA).

Embodiment 22. The method of any one of embodiments 1-21, wherein amplifying comprises hybridizing an amplification primer to the integrated strands and cycles of primer extension with a polymerase and nucleotides to generate amplified products.

Embodiment 23. The method of any one of embodiments 1-21, wherein the amplification reaction comprises polymerase chain reaction (PCR), strand displacement amplification (SDA), multiple displacement amplification (MDA), ligation chain reaction, transcription mediated amplification (TMA), nucleic acid sequence based amplification (NASBA), rolling circle amplification (RCA), exponential rolling circle amplification (eRCA), hyperbranched rolling circle amplification (HRCA), or a combination thereof.

Embodiment 24. The method of any one of embodiments 1-23, further comprising hybridizing to each of the plurality of sample polynucleotides a terminal adapter, wherein the terminal adapter comprises a first hybridization pad complementary to a first sequence of a sample polynucleotide, a barcode sequence, and a primer binding sequence.

Embodiment 25. The method of embodiment 24, wherein amplifying comprises hybridizing an amplification primer to the primer binding sequence of the terminal adapter and cycles of primer extension with a polymerase and nucleotides to generate amplified products.

Embodiment 26. The method of any one of embodiments 1-25, further comprising sequencing the amplified products of step (d).

Embodiment 27. The method of embodiment 26, wherein the sequencing comprises: (A) fragmenting the amplified products to produce fragments, (B) ligating adapters to the fragments, (C) amplifying the resultant products from step (B) to generate a polynucleotide, and (D) performing a sequencing reaction on the polynucleotide from step (C).

Embodiment 28. The method of embodiments 26 or 27, wherein the sequencing comprises (i) immobilizing a polynucleotide to be sequenced on a solid support; (ii) hybridizing a sequencing primer to the immobilized polynucleotide; (iii) performing cycles of primer extension with a polymerase and labeled nucleotides to generate an extended sequencing primer and (iv) detecting the labeled nucleotides to determine the sequence of the immobilized polynucleotide.

Embodiment 29. The method of any one of embodiments 26-28, wherein the sequencing further comprises (a) producing a plurality of sequencing reads; (b) aligning a portion of each sequencing read to a reference sequence; and (c) grouping sequencing reads that belong to the same strand of an original sample polynucleotide based on the aligning and sequences of the barcode sequences.

Embodiment 30. The method of any one of embodiments 26-28, wherein the sequencing further comprises (a) producing a plurality of sequencing reads; (b) grouping sequencing reads based on co-occurrence of barcode sequences; and (c) within each group, aligning the reads that belong to the same strand of an original sample polynucleotide based on the sequences of the barcode sequences.

Embodiment 31. The method of any one of embodiments 26-30, wherein the sequencing comprises sequencing by synthesis, sequencing by ligation, or pyrosequencing.

Embodiment 32. The method of embodiment 29 or 30, wherein each of the sequencing reads comprise at least a portion of two or more barcode sequences, or complements thereof.

Embodiment 33. The method of embodiment 29 or 30, wherein the reference sequence is a reference genome.

Embodiment 34. The method of any one of embodiments 29-33, further comprising forming a consensus sequence for reads having the same barcode sequence.

Embodiment 35. The method of any one of embodiments 29-34, further comprising computationally reconstructing sequences of a plurality of individual strands of original sample polynucleotides by removing interposing oligonucleotide barcode-derived sequences and joining sequences for adjacent portions of the sample polynucleotide.

Embodiment 36. The method of embodiment 35, further comprising aligning computationally reconstructed sequences.

Embodiment 37. A plurality of interposing oligonucleotide barcodes capable of hybridizing to a sample polynucleotide, the interposing oligonucleotide barcodes comprising from 5' to 3':
  i. a first hybridization pad complementary to a first sequence of the sample polynucleotide;
  ii. a first stem region comprising a sequence common to the plurality of interposing oligonucleotide barcodes;
  iii. a loop region comprising a barcode sequence, wherein the barcode sequence, alone or in combination with a sequence of one or both of (a) the sample polynucleotide, or (b) one or more additional barcode sequences, uniquely distinguishes the sample polynucleotide from other sample polynucleotides in the plurality;
  iv. a second stem region comprising a sequence complementary to the first stem region, wherein the second stem region is capable of hybridizing to the first stem region under hybridization conditions; and
  v. a second hybridization pad complementary to a second sequence of the sample polynucleotide.

Embodiment 38. The interposing oligonucleotide barcodes of embodiment 37, wherein each hybridization pad comprises about 9 to about 15 nucleotides.

Embodiment 39. The interposing oligonucleotide barcodes of embodiment 37, wherein each hybridization pad comprises about 8 to about 12 nucleotides.

Embodiment 40. The interposing oligonucleotide barcodes of embodiment 37, wherein each hybridization pad comprises a targeted primer sequence.

Embodiment 41. The interposing oligonucleotide barcodes of embodiment 37, wherein each hybridization pad comprises a at least one locked nucleic acid.

Embodiment 42. The interposing oligonucleotide barcodes of embodiment 37, wherein the total combined length of the first hybridization pad and the second hybridization pad comprises about 18 to about 25 nucleotides.

Embodiment 43. The interposing oligonucleotide barcodes of any one of embodiments 37 to 42, wherein the first and second stem regions are complementary and wherein each stem region comprises a known sequence of about 5 to about 10 nucleotides.

Embodiment 44. The interposing oligonucleotide barcodes of any one of embodiments 37 to 42, wherein the first and second stem regions are complementary and wherein each stem region comprises a known sequence of about 6 to about 8 nucleotides.

Embodiment 45. The interposing oligonucleotide barcodes of embodiment 37, wherein the first stem region and the second stem region further comprise a sample index sequence.

Embodiment 46. The interposing oligonucleotide barcodes of any one of embodiments 37 to 45, wherein the barcode sequence comprises about 5 to about 20 nucleotides, or about 10 to about 20 nucleotides.

Embodiment 47. The interposing oligonucleotide barcodes of any one of embodiments 37 to 45, wherein the barcode sequence comprises about 12 to about 16 nucleotides.

Embodiment 48. The interposing oligonucleotide barcodes of any one of embodiments 37 to 45, wherein each barcode sequence is selected from a set of barcode sequences represented by a random or partially random sequence.

Embodiment 49. The interposing oligonucleotide barcodes of any one of embodiments 37 to 45, wherein each barcode sequence is selected from a set of barcode sequences represented by a random sequence.

Embodiment 50. The interposing oligonucleotide barcodes of embodiment 49, wherein random sequence excludes a subset of sequences, wherein the excluded subset comprises sequences with three or more identical consecutive nucleotides.

Embodiment 51. The interposing oligonucleotide barcodes of embodiment 49, wherein each barcode sequence differs from every other barcode sequence by at least two nucleotide positions.

Embodiment 52. The interposing oligonucleotide barcodes of any one of embodiments 37 to 51, wherein the interposing oligonucleotide barcodes comprise a 5' phosphate.

Embodiment 53. A composition comprising a sample polynucleotide hybridized to the plurality of oligonucleotides barcodes of any one of embodiments 37 to 52.

Embodiment 54. The composition of embodiment 53, wherein the second hybridization pad of each interposing oligonucleotide barcode is at least twice as long as the first hybridization pad of each interposing oligonucleotide barcode.

Embodiment 55. The composition of embodiment 53, wherein the second hybridization pad of each interposing oligonucleotide barcode is about the same length as the first hybridization pad of each interposing oligonucleotide barcode.

Embodiment 56. The composition of embodiment 53, wherein the sample polynucleotide comprises a gene or a gene fragment.

Embodiment 57. A polynucleotide comprising a plurality of units, wherein each unit comprises a portion of a genomic sequence and a sequence of an interposing oligonucleotide barcode, wherein each interposing oligonucleotide barcode comprises from 5' to 3':
  a. a first stem region comprising a sequence common to the plurality of units;
  b. a loop region comprising a barcode sequence, wherein each barcode sequence in the polynucleotide is different; and
  c. a second stem region comprising a sequence complementary to the first stem region, wherein the second stem region hybridizes to the first stem region during the hybridizing.

Embodiment 58. The polynucleotide of embodiment 57, wherein the polynucleotide comprises three or more units.

Embodiment 59. The polynucleotide of embodiment 57 or 58, wherein each hybridization pad comprises about 9 to about 15 nucleotides of random sequence.

Embodiment 60. The polynucleotide of embodiment 57 or 58, wherein each hybridization pad comprises about 8 to about 12 nucleotides of random sequence.

Embodiment 61. The polynucleotide of any one of embodiments 57 to 60, wherein the first and second stem regions are complementary and wherein each stem region comprises a known sequence of about 5 to about 10 nucleotides.

Embodiment 62. The polynucleotide of any one of embodiments 57 to 60, wherein the first and second stem regions are complementary and wherein each stem region comprises a known sequence of about 6 to about 8 nucleotides.

Embodiment 63. The polynucleotide of any one of embodiments 57 to 62, wherein the barcode sequence comprises about 5 to about 20 nucleotides, or about 10 to about 20 nucleotides.

Embodiment 64. The polynucleotide of any one of embodiments 57 to 62, wherein the barcode sequence comprises about 5 to about 20 nucleotides, or about 12 to about 16 nucleotides.

Embodiment 65. The polynucleotide of any one of embodiments 57 to 64, wherein each barcode sequence is selected from a set of barcode sequences represented by a random or partially random sequence.

Embodiment 66. The polynucleotide of any one of embodiments 57 to 65, wherein each barcode sequence is selected from a set of barcode sequences represented by a random sequence.

Embodiment 67. The polynucleotides of embodiment 57, wherein the first stem region and the second stem region further comprise a sample index sequence.

Embodiment 68. The polynucleotide of any one of embodiments 57 to 67, wherein each barcode sequence differs from every other barcode sequence by at least two nucleotide positions.

Embodiment 69. The polynucleotide of any one of embodiments 57 to 68, wherein the interposing oligonucleotide barcodes comprise a 5' phosphate moiety.

Embodiment 70. The polynucleotide of any one of embodiments 57 to 69, wherein the polynucleotide comprises a gene or a gene fragment.

Embodiment 71. The polynucleotide of embodiment 70, wherein the gene is a cancer-associated gene or fragment thereof, T cell receptor (TCRs) gene or fragment thereof, or a B cell receptor (BCRs) gene, or fragment thereof.

Embodiment 72. The polynucleotide of embodiment 70, wherein the gene is a CDR3 gene or fragment thereof, T cell receptor alpha variable (TRAV) gene or fragment thereof, T cell receptor alpha joining (TRAJ) gene or fragment thereof, T cell receptor alpha constant (TRAC) gene or fragment thereof, T cell receptor beta variable (TRBV) gene or fragment thereof, T cell receptor beta diversity (TRBD) gene or fragment thereof, T cell receptor beta joining (TRBJ) gene or fragment thereof, T cell receptor beta constant (TRBC) gene or fragment thereof, T cell receptor gamma variable (TRGV) gene or fragment thereof, T cell receptor gamma joining (TRGJ) gene or fragment thereof, T cell receptor gamma constant (TRGC) gene or fragment thereof, T cell receptor delta variable (TRDV) gene or fragment thereof, T cell receptor delta diversity (TRDD) gene or fragment thereof, T cell receptor delta joining (TRDJ) gene or fragment thereof, or T cell receptor delta constant (TRDC) gene or fragment thereof.

Embodiment 73. The polynucleotide of any one of embodiments 57 to 72, wherein the polynucleotide comprises a sequence of genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA).

Embodiment 74. The polynucleotide of any one of embodiments 57 to 72, wherein the polynucleotide comprises a sequence of messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA).

Embodiment 75. A plurality of polynucleotides of any one of embodiments 57 to 74, wherein each polynucleotide in the plurality comprises a different combination of barcode sequences.

Embodiment 76. A plurality of tagged complements of a plurality of sample polynucleotides, produced according to the method of any one of embodiments 1 to 36.

Embodiment 77. A kit comprising a plurality of interposing oligonucleotide barcodes of any one of embodiments 37 to 52.

What is claimed:

1. A method of amplifying a tagged complement of a sample polynucleotide, the method comprising:
   a) hybridizing a first hybridization sequence of a first terminal adapter to the 3' end of said sample polynucleotide, wherein said first terminal adapter comprises from 5' to 3', a primer binding sequence, a barcode sequence, and said first hybridization sequence;
   b) hybridizing a second hybridization sequence of a second terminal adapter to the 5' end of said sample polynucleotide, wherein said second terminal adapter comprises from 5' to 3', the second hybridization sequence, a barcode sequence, and a primer binding sequence;
   c) hybridizing one or more interposing oligonucleotide barcode probe(s) to the sample polynucleotide, wherein each of the interposing oligonucleotide barcode probes comprise from 5' to 3', a first target hybridization sequence, a first stem sequence, a loop region comprising a barcode sequence; a second stem sequence; and a second target hybridization sequence;
   d) extending the 3' end of the first terminal adapter and extending the 3' end(s) of the second target hybridization sequences with one or more polymerases to create extension products; and
   e) ligating adjacent ends of the extension products hybridized to the sample polynucleotide, and amplifying an integrated strand comprising a tagged complement of the sample polynucleotide.

2. The method of claim 1, wherein step c) comprises hybridizing one interposing oligonucleotide barcode probe to the sample polynucleotide.

3. The method of claim 1, wherein step c) comprises hybridizing a plurality of interposing oligonucleotide barcode probes to the sample polynucleotide.

4. The method of claim 1, wherein the first terminal adapter, the second terminal adapter, or both the first terminal adapter and the second terminal adapter comprise one or more phosphorothioate-containing nucleotides or one or more LNAs.

5. The method of claim 1, wherein the first terminal adapter, the second terminal adapter, or both the first terminal adapter and the second terminal adapter comprise a modified nucleotide comprising an affinity tag.

6. The method of claim 1, wherein the first target hybridization sequence and the second target hybridization sequence each comprise about 9 to about 15 nucleotides and each terminal adapter hybridization sequence comprises about 10 to about 30 nucleotides.

7. The method of claim 1, wherein each of the one or more interposing oligonucleotide barcode probe(s) comprises a phosphorylated 5' end.

8. The method of claim 1, wherein the barcode of the first terminal adapter and the barcode of the second terminal adapter each comprise about 5 to 15 nucleotides.

9. The method of claim 1, wherein amplifying comprises hybridizing an amplification primer to the integrated strand and extending the amplification primer with a strand-displacing polymerase and nucleotides.

10. The method of claim 1, further comprising sequencing the complement of the integrated strand.

11. The method of claim 10, wherein the sequencing comprises: (A) fragmenting the complement of the integrated strand to produce fragments, (B) ligating adapters to the fragments, (C) amplifying the resultant products from step (B) to generate a polynucleotide, and (D) performing a sequencing reaction on the polynucleotide from step (C).

12. The method of claim 10, wherein the sequencing further comprises producing a plurality of sequencing reads; grouping sequencing reads based on co-occurrence of barcode sequences; and within each group, aligning the reads that belong to the same strand of the sample polynucleotide based on the sequences of the barcode sequences.

13. The method of claim 12, wherein each of the sequencing reads comprise at least a portion of two or more barcode sequences, or complements thereof.

14. The method of claim 12, further comprising computationally reconstructing sequences of a plurality of individual strands of the sample polynucleotide by removing interposing oligonucleotide barcode probe-derived sequences and joining sequences for adjacent portions of the sample polynucleotide.

15. The method of claim 12, wherein the sequencing further comprises forming a consensus sequence for reads having the same barcode sequence, or a portion thereof.

16. The method of claim 15, wherein the consensus sequence is obtained by comparing all sequencing reads aligning at a given nucleotide position, and identifying the nucleotide at that position as the one shared by a majority of the aligned reads.

17. The method of claim 1, wherein the complement of the integrated strand is greater than 500 bases in length.

18. A method of amplifying a nucleic acid molecule, said method comprising
    binding a first hybridization sequence of a first oligonucleotide probe to the nucleic acid molecule, wherein the first oligonucleotide probe comprises a first barcode sequence;
    binding a second oligonucleotide probe to the nucleic acid molecule, wherein the second oligonucleotide probe comprises a first target hybridization sequence, a second barcode sequence, and a second target hybridization sequence;
    binding a second hybridization sequence of a third oligonucleotide probe to the nucleic acid molecule, wherein the third oligonucleotide probe comprises a third barcode sequence;
    extending the first hybridization sequence and ligating the extended first hybridization sequence to the first target hybridization sequence, and extending the second target hybridization sequence and ligating the extended second target hybridization sequence to the second hybridization sequence to form an integrated strand comprising the first, second and third barcode sequences; and
    amplifying the integrated strand.

* * * * *

SEQUENCE LISTING

<160> NUMBER OF SEQ ID NOS: 11

<210> SEQ ID NO 1
<211> LENGTH: 15
<212> TYPE: DNA
<213> ORGANISM: Artificial Sequence
<220> FEATURE:
<223> OTHER INFORMATION: Synthetic Construct

<400> SEQUENCE: 1
cctattacga taaca                                                    15

<210> SEQ ID NO 2
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: Locked nucleic acid

<400> SEQUENCE: 2
accacggtca c                                                        11

<210> SEQ ID NO 3
<211> LENGTH: 6
<212> TYPE: DNA
<213> ORGANISM: Artificial Sequence
<220> FEATURE:
<223> OTHER INFORMATION: Synthetic Construct

<400> SEQUENCE: 3 ctccac                                                              6

<210> SEQ ID NO 4
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(14)
<223> OTHER INFORMATION: n is a, c, g, or t

<400> SEQUENCE: 4
ttnnnnnnnn nnnntt                                                   16

<210> SEQ ID NO 5
<211> LENGTH: 6
<212> TYPE: DNA
<213> ORGANISM: Artificial Sequence
<220> FEATURE:
<223> OTHER INFORMATION: Synthetic Construct

<400> SEQUENCE: 5 gtggag                                                              6

<210> SEQ ID NO 6
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature

```
<222> LOCATION: (4)..(4)
<223> OTHER INFORMATION: Locked nucleic acid

<400> SEQUENCE: 6
cgtctcctca g                                                          11

<210> SEQ ID NO 7
<211> LENGTH: 10
<212> TYPE: DNA
<213> ORGANISM: Artificial Sequence
<220> FEATURE:
<223> OTHER INFORMATION: Synthetic Construct

<400> SEQUENCE: 7
agcctgcctg                                                            10

<210> SEQ ID NO 8
<211> LENGTH: 10
<212> TYPE: DNA
<213> ORGANISM: Artificial Sequence
<220> FEATURE:
<223> OTHER INFORMATION: Synthetic Construct

<400> SEQUENCE: 8
tctaatgatc                                                            10

<210> SEQ ID NO 9
<211> LENGTH: 10
<212> TYPE: DNA
<213> ORGANISM: Artificial Sequence
<220> FEATURE:
<223> OTHER INFORMATION: Synthetic Construct

<400> SEQUENCE: 9
tcacggcgaa                                                            10

<210> SEQ ID NO 10
<211> LENGTH: 10
<212> TYPE: DNA
<213> ORGANISM: Artificial Sequence
<220> FEATURE:
<223> OTHER INFORMATION: Synthetic Construct

<400> SEQUENCE: 10
cgccagcact                                                            10

<210> SEQ ID NO 11
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(14)
<223> OTHER INFORMATION: n is a, c, g, or t

<400> SEQUENCE: 11
ttnnnnnnnn nnnntt                                                     16
```